(12) United States Patent
Seo et al.

(10) Patent No.: US 8,053,974 B2
(45) Date of Patent: Nov. 8, 2011

(54) ORGANOMETALLIC COMPLEX, AND LIGHT EMITTING DEVICE AND ELECTRONIC APPLIANCE USING THE SAME

(75) Inventors: Satoshi Seo, Kanagawa (JP); Hideko Inoue, Kanagawa (JP); Nobuharu Ohsawa, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 964 days.

(21) Appl. No.: 11/909,130

(22) PCT Filed: Mar. 22, 2006

(86) PCT No.: PCT/JP2006/306377
§ 371 (c)(1), (2), (4) Date: Sep. 19, 2007

(87) PCT Pub. No.: WO2006/104177
PCT Pub. Date: Oct. 5, 2006

(65) Prior Publication Data
US 2009/0033209 A1 Feb. 5, 2009

(30) Foreign Application Priority Data

Mar. 28, 2005 (JP) .................. 2005-091349
Nov. 8, 2005 (JP) .................. 2005-324037

(51) Int. Cl.
*H01L 51/54* (2006.01)
*C09K 11/06* (2006.01)
*C07D 241/36* (2006.01)

(52) U.S. Cl. ............... 313/504; 544/225; 257/E51.044; 428/917

(58) Field of Classification Search ........................ None
See application file for complete search history.

(56) References Cited

U.S. PATENT DOCUMENTS

| | | | |
|---|---|---|---|
| 6,821,646 B2 | 11/2004 | Tsuboyama et al. | 428/690 |
| 6,835,469 B2 | 12/2004 | Kwong et al. | 428/690 |
| 7,220,495 B2 | 5/2007 | Tsuboyama et al. | 428/690 |
| 7,238,806 B2 | 7/2007 | Inoue et al. | 544/225 |
| 2005/0191527 A1* | 9/2005 | Fujii et al. | 428/917 |
| 2005/0221123 A1* | 10/2005 | Inoue et al. | 428/690 |
| 2005/0242715 A1 | 11/2005 | Inoue et al. | 313/504 |
| 2007/0213527 A1 | 9/2007 | Inoue et al. | 544/225 |
| 2009/0015143 A1 | 1/2009 | Inoue et al. | 313/504 |

FOREIGN PATENT DOCUMENTS

| | | |
|---|---|---|
| EP | 1 191 612 A2 | 3/2002 |
| EP | 1 690 866 A1 | 8/2006 |
| JP | 2003-81988 | 3/2003 |
| JP | 2005-506361 | 3/2005 |
| JP | 2005-239648 | 9/2005 |
| WO | WO 2006/098460 A1 | 8/2006 |

OTHER PUBLICATIONS

European Search Report re application No. EP 06730325.5, dated Jul. 26, 2010.
International Search Report re application No. PCT/JP2006/306377, dated Jun. 13, 2006.
Written Opinion re application No. PCT/JP2006/306377, dated Jun. 13, 2006.
Hwang, F-M et al, "Iridium(III) Complexes with Orthometalated Quinoxaline Ligands: Subtle Tuning of Emission to the Saturated Red Color," Inorganic Chemistry, vol. 44, No. 5, Feb. 4, 2005, pp. 1344-1353.
Duan, J-P et al, "New Iridium Complexes as Highly Efficient Orange-Red Emitters in Organic Light-Emitting Diodes," Advanced Materials, vol. 15, No. 3, Feb. 5, 2003, pp. 224-228.
Zhang, G-L et al, "Synthesis and Phosphorescence of a New Iridium(III) Pyrazine Complex," Acta Phys.-Chim. Sin., (Wuli Huaxue Xuebao), vol. 19, No. 10, Oct. 2003, pp. 889-891 (with English abstract).
Zhang, G-L et al, "Synthesis and Luminescence Property of a New Yellow Phosphorescent Iridium(III) Pyrazine Complex," Chemical Journal of Chinese Universities, vol. 25, No. 3, Mar. 2004, pp. 397-400 (with English abstract).
Yersin, H. et al, "Triplet Emitters for Organic Light-Emitting Diodes: Basic Properties," *Highly Efficient OLEDs with Phosphorescent Materials,* Wiley-VCH Verlag GmbH & Co. KGaA, 2008, pp. 1-18.
Office Action re European Application No. EP 06730325.5, dated Jun. 24, 2011.

\* cited by examiner

Primary Examiner — Jennifer Chriss
Assistant Examiner — Camie S Thompson
(74) Attorney, Agent, or Firm — Husch Blackwell LLP

(57) ABSTRACT

In a general formula (1), each of $R_1$ and $R_2$ represents any one of hydrogen, an alkyl group, a halogen group, —CF3, an alkoxy group, and an aryl group. M represents an element that belongs to Group 9 or Group 10. Here, an alkyl group having 1 to 4 carbon atoms is preferable in the alkyl group. A fluoro group is particularly preferable in the halogen group. An alkoxy group having 1 to 4 carbon atoms is preferable in the alkoxy group. A phenyl group is particularly preferable in the aryl group. Iridium is particularly preferable among the elements that belong to Group 9, and platinum is particularly preferable among the elements that belong to Group 10. The general formula (1) is inserted.

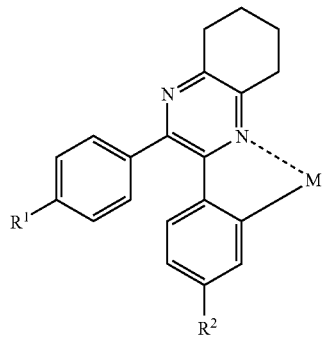

(1)

71 Claims, 36 Drawing Sheets

ORGANOMETALLIC COMPLEX, AND LIGHT EMITTING DEVICE AND ELECTRONIC APPLIANCE USING THE SAME

TECHNICAL FIELD

The present invention relates to a substance which can emit light by current excitation, and specifically, an organometallic complex which emits light by current excitation. Furthermore, the present invention relates to a light-emitting element and a light-emitting device, each of which uses the substance.

BACKGROUND ART

A light-emitting element including a layer containing a light-emitting substance between a pair of electrodes is used as a pixel, a light source, or the like, and is provided in a light-emitting device such as a display device or a lightening system. An excited light-emitting substance emits fluorescence or phosphorescence when current is applied between a pair of electrodes of a light-emitting element.

In theory, internal quantum efficiency of phosphorescence is about three times as large as that of fluorescence in a case of current excitation, when fluorescence and phosphorescence are compared with each other. Therefore, it is considered that light-emitting efficiency is increased by using a light-emitting substance which emits phosphorescence than using a light-emitting substance which emits fluorescence, and a substance which emits phosphorescence has been developed so far.

For example, a metal complex having iridium as its central metal is disclosed in Patent Document 1. According to Patent Document 1, high-efficiency organic light-emitting device can be obtained by using the metal complex.

As described above, a light-emitting element which operates efficiently can be obtained by using a metal complex. However, metal such as iridium or platinum which is used as a central metal of a metal complex is expensive. Therefore, there is a problem that cost of raw materials for manufacturing a light-emitting element is high in a case of using a metal complex.

Patent Document 1: Published Japanese translation of PCT international application, No. 2005-506361

DISCLOSURE OF INVENTION

It is an object of the present invention to provide an organometallic complex which can emit phosphorescence. It is also an object of the present invention to provide an organometallic complex which can be synthesized with high yield. In addition, it is an object of the present invention to provide a light-emitting element which emits light efficiently and can be manufactured at low cost.

One aspect of the present invention is an organometallic complex including a structure represented by a general formula (1).

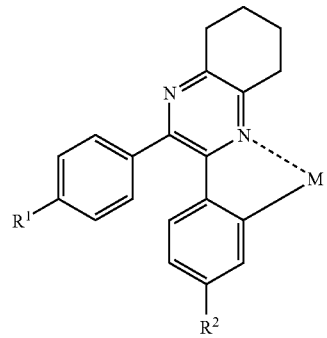

In the general formula (1), each of $R^1$ and $R^2$ represents any one of hydrogen, an alkyl group, a halogen group, —$CF_3$, an alkoxy group, and an aryl group. M represents an element that belongs to Group 9 or Group 10 of the periodic table. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group. Iridium is particularly preferable among the elements that belong to Group 9, and platinum is particularly preferable among the elements that belong to Group 10.

Another aspect of the present invention is an organometallic complex represented by a general formula (2).

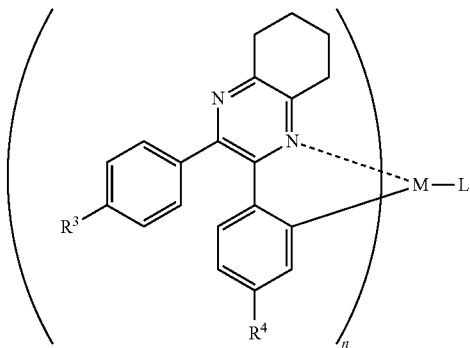

In the general formula (2), each of $R^3$ and $R^4$ represents any one of hydrogen, an alkyl group, a halogen group, —$CF_3$, an alkoxy group, and an aryl group. M represents an element that belongs to Group 9 or Group 10 of the periodic table. Also, L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group. Iridium is particularly preferable among the elements that belong to Group 9, and platinum is particularly preferable among the elements that belong to Group 10. Further, n=2 when M is an element that belongs to Group 9, and n=1 when M is an element that belongs to Group 10.

Another aspect of the present invention is an organometallic complex including a structure represented by a general formula (3).

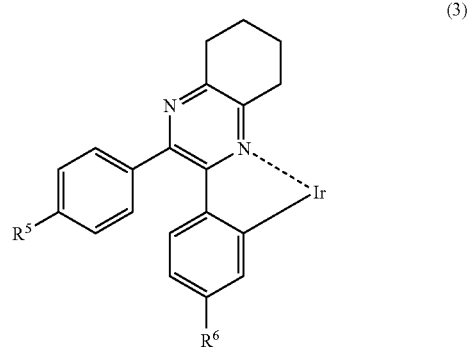

(3)

In the general formula (3), each of $R^5$ and $R^6$ represents any one of hydrogen, an alkyl group, a halogen group, —$CF_3$, an alkoxy group, and an aryl group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group.

Another feature of the present invention is an organometallic complex including a structure represented by a general formula (4).

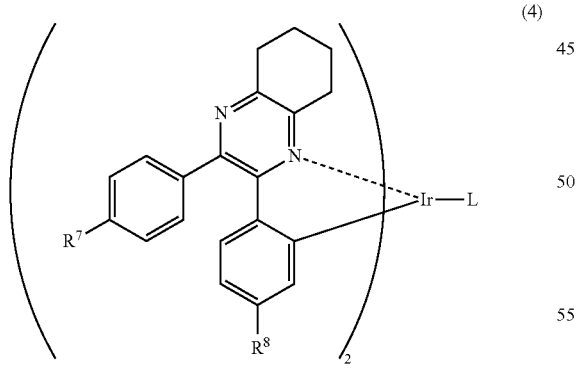

(4)

In the general formula (4), each of $R^7$ and $R^8$ represents any one of hydrogen, an alkyl group, a halogen group, —$CF_3$, an alkoxy group, and an aryl group. L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, a sec-butyl group, and tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group.

As for organometallic complexes represented by the general formulas (2) and (4), it is preferable that L be any ligand selected from ligands represented by following structural formulas (1) to (7) specifically.

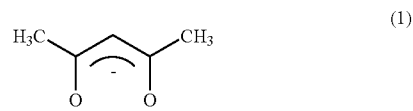

(1)

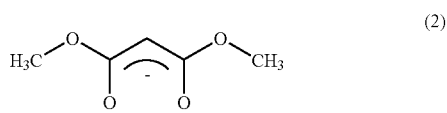

(2)

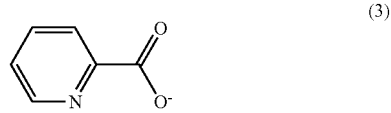

(3)

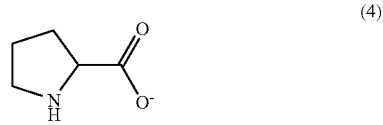

(4)

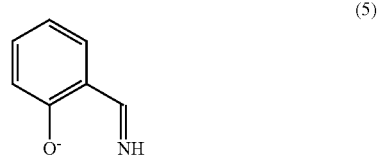

(5)

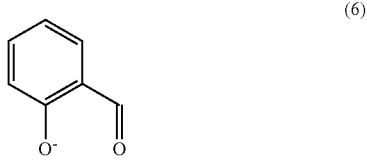

(6)

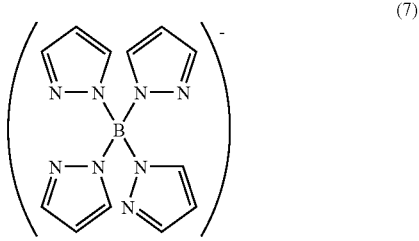

(7)

Another aspect of the present invention is an organometallic complex including a structure represented by a general formula (5).

(5)

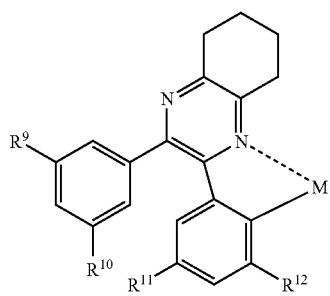

In the general formula (5), each of $R^9$ to $R^{12}$ represents any one of hydrogen, an alkyl group, a halogen group, —$CF_3$, an alkoxy group, and an aryl group. M represents an element that belongs to Group 9 or Group 10 of the periodic table. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group. Iridium is particularly preferable among the elements that belong to Group 9, and platinum is particularly preferable among the elements that belong to Group 10.

Another aspect of the present invention is an organometallic complex represented by a general formula (6).

(6)

In the general formula (6), each of $R^{13}$ to $R^{16}$ represents any one of hydrogen, an alkyl group, a halogen group, —$CF_3$, an alkoxy group, and an aryl group. M represents an element that belongs to Group 9 or Group 10 of the periodic table. Also, L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, and a sec-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group. Iridium is particularly preferable among the elements that belong to Group 9, and platinum is particularly preferable among the elements that belong to Group 10. Further, n=2 when M is an element that belongs to Group 9, and n=1 when M is an element that belongs to Group 10.

Another aspect of the present invention is an organometallic complex including a structure represented by a general formula (7).

(7)

In the general formula (7), each of $R^{17}$ to $R^{20}$ represents any one of hydrogen, an alkyl group, a halogen group, —$CF_3$, an alkoxy group, and an aryl group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group.

Another aspect of the present invention is an organometallic complex including a structure represented by a general formula (8).

(8)

In the general formula (8), each of $R^{21}$ and $R^{24}$ represents any one of hydrogen, an alkyl group, a halogen group, —$CF_3$, an alkoxy group, and an aryl group. L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. A phenyl group is particularly preferable in the aryl group.

As for an organometallic complex represented by the general formulas (6) and (8), it is preferable that L be any ligand selected from ligands represented by following structural formulas (1) to (7) specifically.

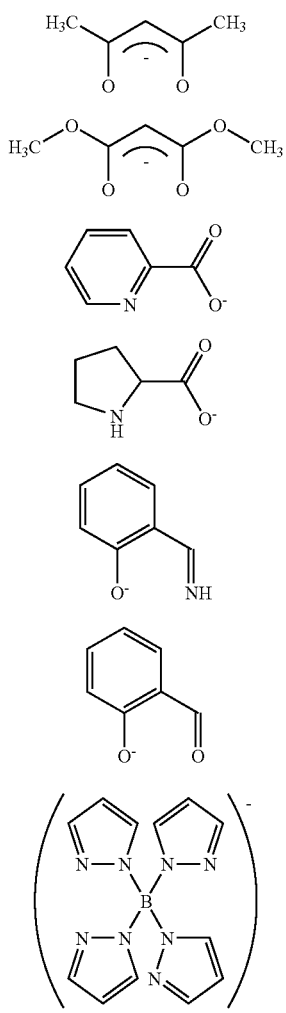

Another aspect of the present invention is an organometallic complex including a structure represented by a general formula (9).

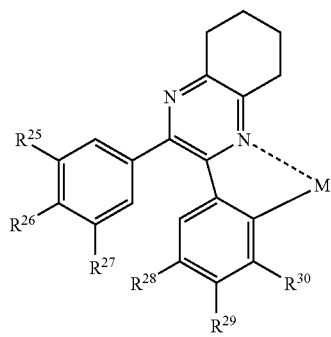

In the general formula (9), each of $R^{25}$ to $R^{30}$ represents any one of hydrogen, an alkyl group, a halogen group, —$CF_3$, and an alkoxy group. M represents an element that belongs to Group 9 or Group 10. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. Iridium is particularly preferable among the elements that belong to Group 9, and platinum is particularly preferable among the elements that belong to Group 10.

Another aspect of the present invention is an organometallic complex represented by a general formula (10).

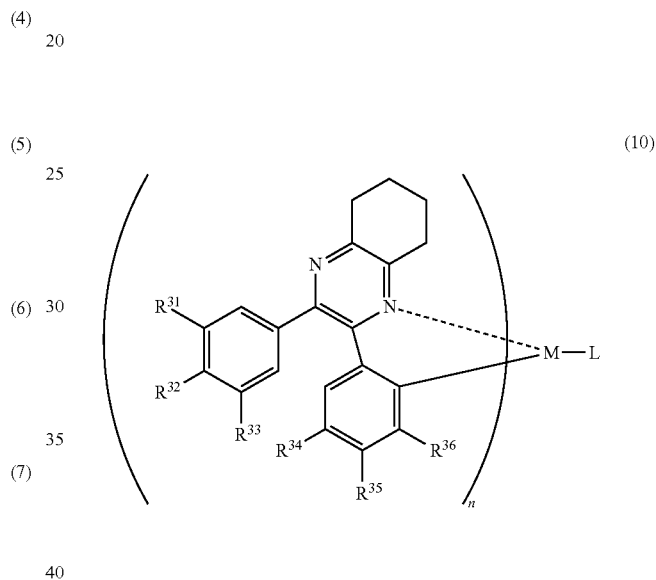

In the general formula (10), each of $R^{31}$ to $R^{36}$ represents any one of hydrogen, an alkyl group, a halogen group, —$CF_3$, and an alkoxy group. M represents an element that belongs to Group 9 or Group 10 of the periodic table. Also, L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable. Iridium is particularly preferable among the elements that belong to Group 9, and platinum is particularly preferable among the elements that belong Group 10. Further, n=2 when M is an element that belongs to Group 9, and n=1 when M is an element that belongs to Group 10.

Another aspect of the present invention is an organometallic complex including a structure represented by a general formula (11).

(11)

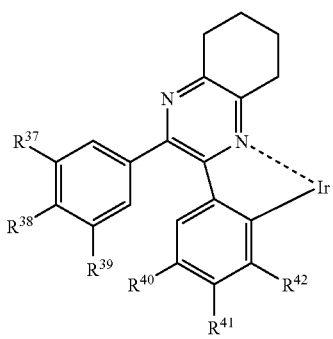

In the general formula (11), each of $R^{37}$ to $R^{42}$ represents any one of hydrogen, an alkyl group, a halogen group, —$CF_3$, and an alkoxy group. Here, an alkyl group having 1 to 4 carbon atoms is preferable in the alkyl group, and particularly, any group selected from a methyl group, an ethyl group, an isopropyl group, a sec-butyl group, and a tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable.

Another aspect of the present invention is an organometallic complex including a structure represented by a general formula (12).

(12)

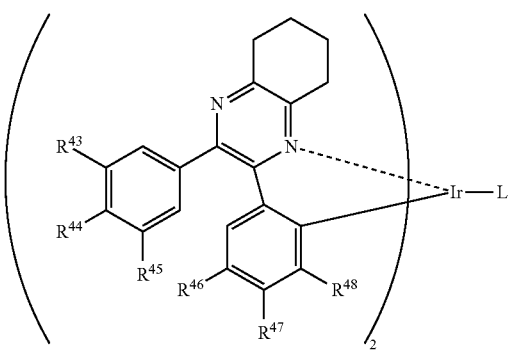

In the general formula (12), each of $R^{43}$ to $R^{48}$ represents any one of hydrogen, an alkyl group, a halogen group, —$CF_3$, and an alkoxy group. L represents any one of a monoanionic ligand having a beta-diketone structure, a monoanionic bidentate chelate ligand having a carboxyl group, and a monoanionic bidentate chelate ligand having a phenol hydroxyl group. Here, an alkyl group having 1 to 4 carbon atoms is preferable in the alkyl group, and particularly, any group selected from a methyl group, an ethyl group, an isopropyl group, a sec-butyl group, and tert-butyl group is preferable. A fluoro group is particularly preferable in the halogen group since chemical stability is improved. Also, an alkoxy group having 1 to 4 carbon atoms is preferable in the alkoxy group, and particularly, a methoxy group is preferable.

As for organometallic complexes represented by the general formulas (10) and (12), it is preferable that L be any ligand selected from ligands represented by following structural formulas (1) to (7) specifically. The ligands represented by the structural formulas (1) to (7) are monoanionic ligands.

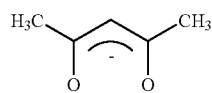
(1)

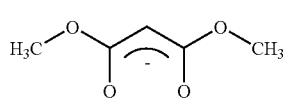
(2)

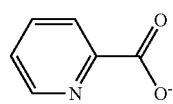
(3)

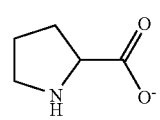
(4)

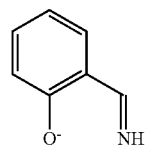
(5)

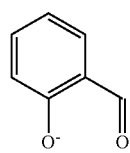
(6)

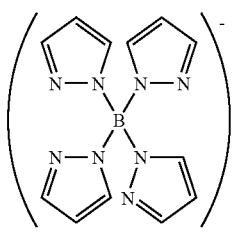
(7)

Another aspect of the present invention is that, as for the organometallic complex including the structure represented by the general formula (1), each of $R^1$ and $R^2$ is hydrogen or fluorine, and M is iridium or platinum, particularly.

Another aspect of the present invention is that, as for an organometallic complex represented by the general formula (2), each of $R^3$ and $R^4$ is hydrogen or fluorine, M is iridium or platinum, and L is any one of an acetylacenato ligand, a picolinato ligand and a tetrakis(1-pyrazolyl)borate ligand, particularly. Specifically, it is an organometallic complex represented by a general formula (13).

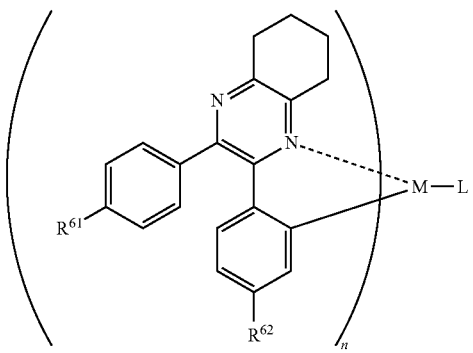

(13)

In the general formula (13), each of $R^{61}$ and $R^{62}$ represents hydrogen or fluorine. M represents iridium or platinum. Also, L represents a ligand represented by any one of structural formulas (36) to (38). Further, n=2 when M is iridium, and n=1 when M is platinum.

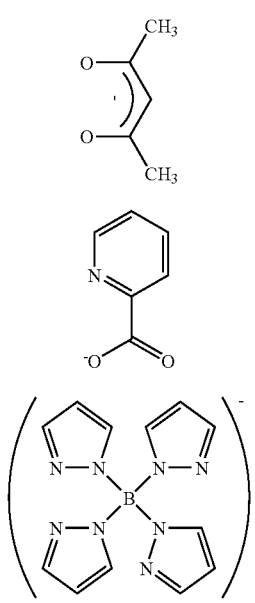

It is to be noted that a dashed line included in each of general formulas described above denotes a coordinate bond.

Another aspect of the present invention is a light-emitting element containing an organometallic complex represented by any one of the general formulas (1) to (13). The light-emitting element includes a layer containing an organometallic complex represented by any one of the general formulas (1) to (13) between electrodes, and it is preferable that the light-emitting element include a structure in which the organometallic complex represented by any one of the general formulas (1) to (13) emits light when a current is applied between the electrodes. As described above, a light-emitting element using the organometallic complex of the present invention as a light-emitting substance can obtain phosphorescence; therefore, the light-emitting element emits light efficiently. Also, the organometallic complex of the present invention can be synthesized with high yield and is productive; therefore, a light-emitting element with reduced cost of raw materials can be manufactured by using the organometallic complex of the present invention.

Another aspect of the present invention is a light-emitting device using a light-emitting element containing an organometallic complex represented by any one of the general formulas (1) to (13) as a pixel or a light source. As described above, the light-emitting element of the present invention emits light efficiently; therefore, a light-emitting device which is driven with low power consumption can be obtained by using the light-emitting element of the present invention. Also, the light-emitting element of the present invention can be manufactured at low cost; therefore a light-emitting device with low production cost and low price can be obtained by using the light-emitting element of the present invention.

By carrying out the present invention, an organometallic complex which emits phosphorescence can be obtained. Also, an organometallic complex which can be synthesized with high yield can be obtained by carrying out the present invention.

By carrying out the present invention, a light-emitting element which can emit phosphorescence and particularly has high internal quantum efficiency can be obtained. Also, a light-emitting element with low cost of raw materials can be obtained by carrying out the present invention.

By carrying out the present invention, a light-emitting device which emits light efficiently and with low production cost can be obtained.

BEST MODE FOR CARRYING OUT THE INVENTION

Figure 1:
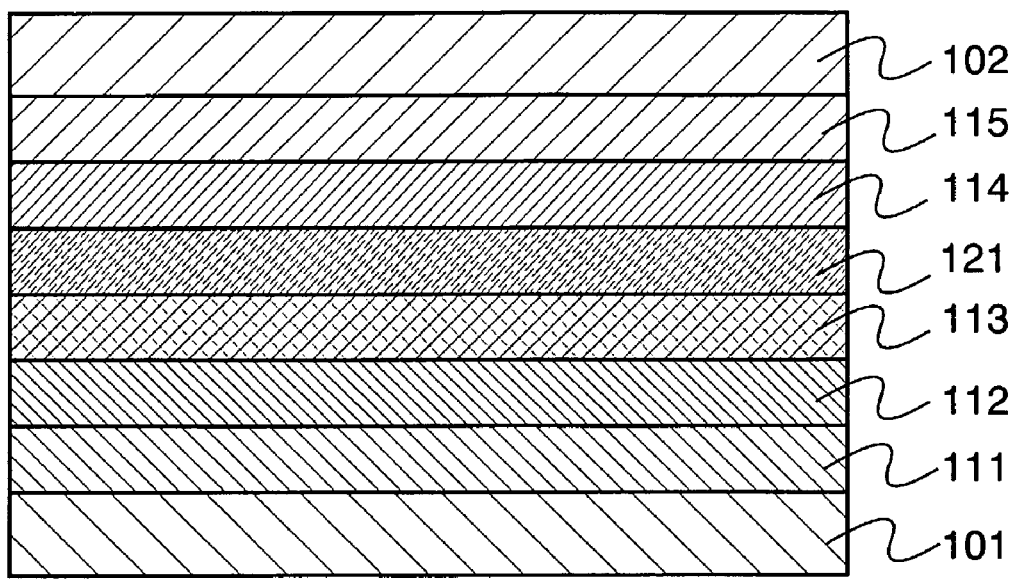
FIG. 1 is a view explaining one mode of a light-emitting device of the present invention.

Hereinafter, one mode of the present invention will be described. However, the present invention can be carried out in many different modes, and it is easily understood by those skilled in the art that modes and details thereof can be modified in various ways without departing from the spirit and the scope of the present invention. Therefore, the present invention is not understood as being limited to the description of this mode.

Embodiment Mode 1

Organometallic complexes represented by structural formulas (8) to (34) are given as one mode of the present invention. However, the present invention is not limited to the descriptions here, and an organometallic complex including a structure represented by any one of general formulas (1), (3), (5), (7), (9), and (11), or an organometallic complex represented by any one of general formulas (2), (4), (6), (8), (10), (12), and (13) may be used.

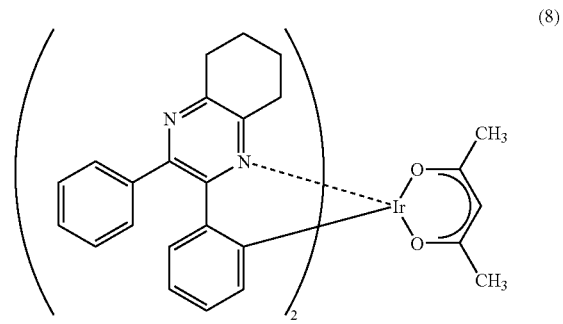

(8)

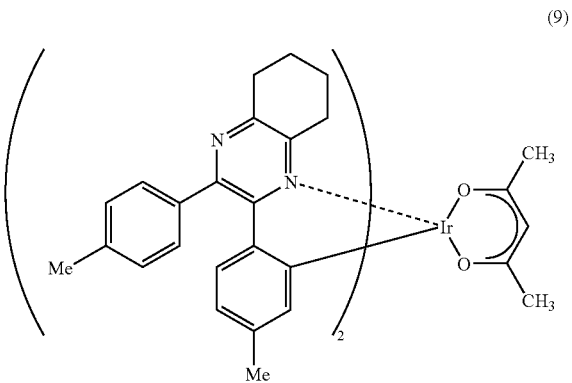

(9)

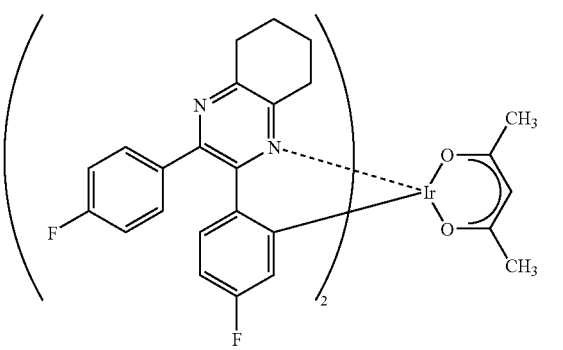

(10)

(11)
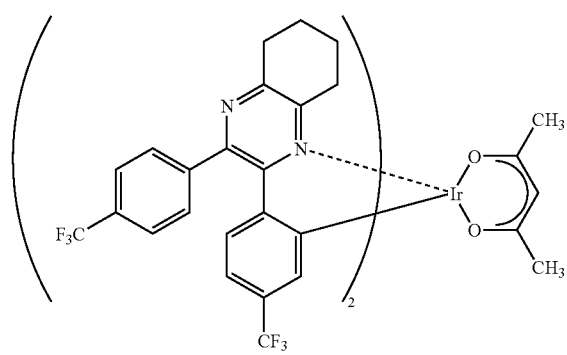
(12)
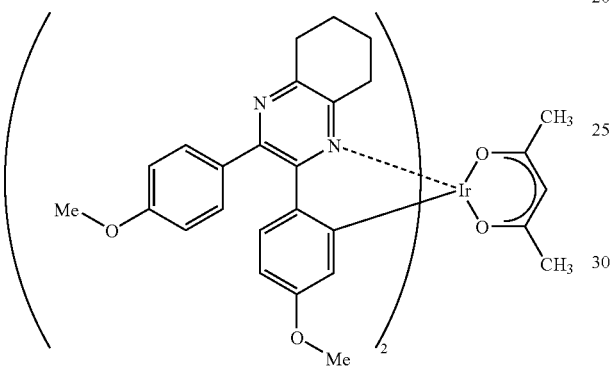
(13)
(14)
(15)
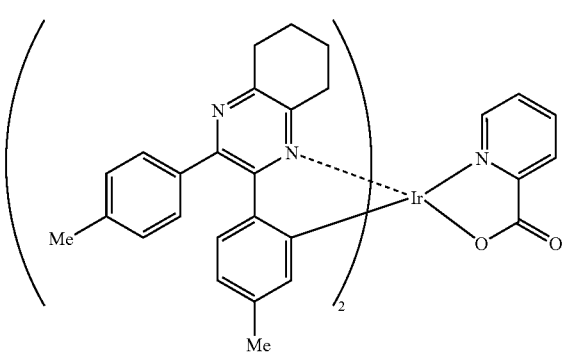
(16)
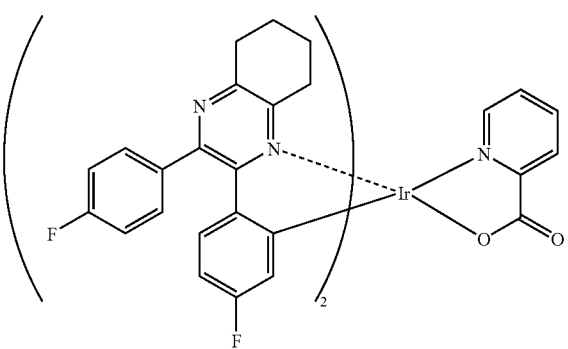
(17)
(18)
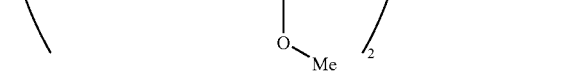

(19) 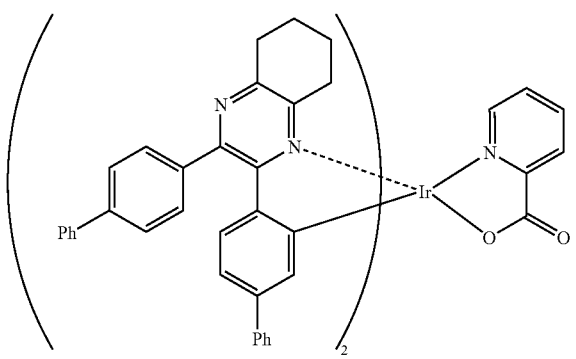
(20) 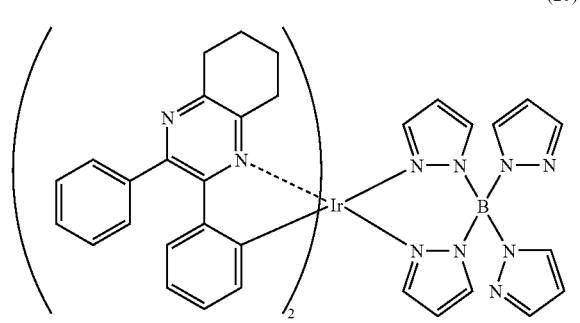
(21) 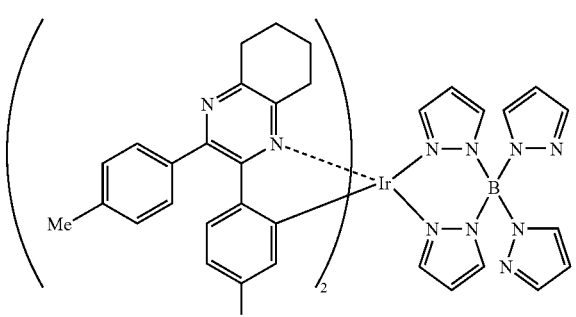
(22) 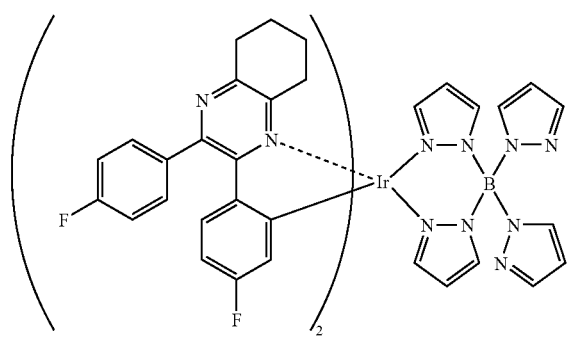
(23) 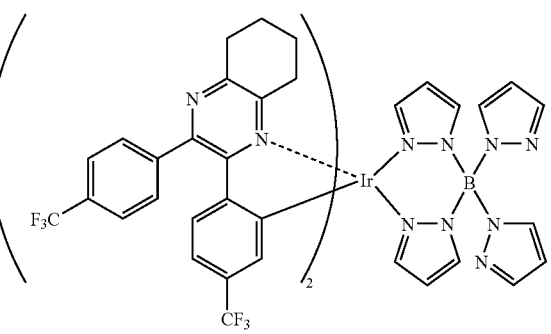
(24) 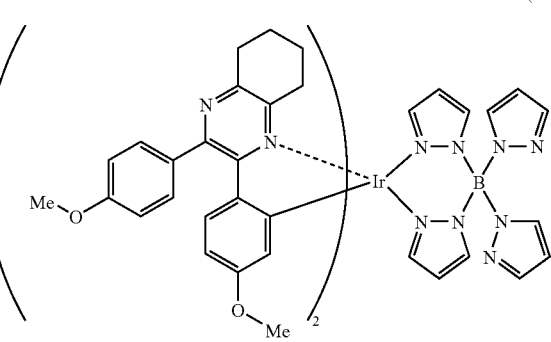
(25) 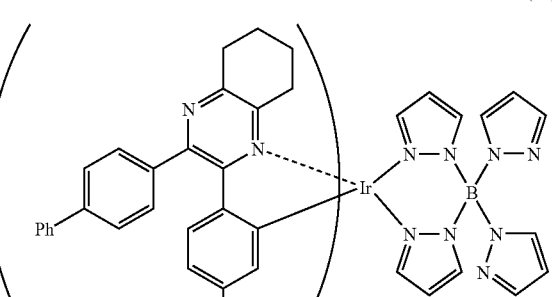
(26) 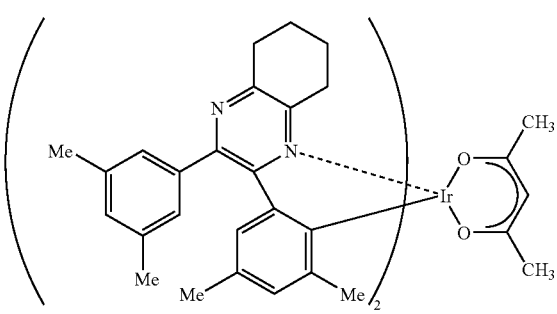

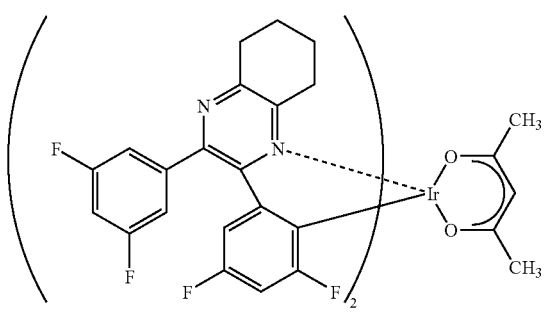

(27)

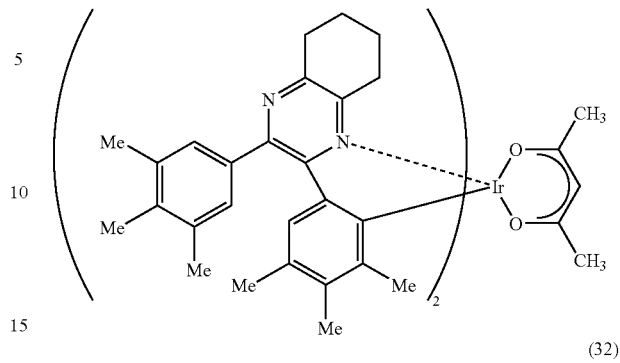

(31)

(28)

(32)

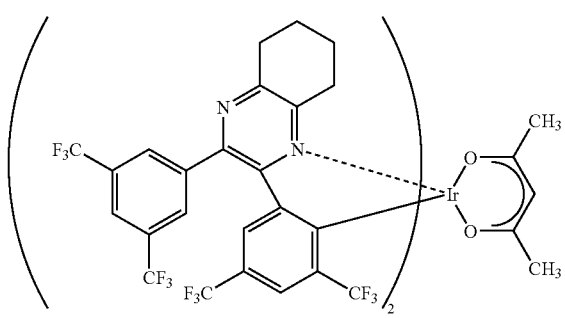

(33)

(29)

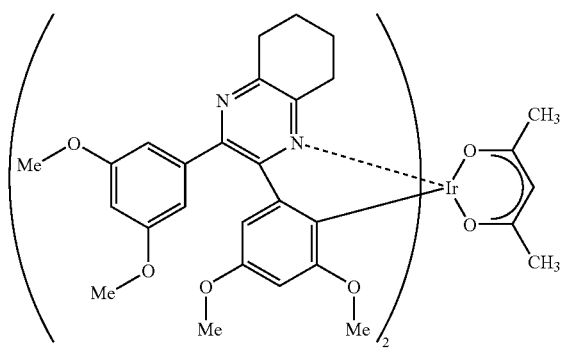

(34)

(30)

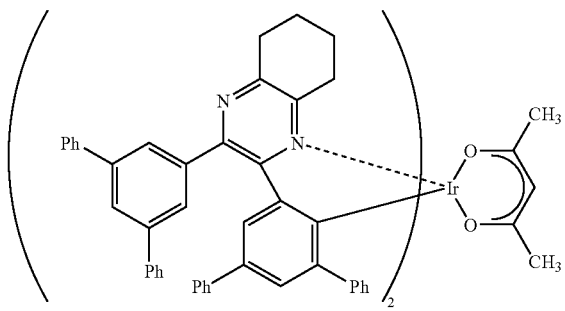

The organometallic complexes of the present invention described above emit phosphorescence. Therefore, a light-emitting element having high internal quantum efficiency and high light-emitting efficiency can be manufactured by using the organometallic complex of the present invention as a light-emitting substance. Also, the organometallic complexes of the present invention described above can be synthesized with high yield. Therefore, a light-emitting element having low cost of raw materials can be manufactured by using the organometallic complex of the present invention.

Embodiment Mode 2

Hereinafter, a mode of synthesis of an organometallic complex of the present invention will be described. Note that the organometallic complex of the present invention is not limited to only an organometallic complex obtained by a synthesis method explained in this mode, and an organometallic complex including a structure represented by any one of general formulas (1), (3), (5), (7), (9), and (11), or an organometallic complex represented by any one of general formulas (2), (4), (6), (8), (10), (12), and (13) may be used.
[Organometallic Complexes Represented by Structural Formulas (8) to (25)]

An organometallic complex of the present invention represented by any one of structural formulas (8) to (25) is obtained by a synthesis method as represented by following synthesis schemes (a-1) to (a-3). First, α-diketone and 1,2-cyclohexanediamine are dehydrated and condensed, and thereafter, dehydrogenated using iron chloride (III) or the like, and accordingly, a ligand including a skeleton of tetrahydroquinoxaline is synthesized as shown in the synthesis scheme (a-1). Thereafter, the synthesized ligand is mixed with iridium(III) chloride hydrochloride hydrate and coordinated with iridium, and a dinuclear complex is synthesized as represented by the synthesis scheme (a-2). Furthermore, as represented by the synthesis scheme (a-3), the dinuclear complex which is synthesized previously and a monoanionic ligand such as acetylacetone or pocoline acid are reacted, and the monoanionic ligand is coordinated with iridium; accordingly, the organometallic complex of the present invention can be obtained.

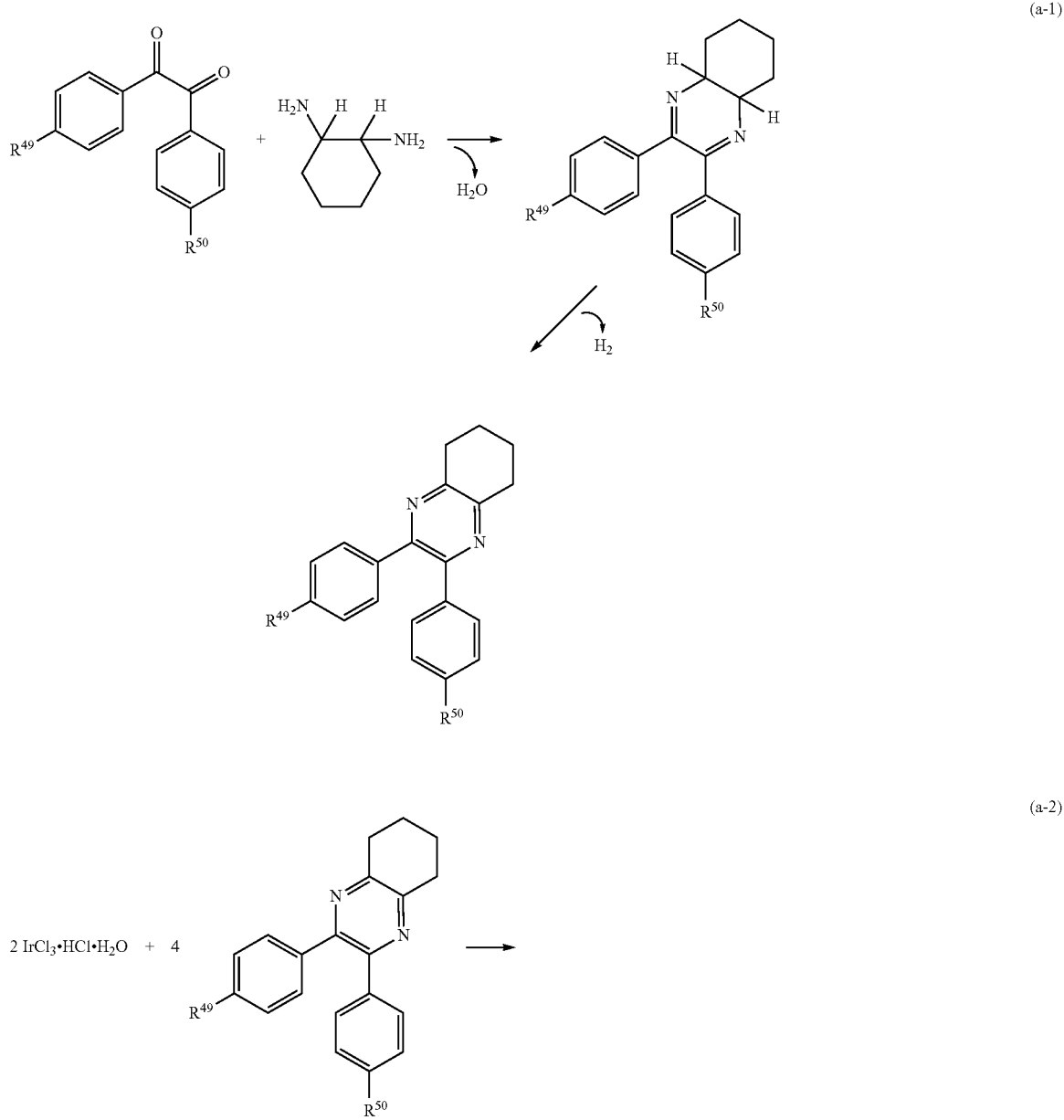

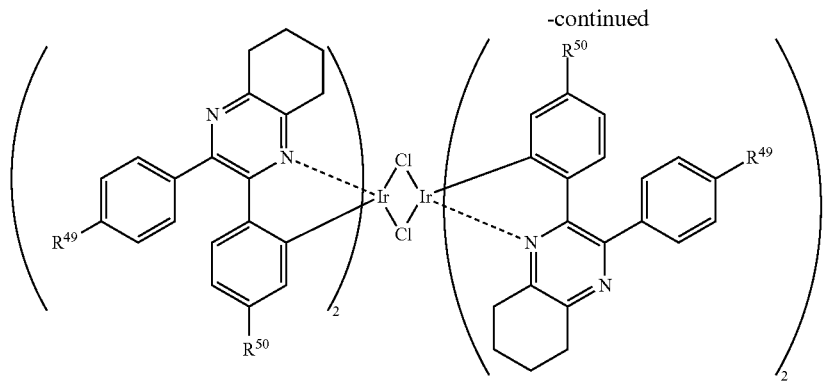

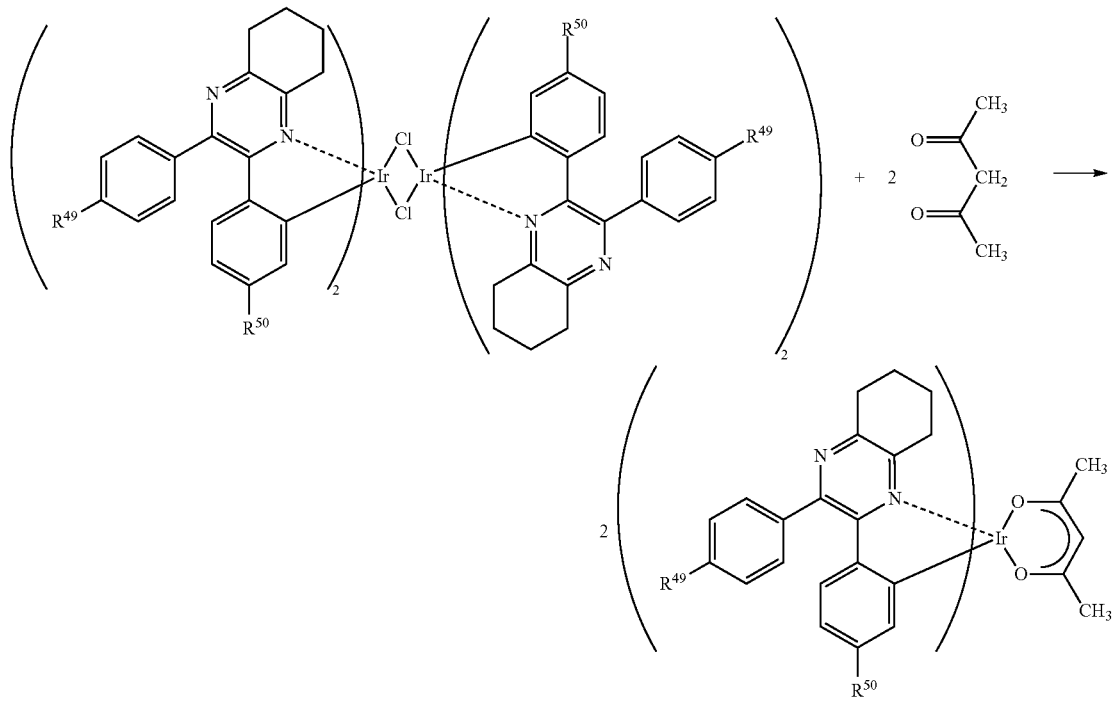

In the synthesis schemes (a-1) to (a-3), each of $R^{49}$ and $R^{50}$ represents any one of hydrogen, a methyl group, a fluoro group, —$CF_3$, a methoxy group, and a phenyl group. L represents any one of acetylacetone, picolone acid, and tetrapyrazolato boronate.

A synthesis method of the organometallic complex of the present invention is not limited to the method represented by the synthesis schemes (a-1) to (a-3). However, as in the synthesis method of this mode, by applying a synthesis method including a step in which a ligand is obtained by using 1,2-cyclohexanediamine as a raw material, the organometallic complex of the present invention can be obtained with high yield. This is especially because the yield in synthesizing the ligand represented by the synthesis scheme (a-1) becomes high by using 1,2-cyclohexanediamine. Here, 1,2-cyclohexanediamine may be either a cis form or a trans form. Alternatively, it may be 1,2-cyclohexanediamine which has optical activity, or 1,2-cyclohexanediamine which does not have optical activity.

In the synthesis scheme (a-1), $R^{49}$ and $R^{50}$ use α-diketone represented by any one of an ethyl group, an isopropyl group, a sec-butyl group, and an ethoxy group as a raw material, and accordingly, other organometallic complexes of the present invention different from the organometallic complexes represented by the structural formulas (8) to (25) can be obtained. Also, by using a salt containing platinum such as tetrachloro platinum potassium instead of iridium(III) chloride hydrochloride hydrate, an organometallic complex of the present invention containing platinum as its central metal can be obtained. Also, by using a ligand such as dimethyl malonate, salicyl aldehyde, or salicylidene amine instead of acetylacetone, picolone acid, and tetrapyrazolato boronate, organometallic complexes of the present invention containing ligands as represented by structural formulas (2) and (4) to (6) can also be obtained.

[Organometallic Complexes Represented by Structural Formulas (26) to (30)]

An organometallic complex of the present invention represented by any one of structural formulas (26) to (30) is obtained by a synthesis method as represented by following synthesis schemes (b-1) to (b-3). As shown in the synthesis scheme (b-1), α-diketone and 1,2-cyclohexanediamine are dehydrated and condensed, and thereafter, dehydrogenated using iron chloride (III) or the like, and accordingly, a ligand including a skeleton of tetrahydroquinoxaline is synthesized. Thereafter, the synthesized ligand is mixed with iridium(III)

chloride hydrochloride hydrate and coordinated with iridium as represented by the synthesis scheme (b-2). As represented by the synthesis scheme (b-3), a monoanionic ligand is coordinated with iridium, and a dinuclear complex is synthesized. Furthermore, as represented by the synthesis scheme (b-3), the dinuclear complex which is synthesized previously and a monoanionic ligand, such as acetylacetone or pocoline acid are reacted, and the monoanionic ligand is coordinated with iridium; accordingly, the organometallic complex of the present invention can be obtained.

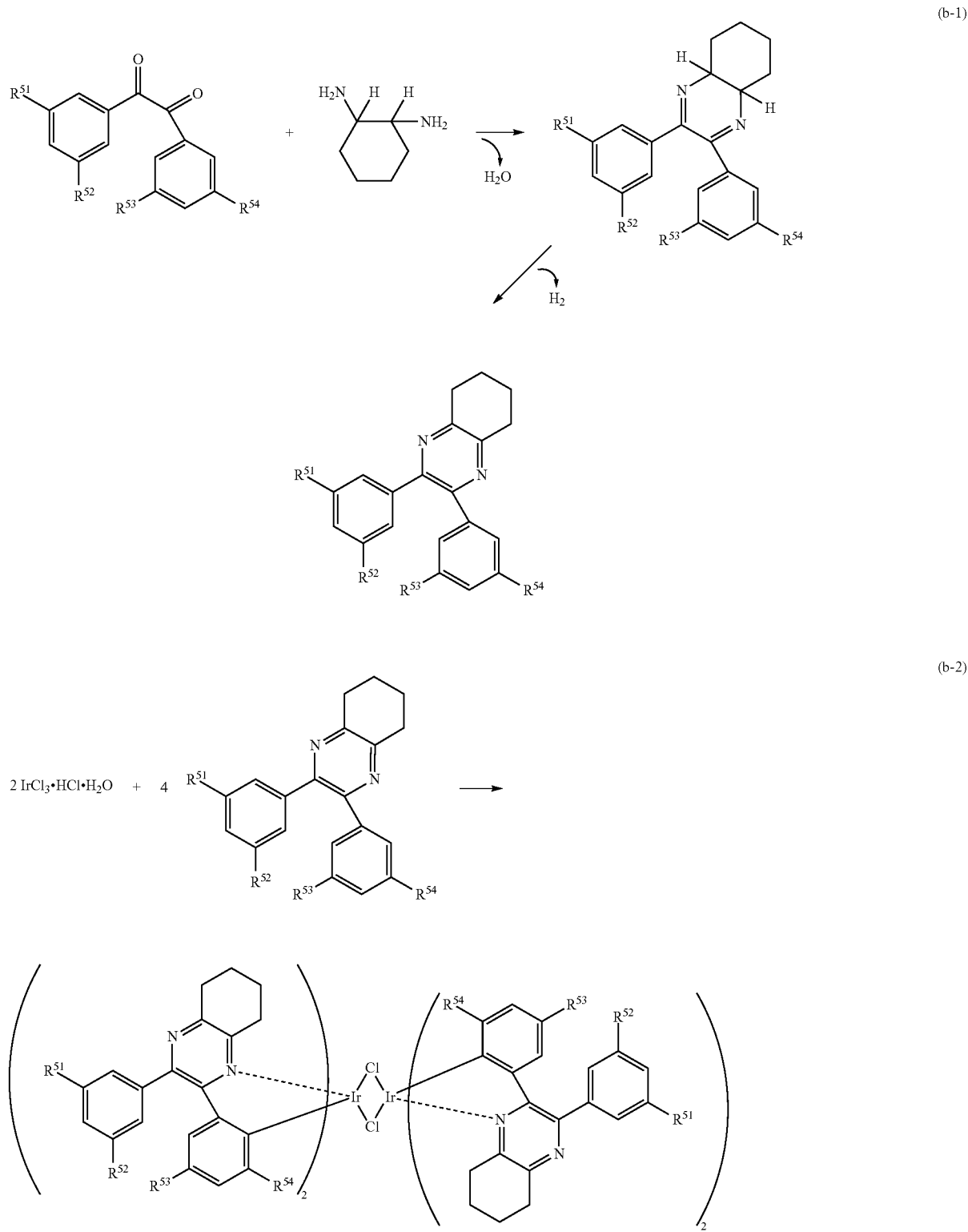

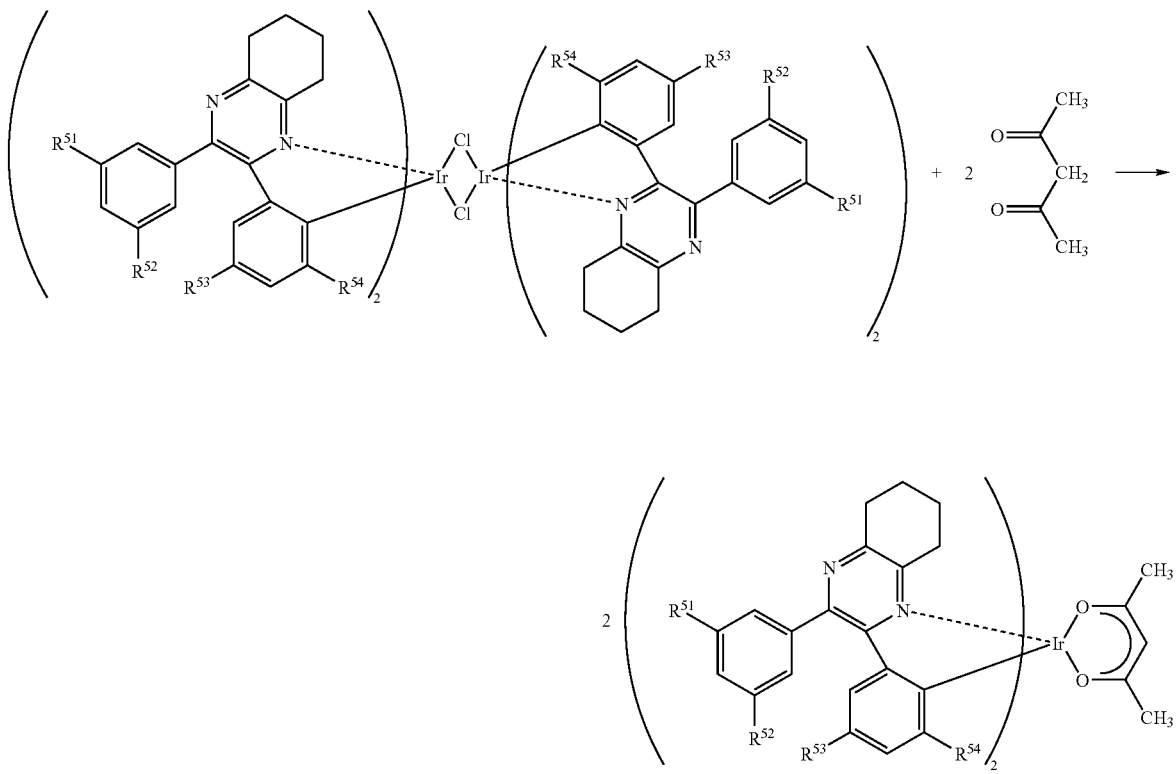

In the synthesis schemes (b-1) to (b-3), each of $R^{51}$ to $R^{54}$ represents any one of a methyl group, a fluoro group, —$CF_3$, a methoxy group, and a phenyl group. L represents acetylacetone. Note that α-diketone which is used for a reaction in the synthesis scheme (b-1) can be obtained by a reaction of Grignard reagent of benzene, of which the third position and the fifth position are substituted by any one of a methyl group, a fluoro group, —$CF_3$, a methoxy group and a phenyl group, with 1,4-dimethylpiperazine-2,3-dione.

A synthesis method of the organometallic complex of the present invention is not limited to the method represented by the synthesis schemes (b-1) to (b-3). However, as in the synthesis method of this mode, by applying a synthesis method including a step in which a ligand is obtained by using 1,2-cyclohexanediamine as a raw material, the organometallic complex of the present invention can be obtained with high yield. This is especially because the yield in synthesizing the ligand represented by the synthesis scheme (b-1) becomes high by using 1,2-cyclohexanediamine. Here, 1,2-cyclohexanediamine may be either a cis form or a trans form. Alternatively, it may be 1,2-cyclohexanediamine which has optical activity or 1,2-cyclohexanediamine which does not have optical activity.

In the synthesis scheme (b-1), each of $R^{51}$ to $R^{54}$ uses α-diketone represented by any one of an ethyl group, an isopropyl group, a sec-butyl group, or an ethoxy group as a raw material, and accordingly, other organometallic complexes of the present invention different from the organometallic complexes represented by the structural formulas (26) to (30) can be obtained. Also, by using salt containing platinum such as tetrachloro platinum potassium instead of iridium(III) chloride hydrochloride hydrate, an organometallic complex of the present invention containing platinum as its central metal can be obtained. Also, by using a ligand such as picoline acid, dimethyl malonate, salicyl aldehyde, salicylidene amine, or tetrapyrazolato boronate instead of acetylacetone, an organometallic complexes of the present invention containing ligands as represented by structural formulas (2) to (7) can also be obtained.

[Organometallic Complexes Represented by Structural Formulas (31) to (34)]

An organometallic complex of the present invention represented by any one of structural formulas (31) to (34) is obtained by a synthesis method as represented by following synthesis schemes (c-1) to (c-3). As shown in the synthesis scheme (c-1), α-diketone and 1,2-cyclohexanediamine are dehydrated and condensed, and thereafter, dehydrogenated using iron chloride (III) or the like, and accordingly, a ligand including a skeleton of tetrahydroquinoxaline is synthesized. Thereafter, the synthesized ligand is mixed with iridium(III) chloride hydrochloride hydrate and coordinated with iridium as represented by the synthesis scheme (c-2). As represented by the synthesis scheme (c-3), a monoanionic ligand is coordinated with iridium, and a dinuclear complex is synthesized. Furthermore, as represented by the synthesis scheme (c-3), the dinuclear complex which is synthesized previously and a monoanionic ligand such as acetylacetone or pocoline acid are reacted, and the monoanionic ligand is coordinated with iridium; accordingly, the organometallic complex of the present invention can be obtained.

(c-1)
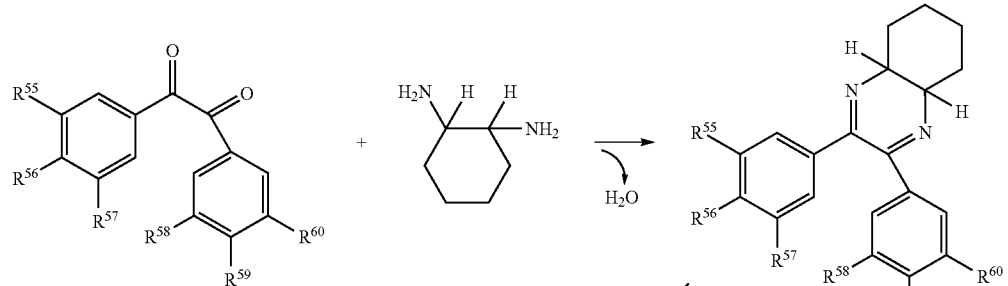
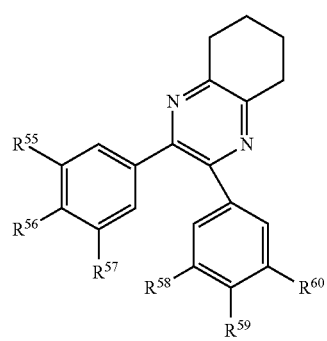
(c-2)
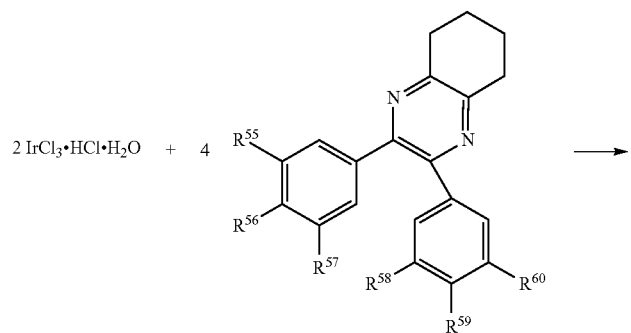
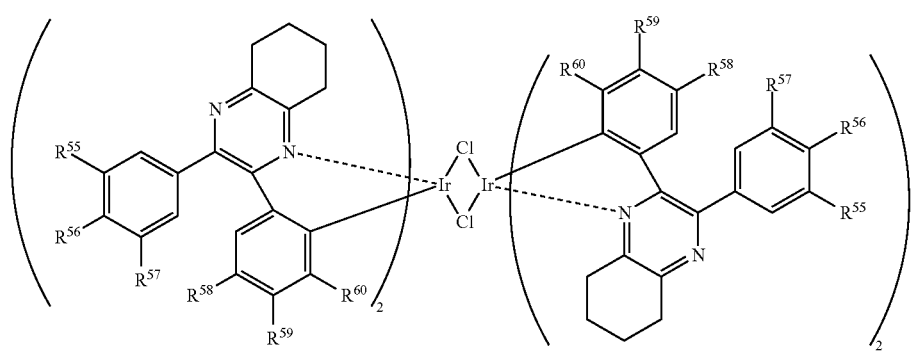

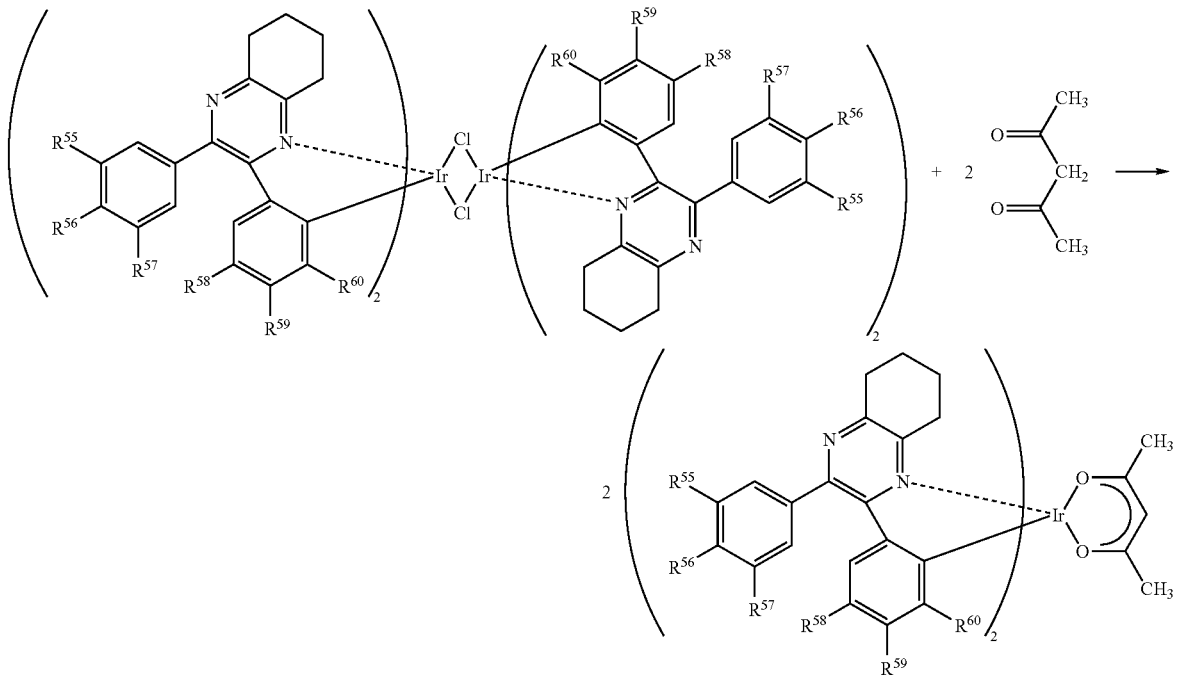

Here, in the synthesis schemes (c-1) to (c-3), each of $R^{55}$ to $R^{60}$ represents any one of a methyl group, a fluoro group, —$CF_3$, a methoxy group, and a phenyl group. L represents acetylacetone. Note that α-diketone which is used for a reaction in the synthesis scheme (c-1) can be obtained by a reaction of Grignard reagent of benzene, in which the third, fourth, and fifth positions are substituted by a methyl group, a fluoro group, —$CF_3$, and a methoxy group, with 1,4-dimethylpiperazine-2,3-dione.

A synthesis method of the organometallic complex of the present invention is not limited to the method represented by the synthesis schemes (c-1) to (c-3). However, as in the synthesis method of this mode, by applying the synthesis method including a step in which a ligand is obtained by using 1,2-cyclohexanediamine as a raw material, the organometallic complex of the present invention can be obtained with high yield. This is especially because the yield in synthesizing the ligand represented by the synthesis scheme (c-1) becomes high by using 1,2-cyclohexanediamine. Here, 1,2-cyclohexanediamine may be either a cis form or a trans form. Alternatively, it may be 1,2-cyclohexanediamine which has optical activity or 1,2-cyclohexanediamine which does not have optical activity.

In the synthesis scheme (c-1), each of $R^{55}$ to $R^{60}$ uses α-diketone represented by any one of an ethyl group, an isopropyl group, a sec-butyl group, and an ethoxy group as a raw material, and accordingly, other organometallic complexes of the present invention different from the organometallic complexes represented by the structural formulas (31) to (34) can be obtained. Also, by using salt containing platinum such as potassium tetrachloro platinate instead of iridium(III) chloride hydrochloride hydrate, an organometallic complex of the present invention containing platinum as its central metal can be obtained. Also, by using a ligand such as picoline acid, dimethyl malonate, salicyl aldehyde, salicylidene amine, or tetrapyrazolato bolonate instead of acetylacetone, organometallic complexes of the present invention containing ligands as represented by structural formulas (2) to (7) can be obtained.

Embodiment Mode 3

In this embodiment mode, a mode of a light-emitting element using the organometallic complex according to Embodiment Modes 1 and 2 will be described with reference to FIG. 1.

FIG. 1 shows a light-emitting element including a light-emitting layer 113 between a first electrode 101 and a second electrode 102. The light-emitting layer 113 contains an organometallic complex including a structure represented by any one of general formulas (1), (3), (5), (7), (9) and (11), or an organometallic complex represented by any one of general formulas (2), (4), (6), (8), (10), (12) and (13).

In addition to the light-emitting layer 113, a hole injecting layer 111, a hole transporting layer 112, an electron transporting layer 114, an electron injecting layer 115, a blocking layer 121, and the like are provided between the first electrode 101 and the second electrode 102. These layers are stacked so that holes are injected from the first electrode 101 and electrons are injected from the second electrode 102, when voltage is applied to make electric potential of the first electrode 101 higher than that of the second electrode 102.

In such a light-emitting element, holes injected from the first electrode 101 and electrons injected from the second electrode 102 are recombined in the light-emitting layer 113, and the organometallic complex becomes an excited state. The excited organometallic complex of the present invention emits light in returning to a ground state. As described above, the organometallic complex of the present invention functions as a light-emitting substance.

Here, the light-emitting layer 113 is a layer containing the organometallic complex of the present invention. The light-emitting layer 113 may be a layer formed by using only the organometallic complex of the present invention; however, in a case where a concentration quenching phenomenon is generated, the light-emitting layer 113 is preferably a layer in which a light-emitting substance is mixed to be dispersed in a layer formed by using a substance including a larger energy gap than that of a light-emitting substance. The organometallic complex of the present invention is dispersed and contained in the light-emitting layer 113, and accordingly, an optical quenching due to the concentration, that is to say a concentration quenching phenomenon, can be prevented. Here, the energy gap indicates an energy gap between a LUMO level and a HOMO level.

A material which is used for making the organometallic complex of the present invention in a dispersed state is not particularly limited; however, in addition to a compound including a skeleton of aryl amine such as 2,3-bis(4-diphenylaminophenyl)quinoxaline (abbreviation: TPAQn) or 4,4'-bis[N-(1-naphtyl)-N-phenylamino]biphenyl (abbreviation NPB), a carbazole derivative such as 4,4'-di(N-carbazolyl) biphenyl (abbreviation: CBP) or 4,4',4"-tri(N-carbazolyl) triphenylamine (abbreviation: TCTA); a metal complex such as bis[2-(2-hydroxyphenyl)pyridinato]zinc (abbreviation: Znpp$_2$) or bis[2-(2-hydroxyphenyl)benzoxazolato]zinc (abbreviation: Zn(BOX)$_2$), or the like is preferably used. One or two or more of these materials are selected to be mixed so that the organometallic complex of the present invention becomes a dispersed state. As described above, the layer containing a plurality of compounds can be formed by a co-evaporation method. Here, the co-evaporation method is defined to an evaporation method by which respective raw materials are vaporized from a plurality of evaporation sources provided in one processing chamber, and the vaporized raw materials are mixed in a gaseous state to be deposited over a processed substance.

The first electrode 101 and the second electrode 102 are not particularly limited. In addition to indium tin oxide (ITO), indium tin oxide containing silicon oxide, or indium oxide containing 2 to 20 wt % of zinc oxide, gold (Au); platinum (Pt); nickel (Ni); tungsten (W); chromium (Cr); molybdenum (Mo); iron (Fe); cobalt (Co); copper (Cu); palladium (Pd); and the like can be used. Also, in addition to aluminum, alloy of magnesium and silver; alloy of aluminum and lithium; or the like can also be used for forming the first electrode 101. Further, a forming method of the first electrode 101 and the second electrode 102 is not particularly limited. For example, a sputtering method, an evaporation method, or the like can be used. In order to take out light emission to the outside, one or both of the first electrode 101 and the second electrode 102 is/are preferably formed by using indium tin oxide or the like, or by depositing silver, aluminum or the like to have a thickness of several nanometers to several tens nanometers.

The hole transporting layer 112 may also be provided between the first electrode 101 and the light-emitting layer 113, as shown in FIG. 1. Here, the hole transporting layer refers to a layer having a function of transporting holes injected from the first electrode 101 to the light-emitting layer 113. As described above, by providing the hole transporting layer 112, a distance between the first electrode 101 and the light-emitting layer 113 can be larger; accordingly, optical quenching due to metal contained in the first electrode 101 can be prevented. The hole transporting layer is preferably formed by using a material having a high hole transporting property, especially, a material having hole mobility of $1\times10^{-6}$ cm$^2$/Vs or more. Note that a material having a high hole transporting property refers to a material having higher mobility of holes than that of electrons and having a ratio value of hole mobility to electron mobility (=hole mobility/electron mobility) of more than 100. As a specific example of a material which can be used for forming the hole transporting layer 112, 4,4'-bis[N-(1-naphtyl)-N-phenylamino]biphenyl (abbreviation: NPB), 4,4'-bis[N-(3-methylphenyl)-N-phenylamino]biphenyl (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4"-tri(N-carbazolyl)triphenylamine (abbreviation: TCTA), phthalocyanine (abbreviation: H$_2$Pc), copper phthalocyanine (abbreviation: CuPc), vanadylphthalocyanine (abbreviation: VOPc), or the like can be given. Also, the hole transporting layer 112 can be formed to have a multilayer structure formed by stacking two or more of layers formed using the above materials.

The electron transporting layer 114 may also be provided between the second electrode 102 and the light-emitting layer 113, as shown in FIG. 1. Here, the electron transporting layer refers to a layer having a function of transporting electrons injected from the second electrode 102 to the light-emitting layer 113. As described above, by providing the electron transporting layer 114, a distance between the second electrode 102 and the light-emitting layer 113 can be larger; accordingly, optical quenching due to metal contained in the second electrode 102 can be prevented. The electron transporting layer is preferably formed using a material having a high electron transporting property, especially, a material having electron mobility of $1\times10^{-6}$ cm$^2$/Vs or higher. Note that a material having a high electron transporting property refers to a material having higher mobility of electrons than that of holes and having a ratio value of electron mobility to hole mobility (=electron mobility/hole mobility) of more than 100. As a specific example of a material for forming the electron transporting layer 114, in addition to a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]-quinolinato)beryllium (abbreviation: BeBq$_2$), bis(2-methyl-8-quinolinolato)-4-phenylphenolato-aluminum (abbreviation: BAlq), bis[2-(2-hydroxyphenyl)benzoxazolato]zinc (abbreviation: Zn(BOX)$_2$), bis[2-(2-hydroxyphenyl)benzothiazolato]zinc (abbreviation: Zn(BTZ)$_2$), 2-(4-biphenylyl)-5-(4-tert-buthylphenyl)-1,3,4-oxadiazole (abbreviation: PBD), 1,3-bis[5-(p-tert-buthylphenyl)-1,3,4-oxadiazol-2-yl]benzene (abbreviation: OXD-7), 3-(4-tert-buthylphenyl)-4-phenyl-5-(4-biphenylyl)-1,2,4-triazole (abbreviation: TAZ), 3-(4-tert-buthylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4-bis(5-methylbenzoxazol-2-yl) stilbene (abbreviation: BzOs), or the like can be given. Also, the electron transporting layer 114 can be formed to have a multilayer structure formed by stacking two or more of layers formed using the above materials.

In addition to the above materials, each of the hole transporting layer 112 and the electron transporting layer 114 may be formed using a bipolar substance. A bipolar substance refers to a following substance: when carrier mobility of either electrons or holes is compared with other carrier mobility, a value of a ratio of one carrier mobility to the other carrier mobility is 100 or less, preferably 10 or less. As the bipolar substance, for example, TPAQn, 2,3-bis{-4-[N-(1-naphthyl)-N-phenylamino]phenyl}-dibenzo[f,h]quinoxaline (abbreviation: NPADiBzQn), and the like can be given. It is especially preferable to use a substance of which hole and electron mobility are each $1\times10^{-6}$ cm$^2$/Vs or more among the bipolar substances. Also, the hole transporting layer 112 and the electron transporting layer 114 may be formed using the same bipolar substance.

Furthermore, the hole injecting layer 111 may be provided between the first electrode 101 and the hole transporting layer 112, as shown in FIG. 1. The hole injecting layer 111 refers to a layer having a function of assisting holes to be injected from the first electrode 101 to the hole transporting layer 112. By providing the hole injecting layer 111, a difference in ionization potential between the first electrode 101 and the hole transporting layer 112 is relieved, and holes are easily injected. The hole injecting layer 111 is preferably formed by a material having smaller ionization potential than that of a material which forms the hole transporting layer 112 and larger ionization potential than that of a material which forms the first electrode 101, or a material having an energy band which bends when the material is provided as a thin film having a thickness of 1 to 2 nm between the hole transporting layer 112 and the first electrode 101. As a specific example of a material which can be used for forming the hole injecting layer 111, a phthalocyanine derivative such as phthalocyanine (abbreviation: H$_2$Pc) or copper phthalocyanine (CuPc); a high molecular compound such as poly(ethylenedioxythiophene)/poly(styrenesulfonic acid) solution (PEDOT/PSS); or the like can be given. In other words, the hole injecting layer 111 can be formed by selecting a material so that ionization potential of the hole injecting layer 111 is relatively smaller than that of the hole transporting layer 112. Further, in a case where the hole injecting layer 111 is provided, the first electrode 101 is preferably formed using a material having a high work function, such as indium tin oxide.

The electron injecting layer 115 may be provided between the second electrode 102 and the electron transporting layer 114, as shown in FIG. 1. Here, the electron injecting layer 115 refers to a layer having a function of assisting electrons to be injected from the second electrode 102 to the electron transporting layer 114. By providing the electron injecting layer 115, a difference in electron affinity between the second electrode 102 and the electron transporting layer 114 can be relieved, and electrons are easily injected. The electron injecting layer 115 is preferably formed using a material having larger electron affinity than that of a material which forms the electron transporting layer 114 and smaller electron affinity than that of a material which forms the second electrode 102, or a material having an energy band which bends when the material is provided as a thin film of having a thickness of 1 to 2 nm between the electron transporting layer 114 and the second electrode 102. As a specific example of a material which can be used for forming the electron injecting layer 115, an inorganic material such as alkali metal, alkaline earth metal, fluoride of alkali metal, fluoride of alkaline earth metal, oxide of alkali metal, or oxide of alkaline earth metal are given. In addition to the inorganic material, a material which can be used for forming the electron transporting layer 114 such as BPhen, BCP, p-EtTAZ, TAZ, or BzOs can also be used as a material for forming the electron transporting layer 114 by selecting a material of which electron affinity is larger than that of a material for forming the electron transporting layer 114 among these materials. In other words, the electron injecting layer 115 can be formed by selecting a material so that electron affinity of the electron injecting layer 115 is relatively larger than that of the electron transporting layer 114. Further, in a case where the electron injecting layer 115 is provided, the first electrode 101 is preferably formed using a material having a low work function, such as aluminum.

As for the above light-emitting element of the present invention, each of the hole injecting layer 111, the hole transporting layer 112, the light-emitting layer 113, the electron transporting layer 114, and the electron injecting layer 115 may be formed by any one of an evaporation method, an ink jet method, a coating method, and the like. Also, the first electrode 101 or the second electrode 102 may be formed by any one of a sputtering method, an evaporation method, and the like.

A hole generating layer may also be provided instead of the hole injecting layer 111, or an electron generating layer may be provided instead of the electron injecting layer 115. Providing the hole generating layer or the electron generating layer makes it possible to manufacture a light-emitting element in which voltage is scarcely increased depending on a thickness of the layer.

Here, the hole generating layer refers to a layer which generates holes. The hole generating layer can be formed by mixing at least one material selected from materials having higher mobility of holes than that of electrons and a material showing an electron accepting property with respect to a material having higher mobility of holes than that of electrons, or mixing at least one material selected from bipolar substances and a material showing an electron accepting property with respect to the bipolar substance. Here, as a material having higher mobility of holes than that of electrons, materials similar to the materials which can be used for forming the hole transporting layer 112 can be used. As the bipolar substance, the above material such as TPAQn, can be used. In particular, a material having a skeleton of triphenylamine is used among the materials having higher mobility of holes than that of electrons and the bipolar substances. Holes are easily generated by using the material having a skeleton of triphenylamine. Also, as the material showing an electron accepting property, metal oxide such as molybdenum oxide, vanadium oxide, ruthenium oxide, or rhenium oxide is preferably used.

The electron generating layer refers to a layer which generates electrons. The electron generating layer can be formed by mixing a material having higher mobility of electrons than that of holes and a material showing an electron donating property with respect to a material having higher mobility of electrons than that of holes, or mixing at least one material selected from bipolar substances and a material showing an electron donating property with respect to the bipolar substance. Here, as a material having higher mobility of electrons than that of holes, materials similar to the materials which can be used for forming the electron transporting layer 114 can be used. As the bipolar substance, the above mentioned bipolar material such as TPAQn can be used. As a material showing an electron donating property, a material selected from alkali metal and alkaline earth metal, specifically, lithium (Li), calcium (Ca), sodium (Na), kalium (Ka), magnesium (Mg), or the like can be used. At least one material selected from alkali metal oxide, alkaline earth metal oxide, alkali metal nitride, alkaline earth metal nitride or the like, specifically, lithium oxide (Li$_2$O), calcium oxide (CaO), sodium oxide (Na$_2$O), kalium oxide (K$_2$O), magnesium oxide (MgO), or the like can be used as a material showing an electron donating property. Also, at least one material selected from alkali metal fluoride and alkaline earth metal fluoride, specifically, lithium fluoride (LiF), cesium fluoride (CsF), calcium fluoride (CaF$_2$), or the like can be used as a material showing an electron donating property. Also, at least one material selected from alkali metal nitride and alkaline earth metal nitride, specifically, calcium nitride, magnesium nitride, or the like can be used as a material showing an electron donating property.

Furthermore, a blocking layer may also be provided between the light-emitting layer 113 and the hole transporting layer 112, or between the light-emitting layer 113 and the electron transporting layer 114. The blocking layer refers to a layer having a function of preventing holes injected from the first electrode 101 or electrons injected from the second electrode 102 from going through the light-emitting layer to enter the other electrode, or a function of preventing excited energy generated in the light-emitting layer from moving from the light-emitting layer to the other layer, in addition to a function of transporting holes or electrons to the light-emitting layer 113. As shown in FIG. 1, the blocking layer 121 which is provided between the light-emitting layer 113 and the electron transporting layer 114 and has a function of preventing holes from going through is specifically referred to as a hole blocking layer. Providing the blocking layer makes it possible to suppress a decrease in recombination efficiency due to carriers that go through and increase light-emitting efficiency. In addition, providing the blocking layer makes it possible to decrease light emission by a substance different from a light-emitting substance, for example, a material or the like which forms the electron transporting layer which emits light due to a transport of excited energy despite its intention.

In the light-emitting element of the present invention as described above, it is optional whether or not layers different from the light-emitting layer, specifically, the hole injecting layer, the hole transporting layer, the electron transporting layer, the electron injecting layer, and the like are provided, and practitioners of the present invention may appropriately select. However, in a case where the hole transporting layer and the electron transporting layer are provided, effect to decrease optical quenching due to metal contained in the electrode, the hole injecting layer, the electron injecting layer, or the like is obtained. Also, by providing the electron injecting layer, the hole injecting layer, or the like, effect to inject electrons or holes from the electrode efficiently is obtained.

The above described light-emitting element of the present invention uses the organometallic complex of the present invention, for example, the structural formulas of which are listed in Embodiment Mode 1, as a light-emitting substance; therefore, internal quantum efficiency is high, light-emitting efficiency, specifically, luminance for unit voltage or luminance for unit current density is favorable. Also, in a case where the organometallic complex of the present invention is contained in the light-emitting element of the present invention as a light-emitting substance, effect to reduce cost of raw materials used for manufacturing the light-emitting element can be obtained. This is because the organometallic complex of the present invention can be synthesized with high yield as described in Embodiment Mode 2, in other words, an organometallic complex with reduced manufacturing cost can be obtained.

Embodiment Mode 4

A light-emitting element of the present invention in which an organometallic complex of the present invention is used as a light-emitting substance can emit light efficiently; therefore, a light-emitting device in which the light-emitting element of the present invention is used as a pixel can be operated with low power consumption. This is because, as described in Embodiment Mode 3, the light-emitting element of the present invention has favorable luminance for unit voltage or favorable luminance for unit current density; accordingly, electric power (=current×voltage) which is necessary for light emission of specific luminance can be decreased by using the light-emitting element of the present invention as a pixel. Also, the light-emitting device of the present invention, in which a light-emitting element manufactured at low cost by using the organometallic complex of the present invention, is manufactured at low cost and is inexpensive. In this embodiment mode, a circuit structure and a driving method of a light-emitting device having a display function will be described with reference to FIGS. 2, 3, 4 and 5.

Figure 2:
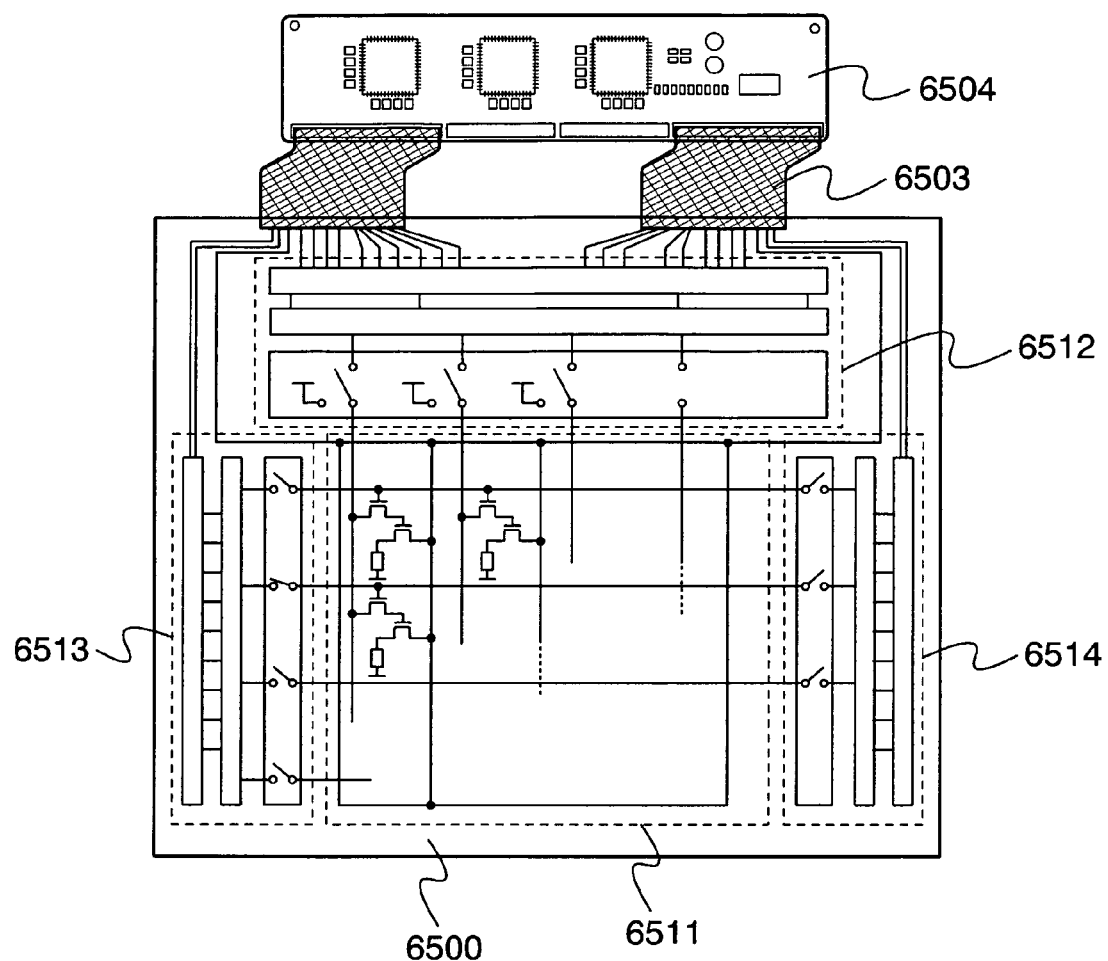
FIG. 2 is a view explaining a light-emitting device to which the present invention is applied.

FIG. 2 is a schematic top view of a light-emitting device to which the present invention is applied (a light-emitting device according to this embodiment mode). In FIG. 2, a pixel portion 6511, a source signal line driver circuit 6512, a writing gate signal line driver circuit 6513, and an erasing gate signal line driver circuit 6514 are provided over a substrate 6500. Each of the source signal line driver circuit 6512, the writing gate signal line driver circuit 6513, and the erasing gate signal line driver circuit 6514 is connected to an FPC (flexible printed circuit) 6503 which is an external input terminal through wirings. Each of the source signal line driver circuit 6512, the writing gate signal line driver circuit 6513, and the erasing gate signal line driver circuit 6514 receives a video signal, a clock signal, a start signal, a reset signal, or the like from the FPC 6503. Also, a printed wiring board (PWB) 6504 is attached to the FPC 6503. Note that the driver circuit portion is not necessarily provided over the same substrate as the pixel portion 6511 as described above. For example, the driver circuit portion may be provided outside the substrate by using a TCP or the like where an IC chip is mounted over an FPC having a wiring pattern.

In the pixel portion 6511, a plurality of source signal lines extending in columns are aligned in rows. Current supply lines are aligned in rows. A plurality of gate signal lines extending in rows are aligned in columns in the pixel portion 6511. In addition, a plurality of sets of circuits each including a light-emitting element are aligned in the pixel portion 6511.

Figure 3:
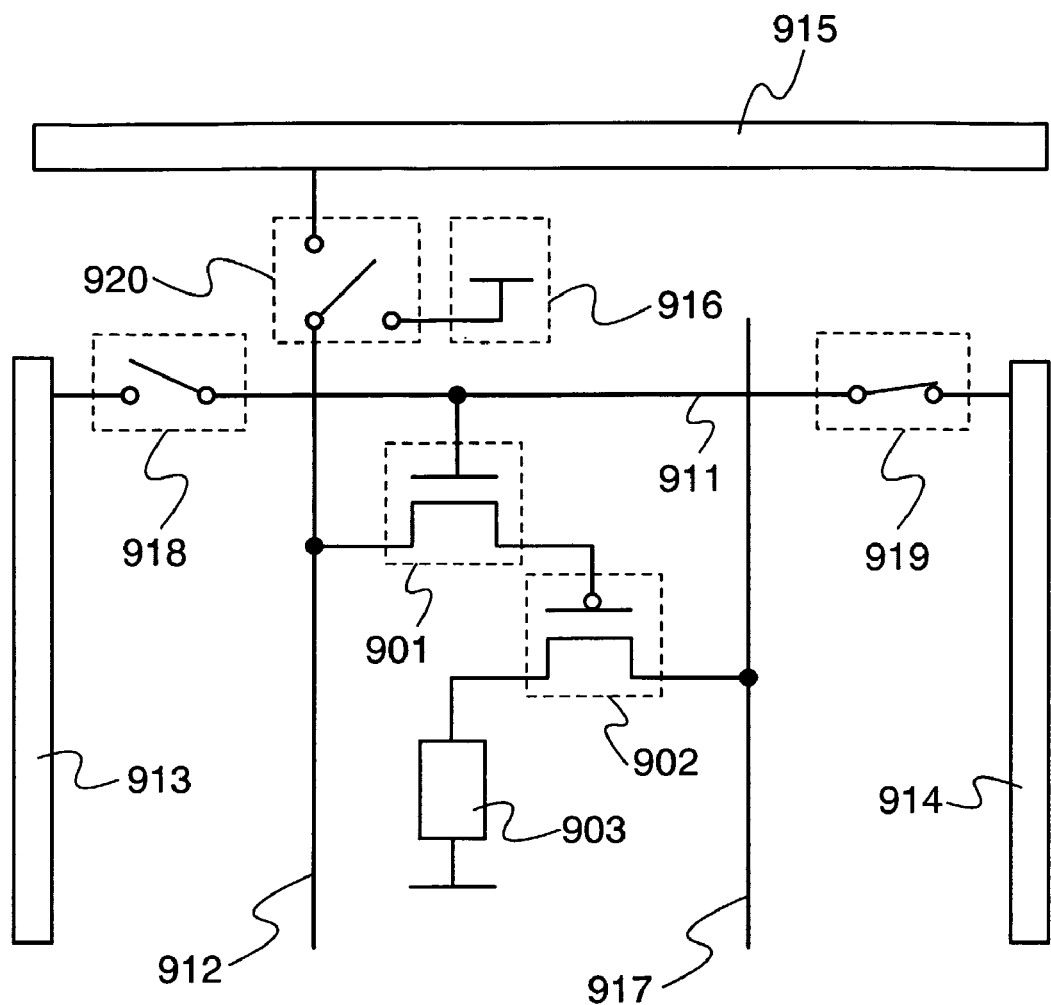
FIG. 3 is a diagram explaining a circuit included in a light-emitting device to which the present invention is applied.

FIG. 3 is a diagram showing a circuit for operating one pixel. The circuit shown in FIG. 3 includes a first transistor 901, a second transistor 902 and a light-emitting element 903.

Each of the first transistor 901 and the second transistor 902 is a three-terminal element including a gate electrode, a drain region and a source region, and includes a channel region between the drain region and the source region. Here, the source region and the drain region are switched depending on a structure, an operational condition, and the like of the transistor; therefore, it is difficult to determine which region functions as a source region or a drain region. Consequently, in this embodiment mode, each of regions functioning as a source region or a drain region is denoted as a first electrode of a transistor or a second electrode of a transistor.

A gate signal line 911 and a writing gate signal line driver circuit 913 are provided so as to be electrically connected or disconnected to each other by a switch 918. The gate signal line 911 and an erasing gate signal line driver circuit 914 are provided so as to be electrically connected or disconnected to each other by a switch 919. A source signal line 912 is provided so as to be electrically connected to either a source signal line driver circuit 915 or a power source 916 by a switch 920. A gate of the first transistor 901 is electrically connected to the gate signal line 911. Also, a first electrode of the first transistor is electrically connected to the source signal line 912, and the second electrode is electrically connected to a gate electrode of the second transistor 902. A first electrode of the second transistor 902 is electrically connected to a current supply line 917, and a second electrode is electrically connected to one electrode included in the light-emitting element 903. Note that the switch 918 may be included in the writing gate signal line driver circuit 913. Also, the switch 919 may be included in the erasing gate signal line driver circuit 914. Furthermore, the switch 920 may be included in the source signal line driver circuit 915.

Figure 4:
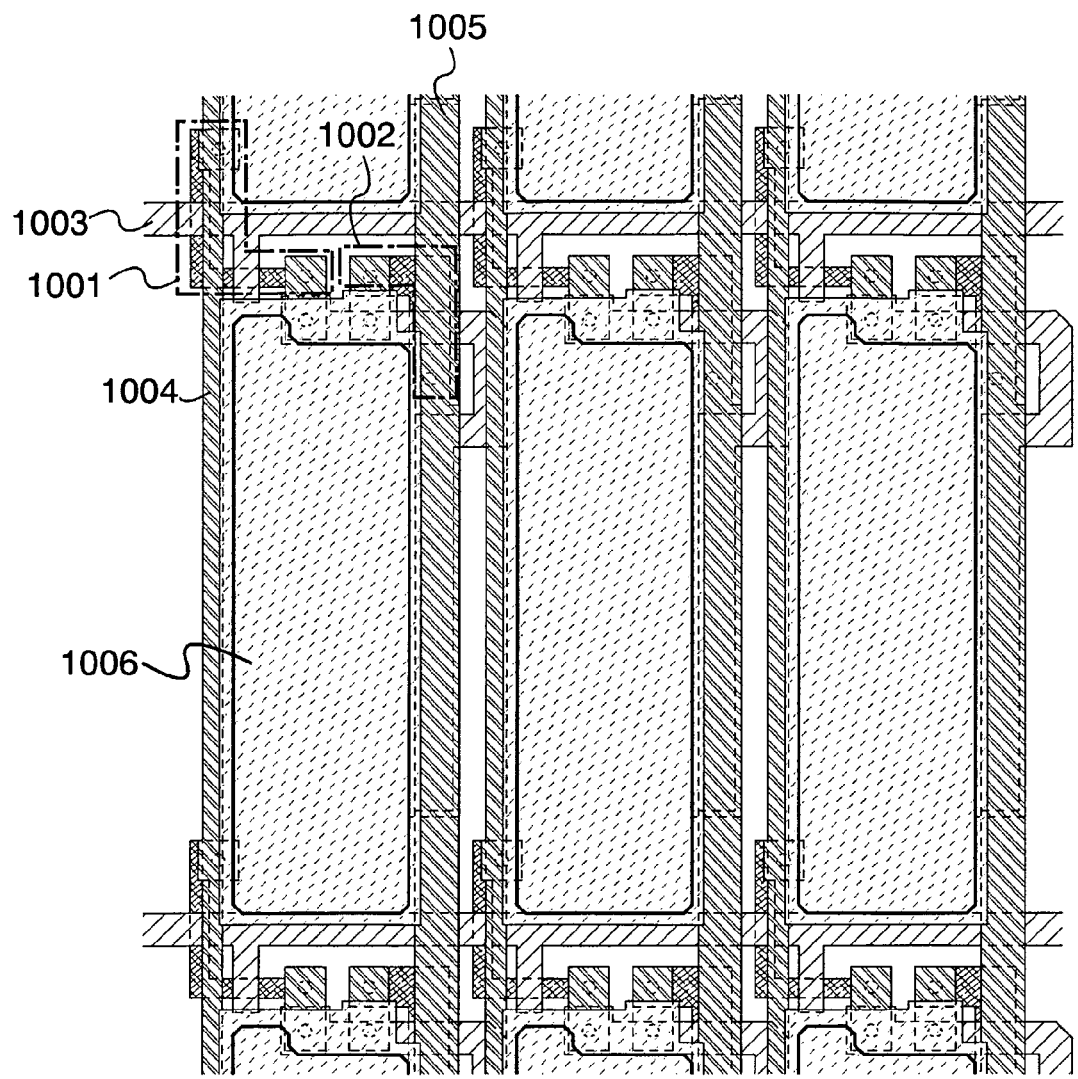
FIG. 4 is a top view of a light-emitting device to which the present invention is applied.

The arrangement of the transistors, the light-emitting element, and the like is not particularly limited; however, the arrangement shown in a top view of FIG. 4 can be employed. In FIG. 4, a first electrode of a first transistor 1001 is connected to a source signal line 1004, and a second electrode is connected to a gate electrode of a second transistor 1002. A first electrode of the second transistor is connected to a current supply line 1005, and a second electrode is connected to an electrode 1006 of a light-emitting element. A part of a gate signal line 1003 functions as a gate electrode of the first transistor 1001.

Figure 5:
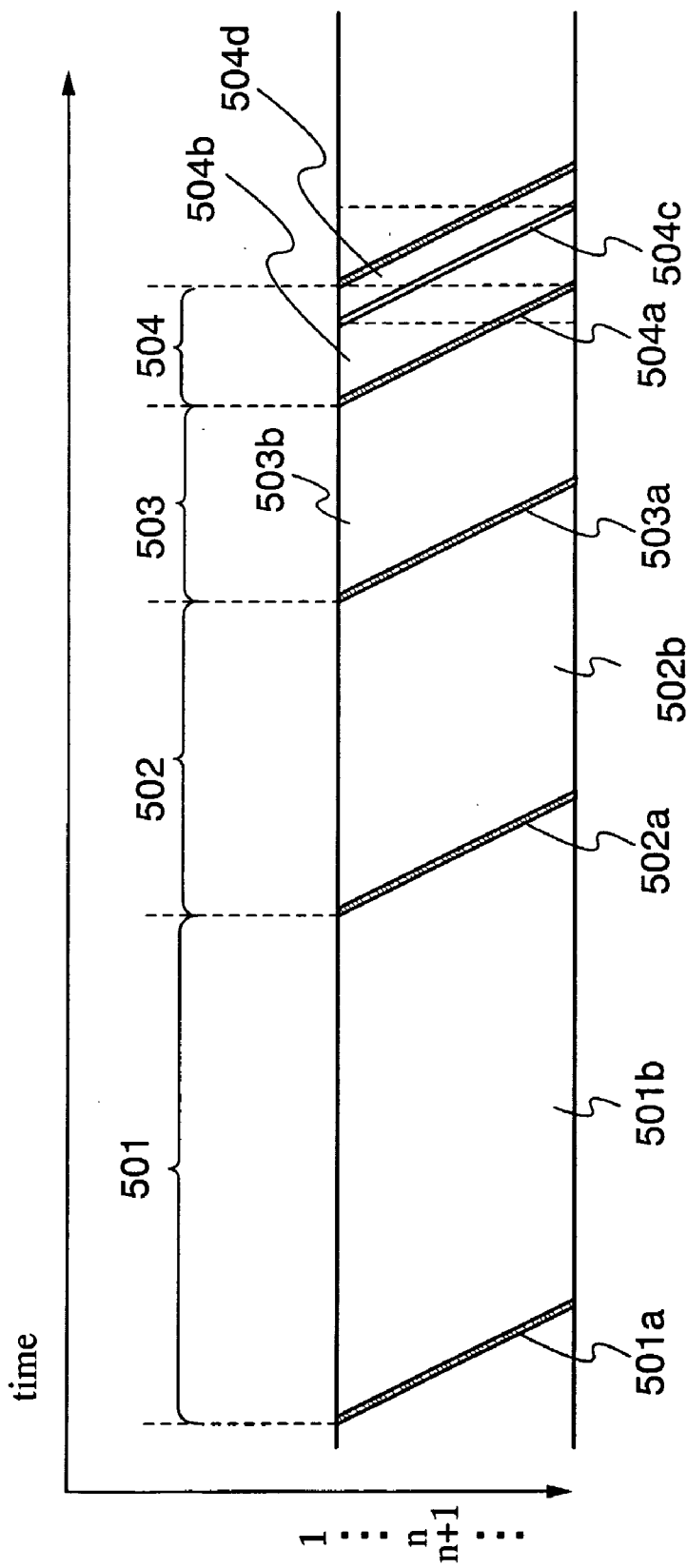
FIG. 5 is a view explaining a frame operation of a light-emitting device to which the present invention is applied.

Next, a driving method is described. FIG. 5 is a diagram explaining an operation of a frame with time passage. In FIG. 5, a horizontal direction indicates time passage while a longitudinal direction indicates the number of scanning stages of a gate signal line.

When an image is displayed by using the light-emitting device of the present invention, a rewriting operation of a screen is carried out repeatedly during a displaying period. The number of the rewriting operations is not particularly limited. However, the rewriting operation is preferably performed at least about 60 times a second so that a person who watches a displayed image does not detect flicker. Here, a period of performing the rewriting operation of one image (one frame) is referred to as one frame period.

As shown in FIG. 5, one frame is divided into four sub-frames 501, 502, 503, and 504 including writing periods 501a, 502a, 503a, and 504a, and holding periods 501b, 502b, 503b, and 504b. A light-emitting element to which a signal for emitting light is given is in a light-emitting state in the holding periods. The length ratio of the holding periods in the respective sub-frames satisfies the first sub-frame 501:the second sub-frame 502:the third sub-frame 503:the fourth sub-frame 504=$2^3:2^2:2^1:2^0$=8:4:2:1. This makes it possible to exhibit 4-bit gray scale. However, the number of bits and the number of gray scales are not limited to those described here. For example, one frame may be provided with eight sub-frames so as to achieve 8-bit gray scale.

An operation in one frame is described. First, in the sub-frame 501, a writing operation is sequentially performed in first to last rows. Therefore, the starting time of the writing period is different depending on each row. The holding period 501b sequentially starts from the row in which the writing period 501a is terminated. In the holding period, a light-emitting element to which a signal for emitting light is given is in a light-emitting state. The next sub-frame 502 sequentially starts from the row in which the holding period 501b is terminated, and a writing operation is sequentially performed in the first to last rows in the same manner as the sub-frame 501. Operations as described above are repeatedly carried out to the holding period 504b of the sub-frame 504, and an operation in the sub-frame 504 is terminated. After terminating the operation in the sub-frame 504, an operation in the next frame starts. Accordingly, the sum of the light-emitting time in the respective sub-frames corresponds to the light-emitting time of each light-emitting element in one frame. By changing the light-emitting time for each light-emitting element and combining such light-emitting elements variously within one pixel, various display colors with different brightness and different chromaticity can be obtained.

As in the sub-frame 504, when the holding period in the row, in which the writing is already terminated and the holding period is started before the writing to the last row is terminated, is intended to be forcibly terminated, an erasing period 504c is preferably provided after the holding period 504b to control the row to be forcibly in a non-light-emitting state. The row in which light emission is forcibly stopped does not emit light for a certain period (this period is referred to as a non-light-emitting period 504d). Right after terminating the writing period of the last row, a writing period in a next sub-frame (or a next frame) starts sequentially from a first row. This can prevent the writing period in the sub-frame 504 from overlapping with the writing period in the next sub-frame.

Although the sub-frames 501 to 504 are arranged in order from the longer holding period in this mode, they are not necessarily arranged in this order. For example, the sub-frames may be arranged in order from the shorter holding period. Alternatively, the longer holding period and the shorter holding period may be arranged randomly. Also, the sub-frame may further be divided into a plurality of frames. That is, the gate signal line may be scanned a plurality of times while the same video signals are given.

Here, an operation of the circuit shown in FIG. 3 in the writing period and the erasing period is described.

First, an operation in the writing period is described. In the writing period, the gate signal line 911 in the n-th row (n is a natural number) is electrically connected to the writing gate signal line driver circuit 913 through the switch 918, and is disconnected to the erasing gate signal line driver circuit 914. Also, the source signal line 912 is electrically connected to the source signal line driver circuit through the switch 920. Here, a signal is inputted to the gate of the first transistor 901 which is connected to the gate signal line 911 in the n-th row (n is a natural number), and the first transistor 901 is turned on. At this time, video signals are inputted to the source signal lines in the first column to the last column concurrently. Further, the video signals inputted from the source signal lines 912 in the respective columns are independent from each other. The video signals inputted from the source signal line 912 are inputted to the gate electrode of the second transistor 902 through the first transistor 901 which is connected to each of the source signal lines. At this time, whether the light-emitting element 903 emits light or not is determined depending on the signal inputted to the second transistor 902. For example, in a case where the second transistor 902 is a P-channel type, the light-emitting element 903 emits light by inputting a low level signal to the gate electrode of the second transistor 902. On the other hand, in a case where the second transistor 902 is an N-channel type, the light-emitting element 903 emits light by inputting a high level signal to the gate electrode of the second transistor 902.

Next, an operation in the erasing period is described. In the erasing period, the gate signal line 911 in the n-th row (n is a natural number) is electrically connected to the erasing gate signal line driver circuit 914 through the switch 919, and is disconnected to the writing gate signal line driver circuit 913. Also, the source signal line 912 is electrically connected to the power source 916 through the switch 920. Here, a signal is inputted to the gate of the first transistor 901 connected to the gate signal line 911 in the n-th row, and the first transistor 901 is turned on. At this time, erasing signals are inputted to the source signal lines from the first to the last columns concurrently. The erasing signals inputted from the source signal line 912 are inputted to the gate electrode of the second transistor 902 through the first transistor 901 which is connected to each of the source signal lines. At this time, supply of a current to the light-emitting element 903 from the current supply line 917 is blocked by the signals inputted to the second transistor 902. This makes the light-emitting element 903 emit no light forcibly. For example, in a case where the second transistor 902 is a P-channel type, the light-emitting element 903 does not emit light by inputting a high level signal to the gate electrode of the second transistor 902. On the other hand, in a case where the second transistor 902 is an N-channel type, the light-emitting element 903 does not emit light by inputting a low level signal to the gate electrode of the second transistor 902.

Further, in the erasing period, a signal for erasing is inputted to the n-th row by the operation described above. However, as described above, the n-th row may also be in the erasing period while another row (m-th row (m is a natural number)) is in the writing period. In this case, since a signal for erasing is necessary to be inputted to the n-th row and a signal for writing is necessary to be inputted to the m-th row by using the source signal line in the same column, an operation described below is preferably performed After the light-emitting element 903 in the n-th row becomes a non-light-emitting state by the above-described operation in the erasing period, the gate signal line 911 and the erasing gate signal line driver circuit 914 are immediately disconnected to each other, while the source signal line 912 is connected to the source signal line driver circuit 915 by turning on/off the switch 920. Then, the gate signal line 911 and the writing gate signal line driver circuit 913 are connected to each other, while the source signal line and the source signal line driver circuit 915 are connected to each other. A signal is selectively inputted to the signal line in the m-th row from the writing gate signal line driver circuit 913 and the first transistor is turned on, while signals for writing are inputted to the source signal lines in the first to the last columns from the source signal line driver circuit 915. By these signals, the light-emitting element in the m-th row emits light or emits no light.

After terminating the writing period in the m-th row as described above, the erasing period in the (n+1)-th row immediately starts. Therefore, the gate signal line 911 and the writing gate signal line driver circuit 913 are disconnected to each other, while the source signal line is connected to the power source 916 by turning on/off the switch 920. Moreover, the gate signal line 911 and the writing gate signal line driver circuit 913 are disconnected to each other, while the gate signal line 911 is connected to the erasing gate signal line driver circuit 914. A signal is selectively inputted to the gate signal line in the (n+1)-th row from the erasing gate signal line driver circuit 914 to input the signal for turning on the first transistor, while an erasing signal is inputted thereto from the power source 916. As described above, after the erasing period in the (n+1)-th row is terminated, the writing period in the (m+1)-th row immediately starts. Hereinafter, the erasing period and the writing period may be repeated to the erasing period of the last row in the same manner.

Although the writing period in the m-th row is provided between the erasing period in the n-th row and the erasing period in the (n+1)-th row is described in this embodiment mode, the present invention is not limited thereto. The writing period in the m-th row may be provided between the erasing period in the (n−1)-th row and the erasing period in the n-th row.

Furthermore, in this embodiment mode, in a case where the non-light-emitting period 504d is provided as in the subframe 504, an operation of disconnecting the erasing gate signal line driver circuit 914 with one gate signal line, while connecting the writing gate signal line driver circuit 913 and another gate signal line is performed repeatedly. This operation may also be performed in a frame in which a non-light-emitting period is not particularly provided.

Embodiment Mode 5

One mode of a sectional structure of a light-emitting device including a light-emitting element of the present invention will be described with reference to FIGS. 6A to 6C.

Figure 6A:
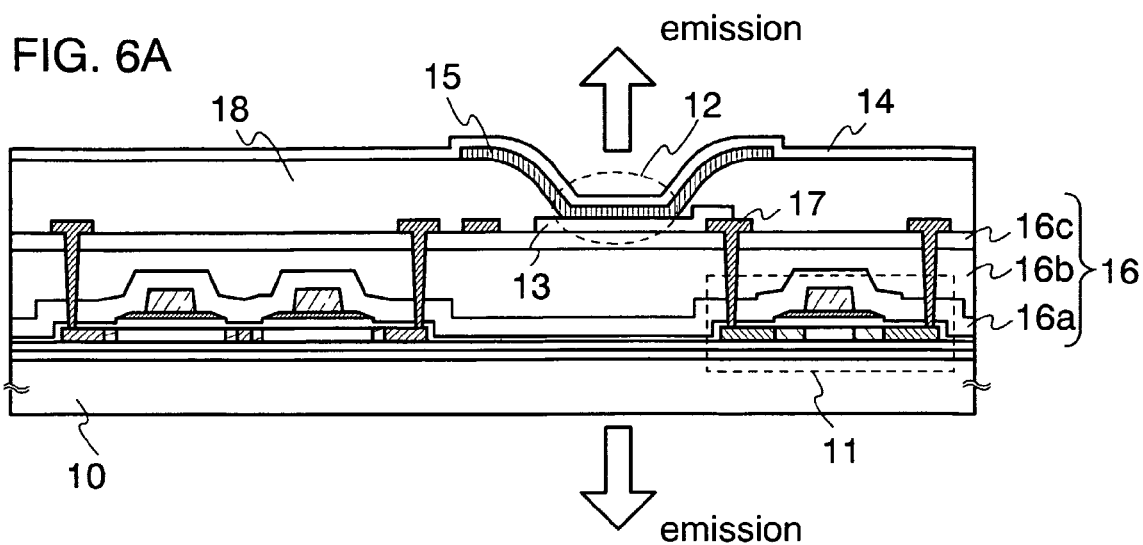
FIGS. 6A to 6C are cross-sectional views of a light-emitting device to which the present invention is applied.
Figure 6B:
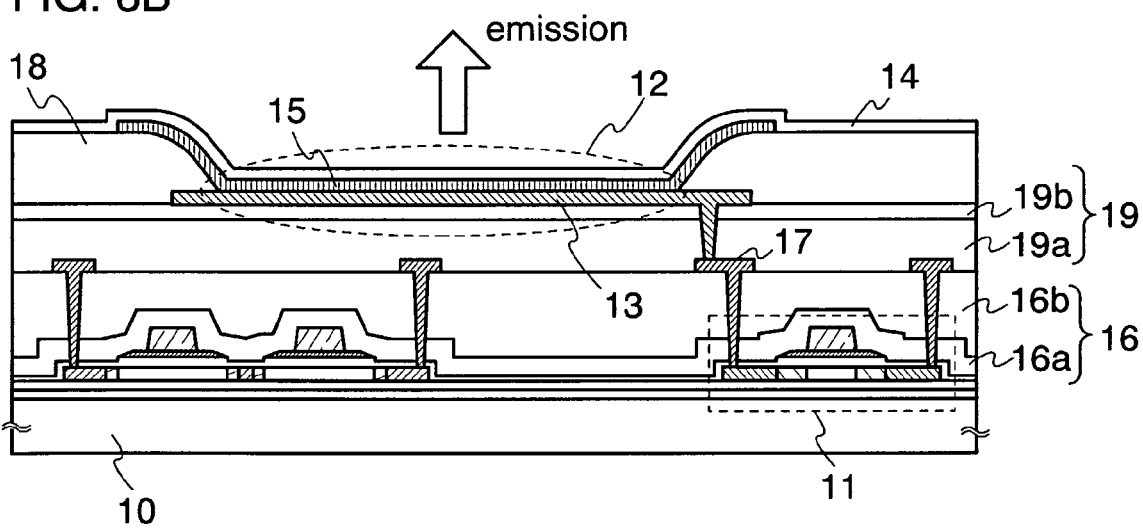
Figure 6C:
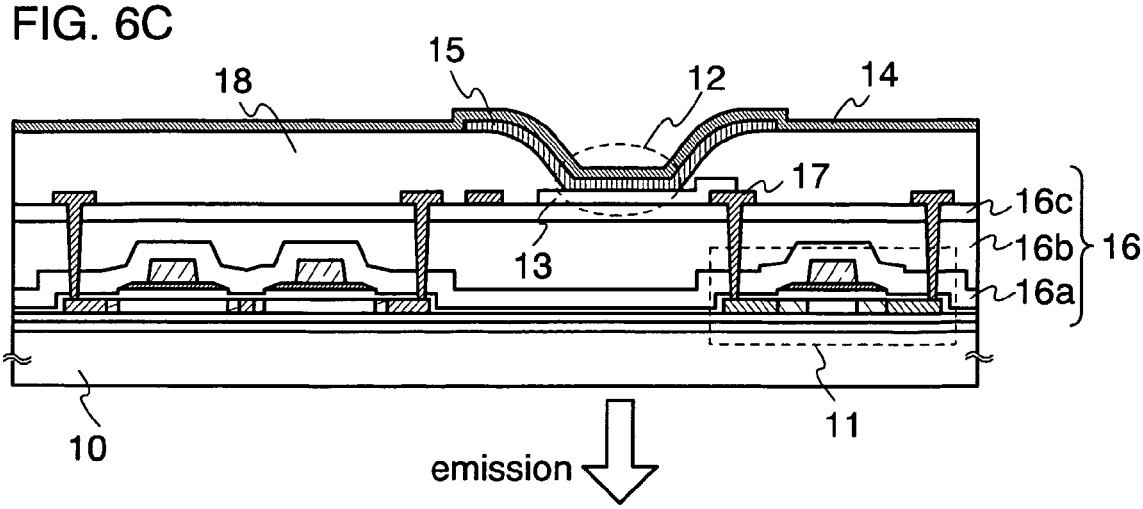

In FIGS. 6A to 6C, a portion surrounded by a dashed line is a transistor 11 which is provided for driving a light-emitting element 12 of the present invention. The light-emitting element 12 is a light-emitting element of the present invention including a layer 15 in which a layer generating holes, a layer generating electrons, and a layer containing a light-emitting substance of the present invention are stacked between a first electrode 13 and a second electrode 14. A drain of the transistor 11 and the first electrode 13 are electrically connected to each other by a wiring 17 penetrating a first interlayer insulating film 16 (16a, 16b and 16c). Also, the light-emitting element 12 is separated from another light-emitting element provided adjacently by a partition layer 18. The light-emitting device of the present invention including such a structure is provided over a substrate 10 in this embodiment mode.

Further, the transistor 11 shown in FIGS. 6A to 6C is a top gate type in which a gate electrode is provided on an opposite side of the substrate with a semiconductor layer as a center. However, the structure of the transistor 11 is not particularly limited, for example, a bottom gate type may also be used. In a case of a bottom gate type, a structure in which a protective film is formed over the semiconductor layer which forms a channel (a channel protected type) may be used, or a structure in which a part of a semiconductor layer which forms a channel is concave (a channel etched type) may also be used.

A semiconductor layer included in the transistor 11 may be either crystalline or amorphous. It may also be semiamorphous.

The semiamorphous semiconductor has an intermediate structure between an amorphous structure and a crystalline structure (including a single crystal structure and a polycrystalline structure), and a third condition that is stable in terms of free energy. The semiamorphous semiconductor includes a crystalline region having a short-range order and lattice distortion. A crystal grain with a size of 0.5 to 20 nm is included in at least part of the film. Raman spectrum is shifted lower wavenumbers than 520 cm$^{-1}$. The diffraction peaks of (111) and (220), which are believed to be derived from Si crystal lattice, are observed in X-ray diffraction. The semiamorphous semiconductor contains hydrogen or halogen of at least 1 atom % or more for terminating dangling bonds. Therefore, the semiamorphous semiconductor is also referred to as a microcrystalline semiconductor. The semiamorphous semiconductor is formed by glow discharge decomposition (plasma CVD) of $SiH_4$, $Si_2H_6$, $SiH_2Cl_2$, $SiHCl_3$, $SiCl_4$, or $SiF_4$. These gases may also be diluted with $H_2$, or a mixture of $H_2$ and one or more of rare gas elements selected from He, Ar, Kr, and Ne. The dilution ratio is set to be in a range of 2 to 1000 times. The pressure is set to be in the range of approximately 0.1 to 133 Pa. The power frequency is set to be 1 to 120 MHz, preferably 13 to 60 MHz. The substrate heating temperature may be set to be 300° C. or less, more preferably 100 to 250° C. As impurity elements contained in the film, each concentration of impurities in atmospheric components such as oxygen, nitrogen, and carbon is preferably set to be $1 \times 10^{20}$/$cm^3$ or less. In particular, the oxygen concentration is set to be $5 \times 10^{19}$/$cm^3$ or less, preferably $1 \times 10^{19}$/$cm^3$ or less.

As a specific example of a crystalline semiconductor layer, a semiconductor layer formed from single-crystal silicon, polycrystalline silicon, silicon germanium, or the like can be given. The crystalline semiconductor layer may be formed by laser crystallization. For example, the crystalline semiconductor layer may be formed by crystallization with use of a solid phase growth method using nickel or the like.

In a case where a semiconductor layer is formed using an amorphous material, for example, an amorphous silicon, it is preferable that all of the transistor 11 and other transistors (transistors included in a circuit for driving a light-emitting element) be a light-emitting device having circuits including N-channel transistors. In other cases, a light-emitting device having circuits including either N-channel transistors or P-channel transistors may be used. Moreover, a light-emitting device having circuits including both an N-channel transistor and a P-channel transistor may also be used.

Furthermore, the first interlayer insulating film 16 may be a multi layer as shown in FIGS. 6A to 6C, or a single layer. Note that 16a is formed of an inorganic material such as silicon oxide or silicon nitride, 16b is formed of acrylic or siloxane (note that siloxane is a compound that has a Si—O—Si bond as a main skeleton and also includes hydrogen or an alkyl group such as a methyl group as a substituent), or a material with a self-planarizing property which is capable of being formed by coating deposition, such as silicon oxide. Moreover, 16c is formed of a silicon nitride film containing argon (Ar). Materials included in each layer are not particularly limited, and materials which are not described here may also be used. Alternatively, layers formed using materials other than these materials may be further combined. As described above, the first interlayer insulating film 16 may be formed using both an inorganic material and an organic material, or either an inorganic material or an organic material.

An edge portion of the partition layer 18 preferably has a shape in which the radius of curvature is continuously changed. The partition layer 18 is formed by using acrylic, siloxane, resist, silicon oxide, or the like. Further, the partition layer 18 may be formed using any one or both of an inorganic material and an organic material.

In FIGS. 6A to 6C, only the first interlayer insulating film 16 is provided between the transistor 11 and the light-emitting element 12; however, a second interlayer insulating film 19 (19a and 19b) may also be provided in addition to the first interlayer insulating film 16 (16a and 16b) as shown in FIG. 6B. In a light-emitting device shown in FIG. 6B, the first electrode 13 penetrates the second interlayer insulating film 19 to be connected to the wiring 17.

The second interlayer insulating film 19 may be a multi layer including the second interlayer insulating films 19a and 19b similarly to the first interlayer insulating film 16, or a single layer. The second interlayer insulating film 19a is formed of a material with a self-planarizing property which is capable of being formed by application deposition, such as silicon oxide. Moreover, the second interlayer insulating film 19b is formed of a silicon nitride film containing argon (Ar). Materials included in each layer are not particularly limited, and materials which are not described here may also be used. Alternatively, layers formed using materials other than these materials may be further combined. As described above, the second interlayer insulating film 19 may be formed using both an inorganic material and an organic material, or either an inorganic material or an organic material.

When the first electrode and the second electrode are both formed using a material having a light-transmitting property in the light-emitting element 12, light can be taken out through both the first electrode 13 and the second electrode 14 as shown by hollow arrows in FIG. 6A. When only the second electrode 14 is formed using a material having a light-transmitting property, light can be taken out only through the second electrode 14 as shown by a hollow arrow in FIG. 6B. In this case, the first electrode 13 is preferably formed using a material having high reflectivity, or a film formed using a material having high reflectivity (reflection film) is preferably provided under the first electrode 13. When only the first electrode 13 is formed using a material having a light-transmitting property, light can be taken out only through the first electrode 13 as indicated by a hollow arrow in FIG. 6C. In this case, the second electrode 14 is preferably formed using a material having high reflectivity or a reflection film is preferably provided above the second electrode 14.

Moreover, the light-emitting element 12 may have a structure in which the layer 15 is stacked so as to operate when voltage is applied to make electric potential of the second electrode 14 higher than that of the first electrode 13, or a structure in which the layer 15 is stacked so as to operate when voltage is applied so that the electric potential of the second electrode 14 is lower than that of the first electrode 13. In the former case, the transistor 11 is an N-channel transistor, and in the latter case, the transistor 11 is a P-channel transistor.

As described above, in this embodiment mode, an active matrix type light-emitting device, in which drive of the light-emitting element is controlled by the transistor, is described. However, the present invention may be applied to a passive type light-emitting device without being limited to an active matrix type light-emitting device.

Figure 7:
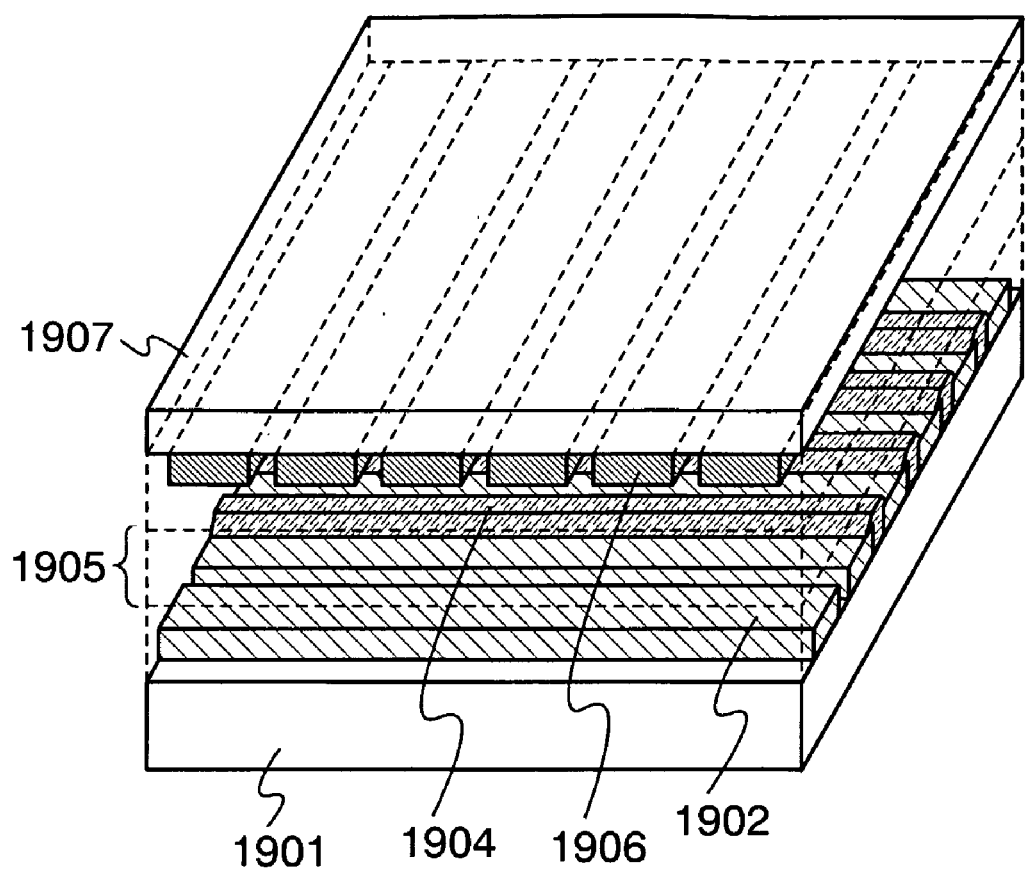
FIG. 7 is a view explaining a light-emitting device to which the present invention is applied.

FIG. 7 is a perspective view showing a passive type light-emitting device to which the present invention is applied. In FIG. 7, an electrode 1902 and an electrode 1906 are provided between a substrate 1901 and a substrate 1907. The electrodes 1902 and 1906 are provided so as to be intersected with each other. Furthermore, a light-emitting layer 1905 (shown by a dashed line so that the electrode 1902, a partition layer 1904, and the like can be seen) is provided between the electrode 1902 and the electrode 1906. Further, a hole transporting layer, an electron transporting layer, and the like may be provided between the light-emitting layer 1905 and the electrode 1902, or between the light-emitting layer 1905 and the electrode 1906. An edge portion of the electrode 1902 is covered with the partition layer 1904. Also, a passive type light-emitting device can be driven with low power consumption by including the light-emitting element of the present invention which is operated with low driving voltage.

Embodiment Mode 6

A light-emitting device including the light-emitting element of the present invention can be driven with low driving voltage; therefore, an electronic appliance which uses less power and is economical can be obtained by the present invention. Also, a light-emitting device manufactured by using the light-emitting element of the present invention needs lower manufacturing cost; therefore, an electronic appliance at low price can be obtained by applying the light-emitting element of the present invention to a display portion.

Figure 8A:
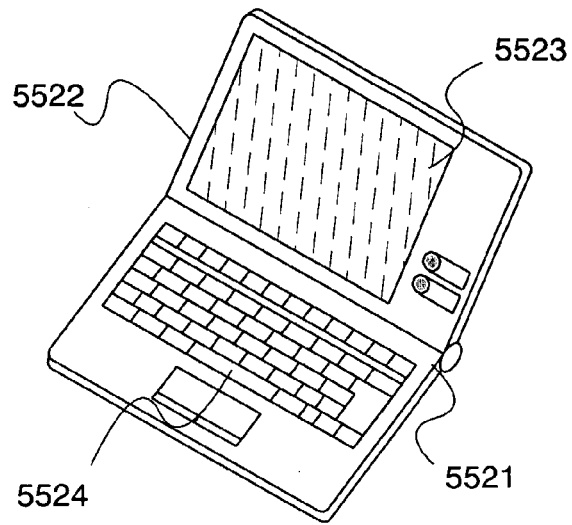
FIGS. 8A to 8C are views showing electronic appliances to which the present invention is applied.
Figure 8B:
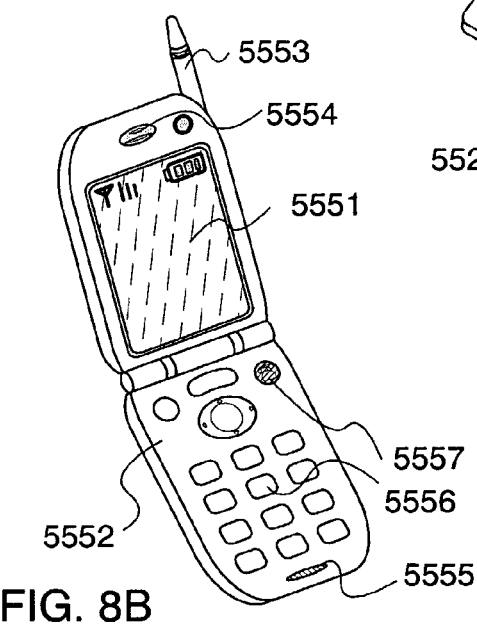
Figure 8C:
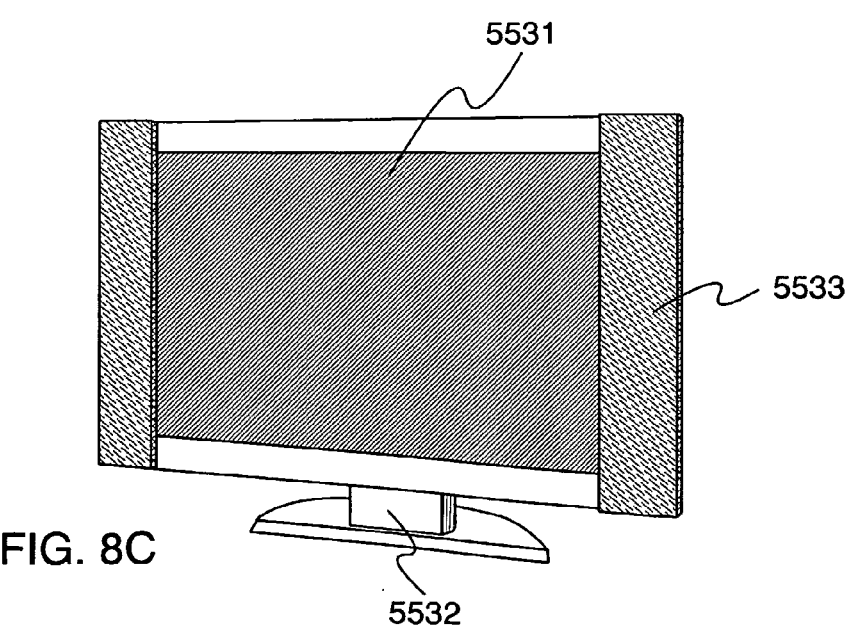

Embodiments of electronic appliances of the present invention mounted with a light-emitting device to which the present invention is applied, is shown in FIGS. 8A to 8C.

FIG. 8A shows a computer according to the present invention, and in the computer, the light-emitting device of the present invention, in which the light-emitting elements using the organometallic complex described in Embodiment Modes 1 and 2 as a light-emitting substance are aligned in a matrix form, is included in a display portion 5523. In this manner, by incorporating the light-emitting device including the light-emitting element containing the organometallic complex of the present invention as a display portion, a computer can be completed. The computer in FIG. 8A includes a main body 5521 to which a hard disk, a CPU, and the like are mounted, a housing 5522 for holding the display portion 5523, a keyboard 5524, and the like, in addition to the display portion 5523. Such a computer is completed using the organometallic complex of the present invention, which is synthesized with high yield; therefore, the computer needs low cost of raw materials and is inexpensive. Also, a computer according to the present invention uses the light-emitting device of the present invention which is operated with low power consumption as a display portion; therefore, power consumption of a display is low, and is economical.

FIG. 8B shows a telephone set according to the present invention, and in the telephone set, the light-emitting device of the present invention, in which the light-emitting elements using the organometallic complex described in Embodiment Modes 1 and 2 as a light-emitting substance are aligned in a matrix form, is included in a display portion 5551 mounted in a main body 5552. In this manner, by incorporating the light-emitting device including a light-emitting element containing the organometallic complex of the present invention as a display portion, a telephone set can be completed. The telephone set in FIG. 8B includes an audio output portion 5554, an audio input portion 5555, operation switches 5556 and 5557, an antenna 5553, and the like, in addition to the display portion 5551. In this manner, a telephone set can be completed by incorporating the light-emitting device including the light-emitting element containing the organometallic complex of the present invention as a display portion. Such a telephone set is completed by using the organometallic complex of the present invention which is synthesized with good yield; therefore, the telephone set needs low cost of raw materials and is inexpensive. Also, a telephone set according to the present invention uses the light-emitting device of the present invention which is operated with low power consumption as a display portion; therefore, power consumption of a display is low, and is economical.

FIG. 8C shows a television set according to the present invention, and in the television set, the light-emitting device of the present invention, in which the light-emitting elements using the organometallic complex described in Embodiment Modes 1 and 2 as a light-emitting substance are aligned in a matrix form, is included in a display portion 5531. In this manner, by incorporating the light-emitting device including a light-emitting element containing the organometallic complex of the present invention as a display portion, a television set can be completed. The television set in FIG. 8C includes a housing 5532 for holding the display portion 5531, a speaker 5533, and the like, in addition to the display portion 5531. In this manner, a television set can be completed by incorporating the light-emitting device including the light-emitting element containing the organometallic complex of the present invention as a display portion. Such a television set is completed by using the organometallic complex of the present invention, which is synthesized with high yield; therefore, the television set needs low cost of raw materials and is inexpensive. Also, a television set according to the present invention uses the light-emitting device of the present invention which is operated with low power consumption as a display portion; therefore, power consumption of a display is low, and is economical.

The above electronic appliances including the light-emitting device of the present invention in a display portion, includes, in addition to the computer, telephone set, and the like described in FIGS. 8A to 8C, electronic appliances such as a navigation system, a video, a camera, and the like to which the light-emitting device including the light-emitting element of the present invention is mounted to a display portion.

Embodiment 1

SYNTHESIS EXAMPLE 1

A method for synthesizing (acetylacetonato)bis[2,3-diphenyl-5,6,7,8-tetrahydroquinoxalinate]iridium(III) (abbreviation: Ir(dpqtH)$_2$(acac)), which is one of the organometallic complexes of the present invention and is represented by a structural formula (8) will be described.

[Step 1: Synthesis of Ligand (Abbreviation: DPQtH)]

First, 5.84 g of benzyl (manufactured by Tokyo Kasei Kogyo Co., Ltd) was mixed with 3.17 g of trans-1,2-cyclohexanediamine (manufactured by Kanto Kagaku) by using 150 mL of ethanol as a solvent. Then, the mixed solution was refluxed for 3 hours at 50° C. After that, the refluxed solution was cooled to be a room temperature. A deposit was obtained by filtering the refluxed solution. After that, 2,3-diphenyl-4a,5,6,7,8,8a-hexahydroquinoxaline was obtained by recrystallizing the deposit with ethanol (light yellow crystal, yield: 96%). Subsequently, 7.66 g of 2,3-diphenyl-4a,5,6,7,8,8a-hexahydroquinoxaline, which was obtained in the above step, was mixed with 8.62 g of iron chloride (III) by using 80 mL of ethanol as a solvent. Then the mixed solution was gently stirred with heat for 3 hours. After the stirring, a ligand 2,3-diphenyl-5,6,7,8-tetrahydroquinoxaline (abbreviation: DPQtH) was obtained by adding water (milky white powder, yield: 88%). A synthesis scheme (d-1) of Step 1 is shown next.

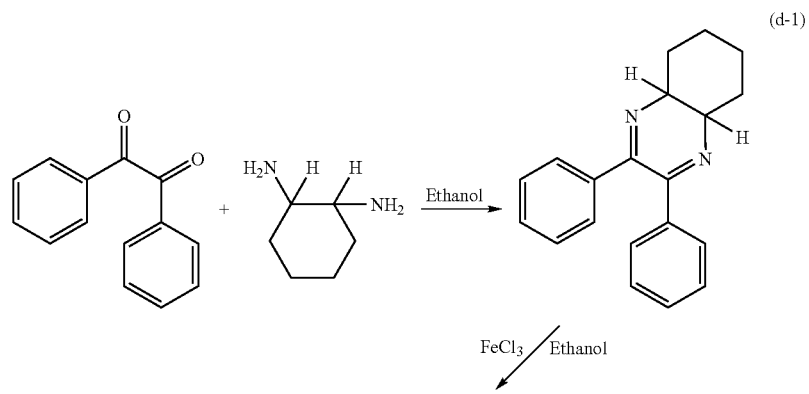

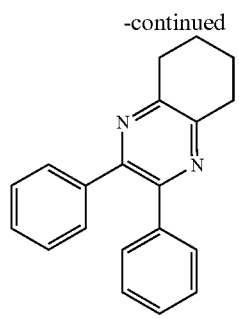

[Step 2: Synthesis of Binuclear Complex (Abbreviation: [Ir(dpqtH)₂Cl]₂)]

Subsequently, 3.98 g of the ligand DPQtH, which was obtained in the above step, was mixed with 1.65 g of iridium chloride hydrochloride hydrate (IrCl₃, HCl, H₂O) (manufactured by Sigma-Aldrich Co., Ltd) by using a mixed solution of 30 mL of 2-ethoxyethanol and 10 mL of water as a solvent to reflux under a nitrogen atmosphere for 18 hours; consequently, [Ir(dpqtH)₂Cl]₂ was obtained (red powder, yield: 98%). A synthesis scheme of Step 3 (d-2) is shown next.

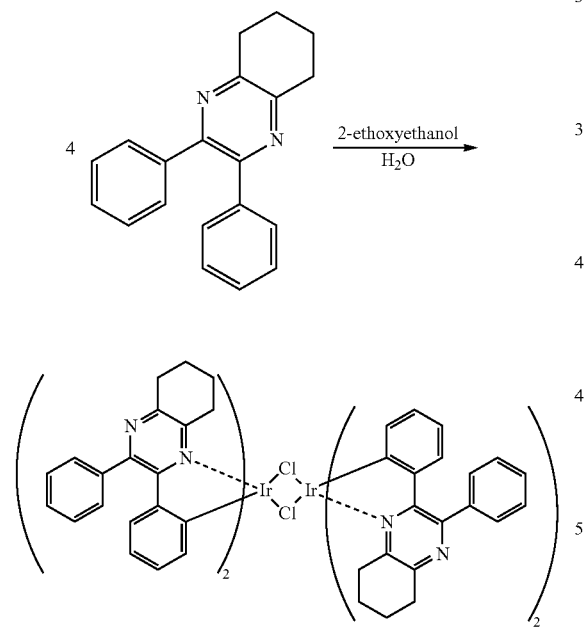

(d-2)

[Step 3: Synthesis of Organometallic Compound of the Present Invention (Abbreviation: Ir(dpqtH)₂(acac))]

Furthermore, 2.06 g of [Ir(dpqtH)₂Cl]₂ which was obtained in the above step, 0.40 mL of acetylacetone, and 1.37 g of sodium carbonate are mixed using 30 mL of 2-ethoxyethanol as a solvent. Then, the mixed solution was refluxed under a nitrogen atmosphere for 17 hours. After that, a deposit obtained by the reflux was filtered; consequently, orange powder was obtained (yield: 53%). Synthesis scheme of Step 3 (d-3) is shown next.

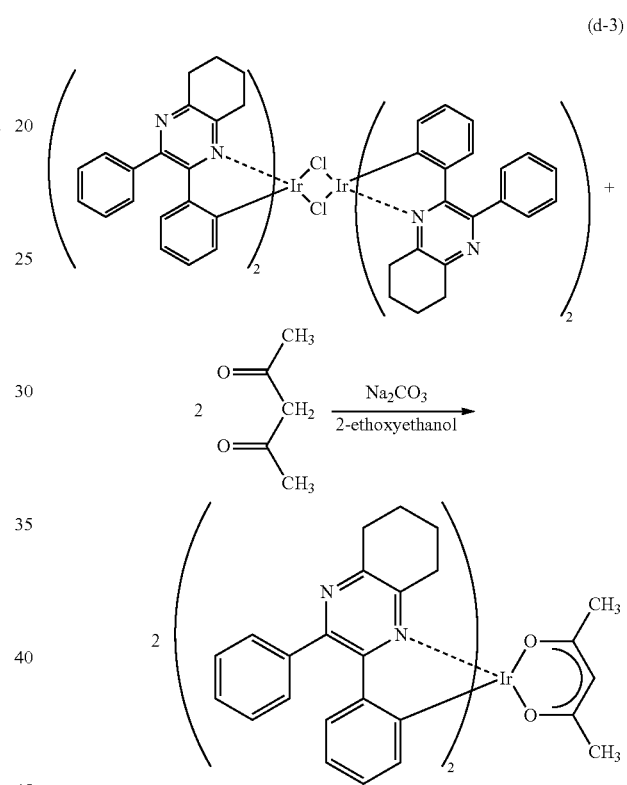

(d-3)

Figure 9:
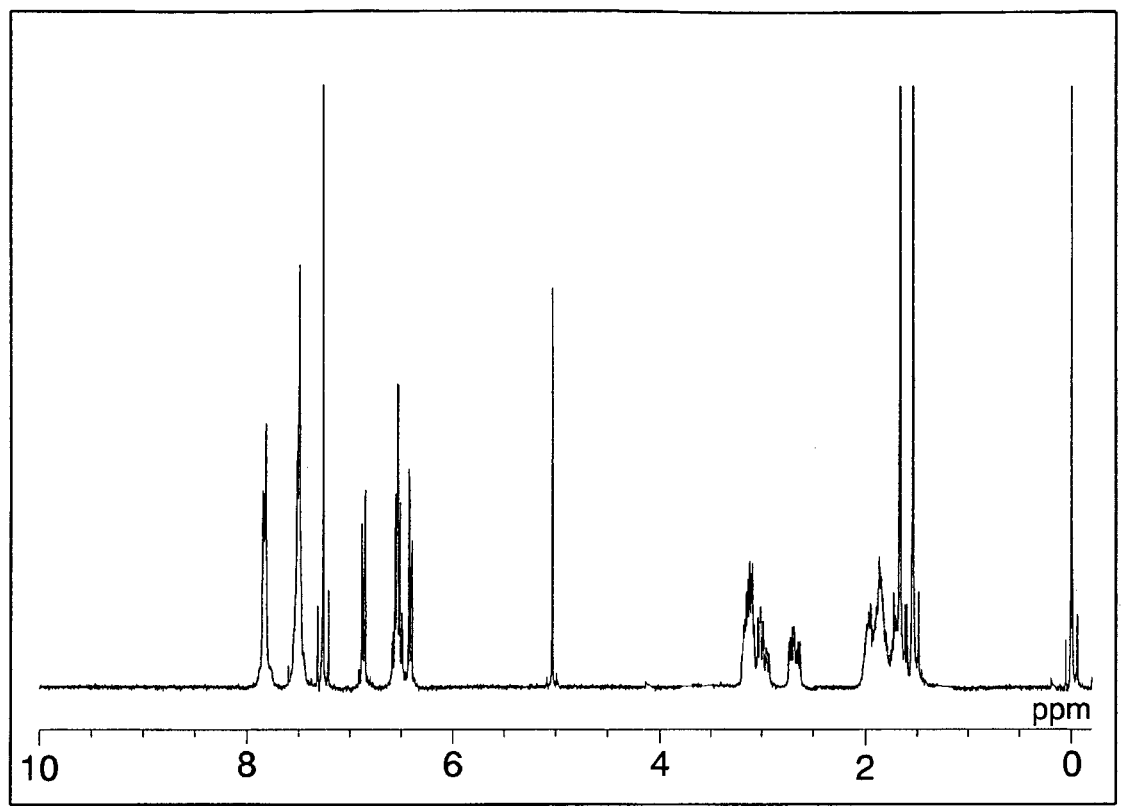
FIG. 9 is a chart obtained by analyzing an organometallic complex synthesized in Synthesis Example 1 by using $^1$H-NMR.

The obtained orange powder was analyzed by nuclear magnetic resonance spectroscopy ($^1$H-NMR), and a result as described below was obtained. The obtained product was found to be Ir(dpqtH)₂(acac) which is one of the organometallic complexes of the present invention and is represented by the structural formula (8). A chart of $^1$H-NMR is shown in FIG. 9.

$^1$H-NMR. δ(CDCl₃): 7.84 (m, 4H), 7.50 (m, 6H), 6.87 (d, 2H), 6.54 (4H), 6.41 (d, 2H), 5.04 (s, 1H), 3.08 (m, 6H), 2.69 (2H), 1.87 (m, 6H), 1.73 (2H), 1.67 (s, 6H).

A decomposition temperature $T_d$ of the obtained organometallic compound Ir(dpqtH)₂(acac) was measured by Thermo-Gravimetric/Differential Thermal Analyzer (manufactured by Seiko Instrument Inc., TG/DTA 320 type), and the result was $T_d$=332° C. It was found that the obtained product showed favorable heat resistance.

Subsequently, an absorption spectrum (an ultraviolet-visible light spectrophotometer, manufactured by Japan Spectroscopy Corporation, V550 type) and an emission spectrum (a fluorescence spectrophotometer, manufactured by Hamamatsu Photonics Corporation, FS 920) of Ir(dpqtH)₂

Figure 10:
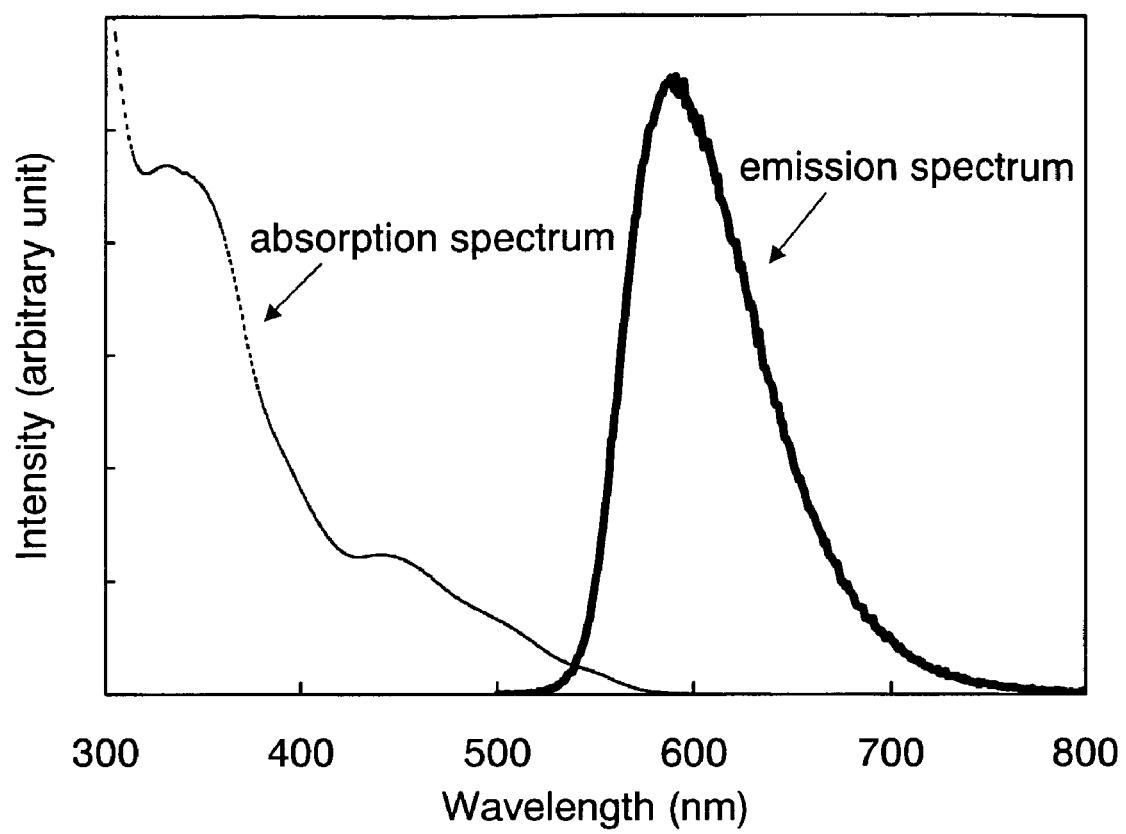
FIG. 10 is a graph showing an absorption spectrum and an emission spectrum of an organometallic complex synthesized in Synthesis Example 1.

(acac) in dichloromethane solution was measured at a room temperature. The result is shown in FIG. 10. In FIG. 10, a horizontal axis indicates a wavelength (nm) and a vertical axis indicates intensity of absorbance and light emission (arbitrary unit). As shown in FIG. 10, the absorption spectrum of Ir(dpqtH)$_2$(acac) of the present invention has peaks at 331 nm, 441 nm, 500 nm, and 550 nm. Also, the light emission spectrum of Ir(dpqtH)$_2$(acac) has a peak at 590 nm, and it was an orange light emission.

Also, gas containing oxygen was injected to a dichloromethane solution containing the obtained Ir(dpqtH)$_2$(acac), and the light emission intensity was examined when Ir(dpqtH)$_2$(acac) dissolved with oxygen was made to emit light. Furthermore, argon was injected to a dichloromethane solution containing the obtained Ir(dpqtH)$_2$(acac), and the light emission intensity was examined when Ir(dpqtH)$_2$(acac) dissolved with argon was made to emit light. As a result, it was found that Ir(dpqtH)$_2$(acac) shows a tendency that the intensity of light emission obtained in the state with dissolved argon is higher than that obtained in the state with dissolved oxygen. Since this tendency is the same as shown by a phosphorescent substance, it has been confirmed that the light emission derived from Ir(dpqtH)$_2$(acac) is caused by phosphorescence.

SYNTHESIS EXAMPLE 2

In this synthesis example, a method for synthesizing bis[2,3-bis(4-fluorophenyl)-5,6,7,8-tetrahydroquinoxalinato](picolinato)iridium(III) (abbreviation; Ir(FdpqtH)$_2$(pic)) which is one of the organometallic complexes of the present invention and is represented by a structural formula (16) will be described.

[Step 1: Synthesis of Ligand (HfdpqtH)]

First, 12.07 g of 4,4'-difluorobenzil (manufactured by Tokyo Kasei Kogyo Co., Ltd) was mixed with 5.60 g of trans-1,2-cyclohexanediamine (manufactured by Kanto Kasei Co., Ltd) by using 300 mL of ethanol as a solvent, and then the mixed solution was refluxed under a nitrogen atmosphere for 3 hours. By leaving a the refluxed solution to be cooled to a room temperature and taking out a deposited crystal by filtration, 2,3-bis(4-fluorophenyl)-4a,5,6,7,8,8a-hexahydroquinoxaline was obtained (light yellow plate-like crystal, yield: 94%). Subsequently, 6.90 g of 2,3-bis(4-fluorophenyl)-4a,5,6,7,8,8a-hexahydroquinoxaline which was obtained in the above step was mixed with 6.90 g of iron chloride (III) using 150 mL of ethanol as a solvent to gently stir with heat for 3 hours at 50° C. After the stirring, a deposition was caused by adding water to the stirred solution. A deposit was taken out by filtering and was washed with ethanol. Then, by recrystallizing the deposit with ethanol, a ligand 2,3-bis(4-fluorophenyl)-5,6,7,8-tetrahydroquinoxaline (abbreviation: HfdpqtH) was obtained (milky white powder, yield: 68%). Synthesis scheme of Step 1 (e-1) is shown next.

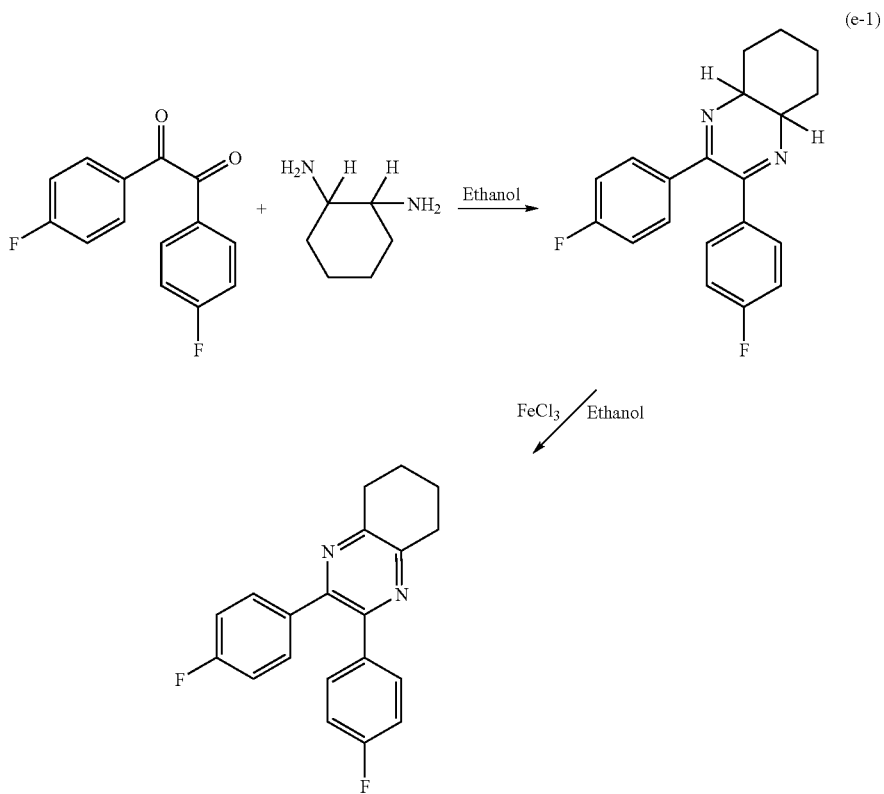

(e-1)

[Step 2: Synthesis of Binuclear Complex [Ir(FdpqtH)$_2$Cl]$_2$]

Subsequently, 4.70 g of the ligand FDPQtH which was obtained in the above step was mixed with 1.74 g of iridium chloride hydrate (IrCl$_3$, H$_2$O) (manufactured by Sigma-Aldrich Co., Ltd) by a mixed solution of 30 mL of 2-ethoxyethanol and 10 mL of water as a solvent. Then, the mixed solution was refluxed under a nitrogen atmosphere for 18 hours. After that, a deposited solid obtained by the reflux was filtered; consequently, a binuclear complex [Ir(FdpqtH)$_2$Cl]$_2$ was obtained as yellow orange powder (yield: 93%). Synthetic scheme of Step 2 (e-2) is shown next.

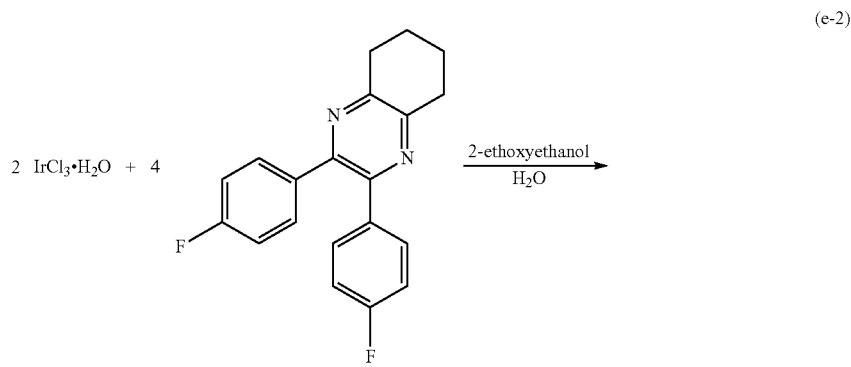

(e-2)

[Step 3: Synthesis of an Organometallic Complex (Ir(Fd-pqtH)$_2$(pic)) of the Present Invention]

Furthermore, 0.90 g of [Ir(FdpqtH)$_2$Cl]$_2$ which was obtained in the above step was mixed with 0.51 g of picoline acid (manufactured by Tokyo Kasei Kogyo Co., Ltd) by using 20 mL of 2-ethoxy ethanol as a solvent. Then, the mixed solution was refluxed under a nitrogen atmosphere for 20 hours. After that, a deposited solid was filtered, and yellow powder was obtained (yield: 59%). Synthetic scheme of Step 3 (e-3) is shown next.

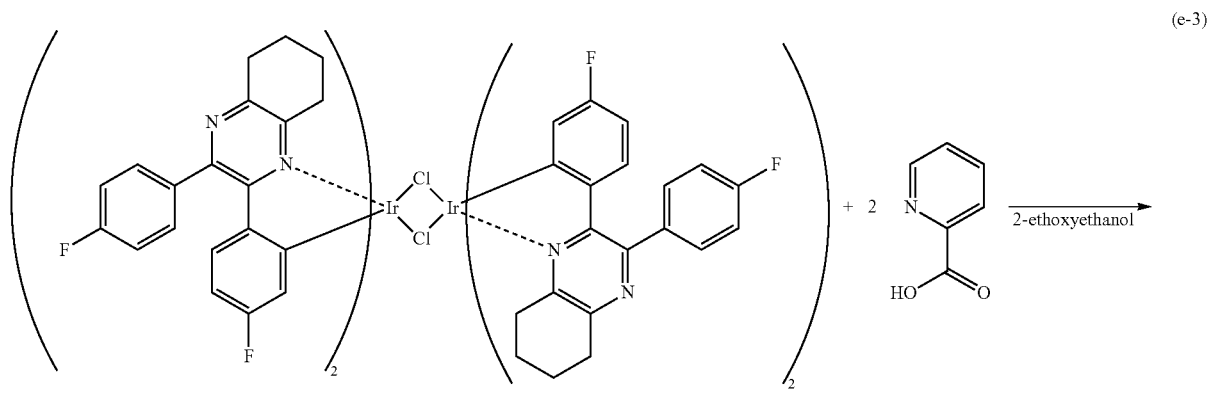

(e-3)

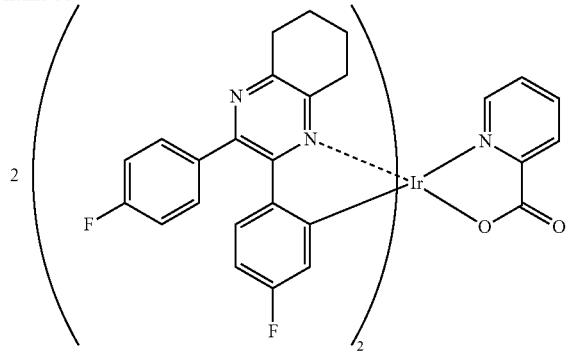

Figure 16A:
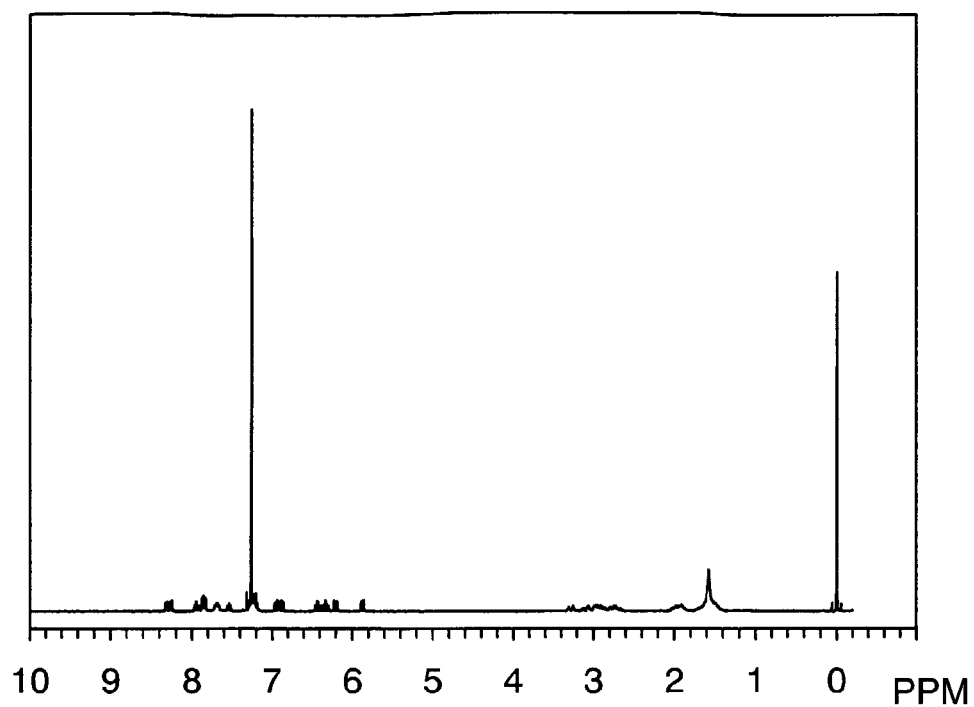
FIGS. 16A and 16B are charts obtained by analyzing an organometallic complex of the present invention synthesized in Synthesis Example 2 by using $^1$H-NMR.
Figure 16B:
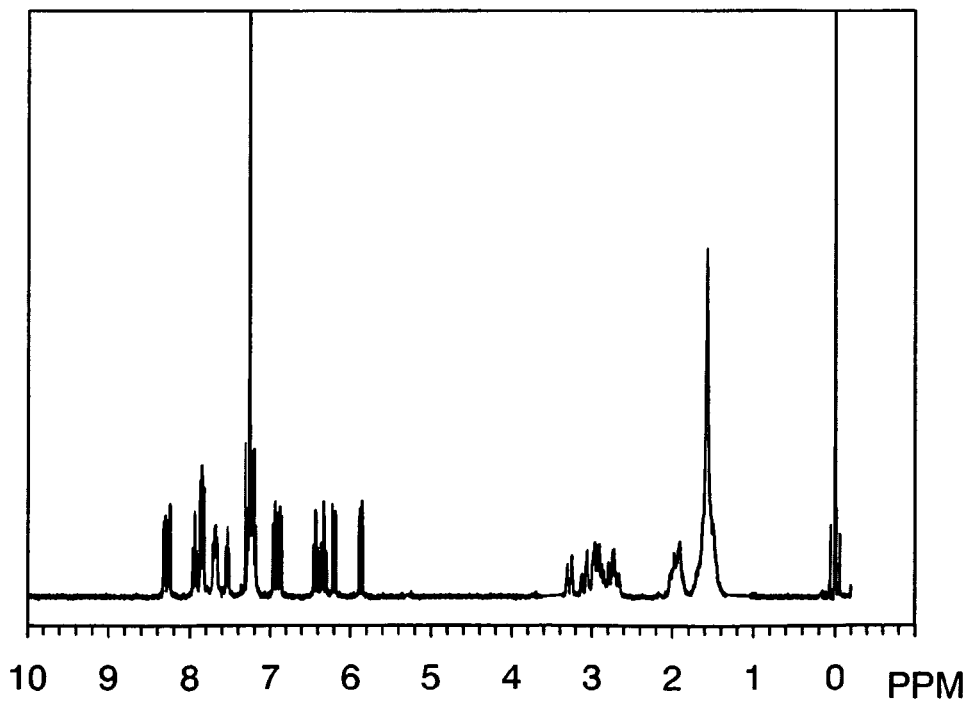

The obtained orange powder was analyzed by nuclear magnetic resonance spectroscopy ($^1$H-NMR), and a result as described below was obtained. The obtained product was found to be Ir(FdpqtH)$_2$(pic) which is one of the organometallic complexes of the present invention and is represented by the structural formula (16). A result of analysis of $^1$H-NMR is shown below, and a chart of $^1$H-NMR is shown in FIGS. 16A and 16B. Note that FIG. 16B is a chart in which part of FIG. 16A is enlarged in a vertical direction.

$^1$H-NMR. δ(CDCl$_3$): 8.31 (d, 1H), 8.26 (d, 1H), 7.94 (td, 1H), 7.85 (m, 2H), 7.68 (m, 2H), 7.53 (m, 1H), 7.31-7.19 (m, 4H), 6.97-6.86 (m, 2H), 6.43 (td, 1H), 6.33 (td, 1H), 6.20 (dd, 1H), 5.87 (dd, 1H), 3.25-2.73 (m, 5H), 1.91 (m, 2H), 1.52 (m, 9H).

A decomposition temperature T$_d$ of the obtained organometallic complex Ir(FdpqtH)$_2$(pic) of the present invention was measured by Thermo-Gravimetric/Differential Thermal Analyzer (manufactured by Seiko Instrument Inc., TG/DTA 320 type), and the result was T$_d$=342° C. It was found that the obtained product showed favorable heat resistance.

Figure 17:
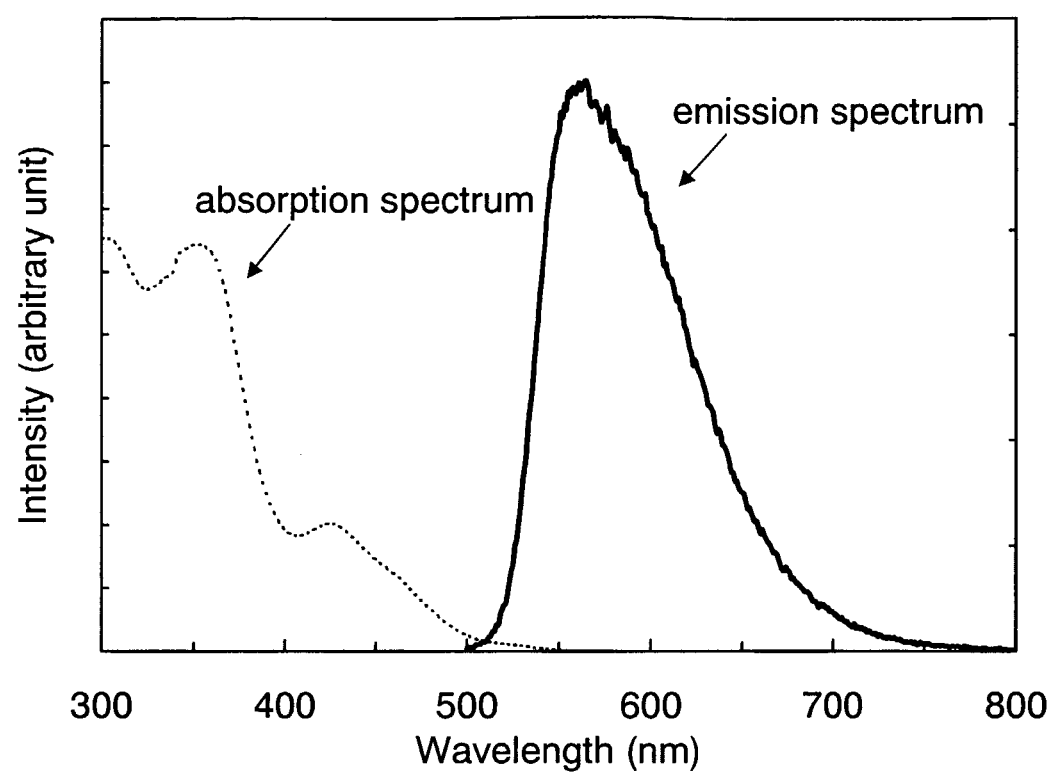
FIG. 17 is a graph showing an absorption spectrum and an emission spectrum of an organometallic complex synthesized in Synthesis example 2.

Subsequently, an absorption spectrum (an ultraviolet-visible light spectrophotometer, manufactured by Japan Spectroscopy Corporation, V550 type) and an emission spectrum (a fluorescence spectrophotometer, manufactured by Hamamatsu Photonics Corporation, FS 920) of Ir(FdpqtH)$_2$(pic) was measured at a room temperature using a dichloromethane solution which was degassed. The result is shown in FIG. 17. In FIG. 17, a horizontal axis indicates a wavelength (nm) and a vertical axis indicates intensity (arbitrary unit). As shown in FIG. 10, the organometallic complex (Ir(FdpqtH)$_2$(pic)) of the present invention has absorption peaks at 302 nm, 351 nm, 425 nm, 460 nm, and 520 nm. Also, the light emission spectrum was yellow green light emission which had a light emission peak at 550 nm.

SYNTHESIS EXAMPLE 3

In this synthesis example, a method for synthesizing bis[2,3-bis(4-fluorophenyl)-5,6,7,8-tetrahydroquinoxalinato][tetrakis(1-pyrazolyl)borato]iridium(III) (abbreviation: Ir(FdpqtH)$_2$(bpz$_4$)) which is one of the organometallic complexes of the present invention and is represented by a structural formula (22) will be described.

First, 1.10 g of binuclear complex [Ir(FdpqtH)$_2$Cl]$_2$, which was obtained in Step 2 of Synthesis Example 2, was suspended in 40 mL of dichloromethane. Next, a solution, in which 0.40 g of trifluoromethansulfonate silver (abbreviation: Ag(OTf)) is dissolved by using 40 mL of methanol as a solvent, was dropped to the suspension. Subsequently, stirring was performed at a room temperature for 2 hours, the obtained suspension solution was centrifuged, and a supernatant solution obtained by the centrifugation was divided by decantation to be concentrated and dried. Furthermore, a solid which was obtained by being concentrated and dried was mixed with 0.70 g of tetrakis(1-pyrazolyl)borate potassium salt (manufactured by Acros Organic Co.) by using 30 mL of acetonitrile as a solvent. Then, the mixed solution was refluxed under a nitrogen atmosphere for 18 hours, and yellow powder was obtained (yellow powder, yield: 38%). Synthesis scheme (f-1) is shown next.

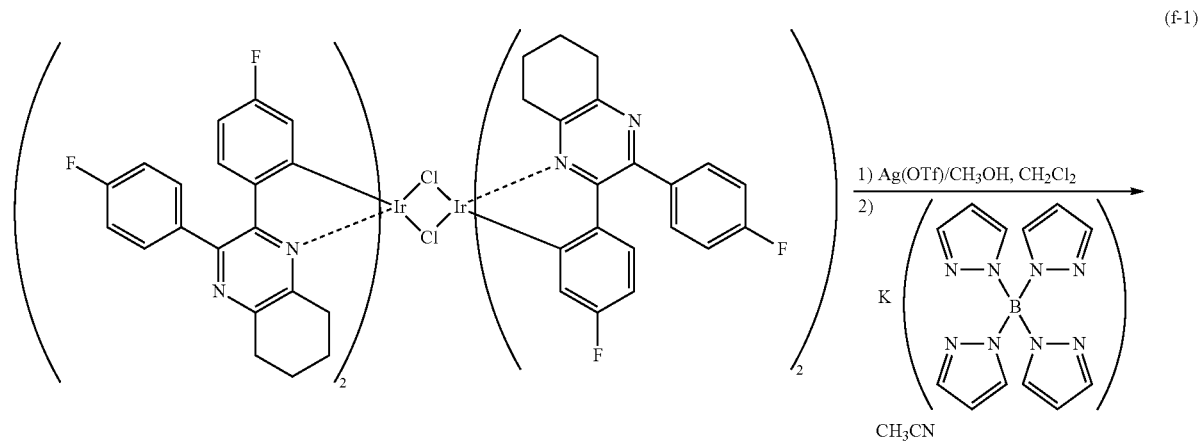

(f-1)

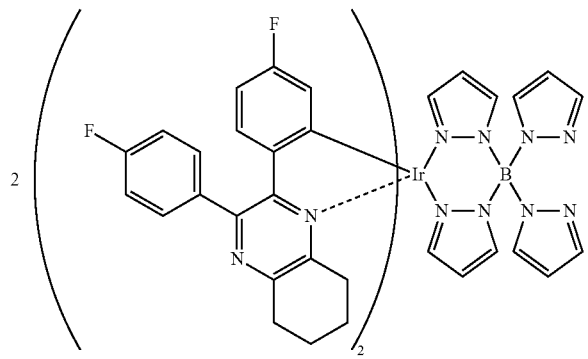

Figure 18A:
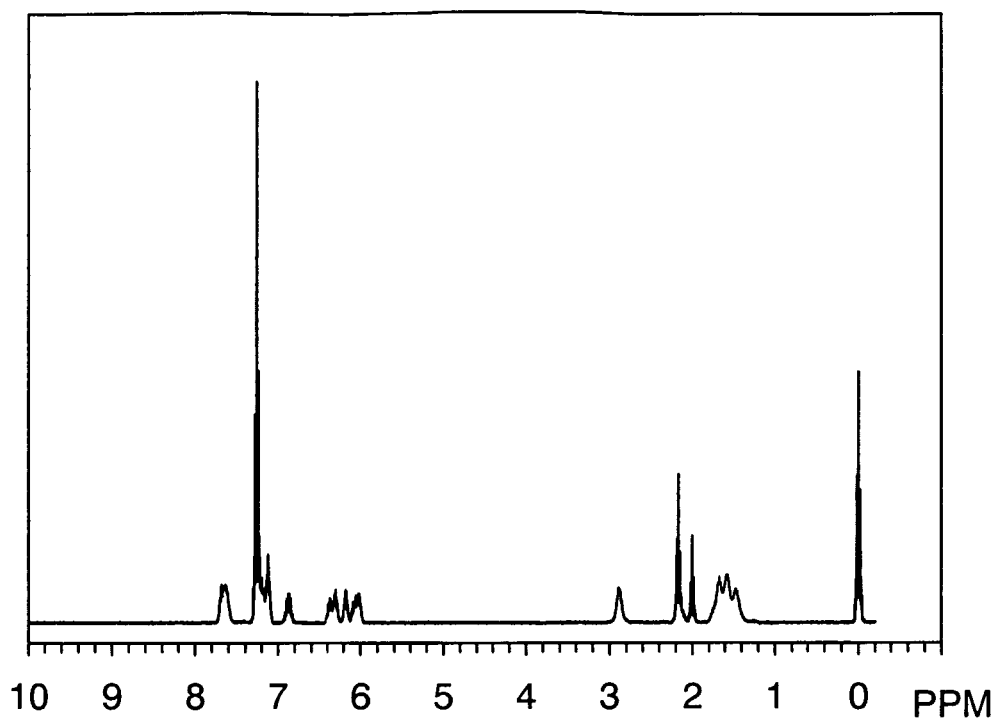
FIGS. 18A and 18B are charts obtained by analyzing an organometallic complex of the present invention synthesized in Synthesis Example 3 by using $^1$H-NMR.
Figure 18B:
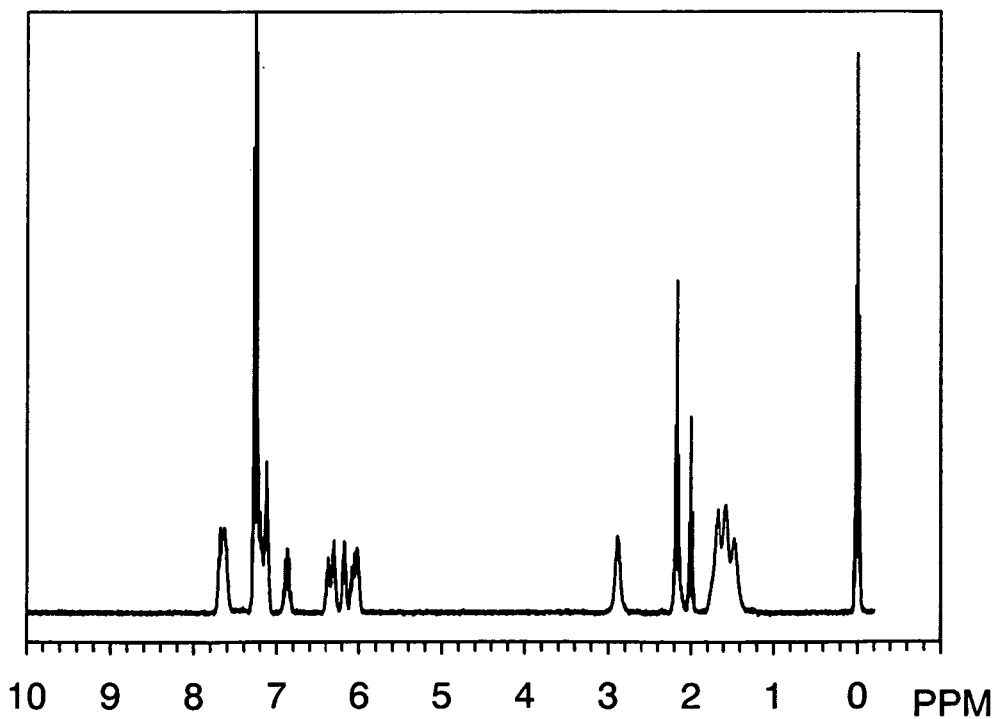

The obtained yellow powder was analyzed by nuclear magnetic resonance spectroscopy ($^1$H-NMR), and a result as described below was obtained. The obtained product was found to be Ir(FdpqtH)$_2$(bpz$_4$) which is one of the organometallic complexes of the present invention and is represented by the structural formula (22). A result of analysis of $^1$H-NMR is shown below, and a chart of $^1$H-NMR is shown in FIGS. 18A and 18B. Note that FIG. 18B is a chart in which part of FIG. 18A is enlarged in a vertical direction.

$^1$H-NMR. δ(ACETONE-d$_6$): 7.70-7.63 (m, 6H), 7.30-7.10 (m, 8H), 6.92-6.83 (m, 2H), 6.41-6.27 (m, 4H), 6.20-6.14 (m, 2H), 6.11-6.00 (m, 4H), 2.89 (m, 2H), 1.68-1.47 (m, 14H).

A decomposition temperature $T_d$ of the obtained organometallic complex of the present invention Ir(FdpqtH)$_2$(bpz$_4$) was measured by TG/DTA, and it was found that $T_d$=346° C. and the obtained product showed favorable heat resistance.

Figure 19:
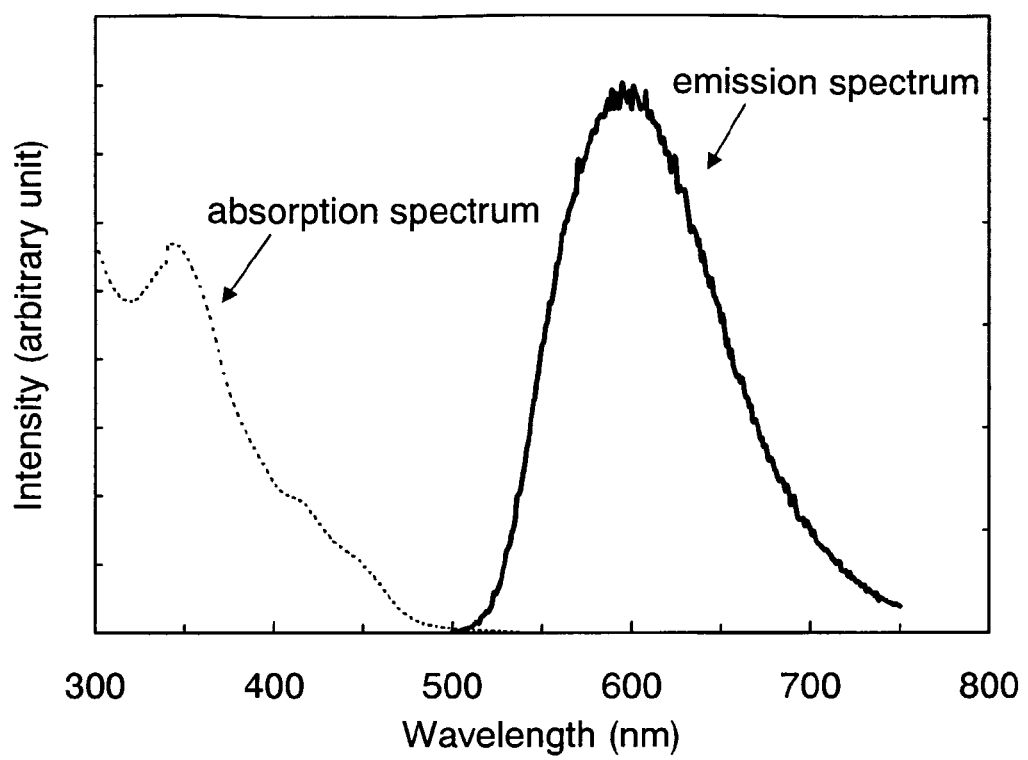
FIG. 19 is a graph showing an absorption spectrum and an emission spectrum of an organometallic complex synthesized in Synthesis Example 3.

Subsequently, an absorption spectrum (an ultraviolet-visible light spectrophotometer, manufactured by Japan Spectroscopy Corporation, V550 type) and an emission spectrum (a fluorescence spectrophotometer, manufactured by Hamamatsu Photonics Corporation, FS 920) of Ir(FdpqtH)$_2$(bpz$_4$) were measured at a room temperature using a dichloromethane solution which was degassed. The result is shown in FIG. 19. In FIG. 19, a horizontal axis indicates a wavelength (nm) and a vertical axis indicates intensity (arbitrary unit). As shown in FIG. 19, the organometallic complex Ir(FdpqtH)$_2$(bpz$_4$) of the present invention has absorption peaks at 344 nm, 412 nm, 440 nm, and 475 nm. Also, the light emission spectrum was orange light emission which had a light emission peak at 600 nm.

SYNTHESIS EXAMPLE 4

In this synthesis example, a method for synthesizing (acetylacenato)bis[2,3-bis(4-fluorophenyl)-5,6,7,8-tetrahydroquinoxalinato]iridium(III) (abbreviation: Ir(FdpqtH)$_2$(acac)) which is one of the organometallic complexes of the present invention and is represented by a structural formula (10) will be described.

2.26 g of the binuclear complex [Ir(FdpqtH)$_2$Cl]$_2$ which was obtained in Step 2 of Synthesis Example 2, 0.47 mL of acetylacetone, and 1.62 g of sodium carbonate were mixed using 30 mL of 2-ethoxyethanol as a solvent. Next, the mixed solution was refluxed under a nitrogen atmosphere for 16 hours. After that, a deposited solid by the reflux was filtered; consequently, orange power was obtained (yield: 39%). A synthesis scheme (g-1) is shown next.

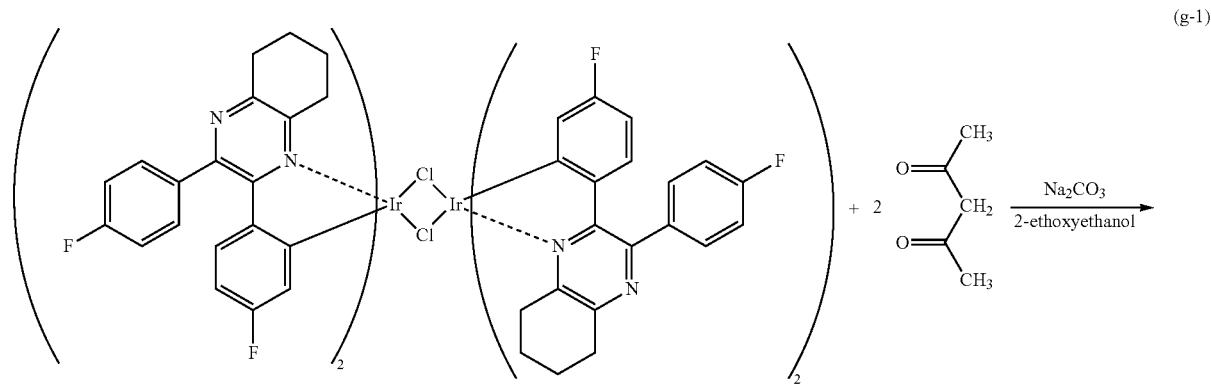

(g-1)

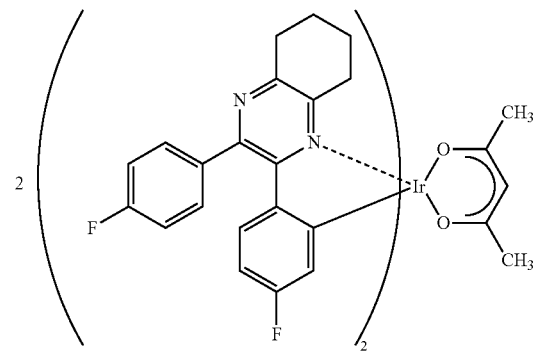

Figure 20A:
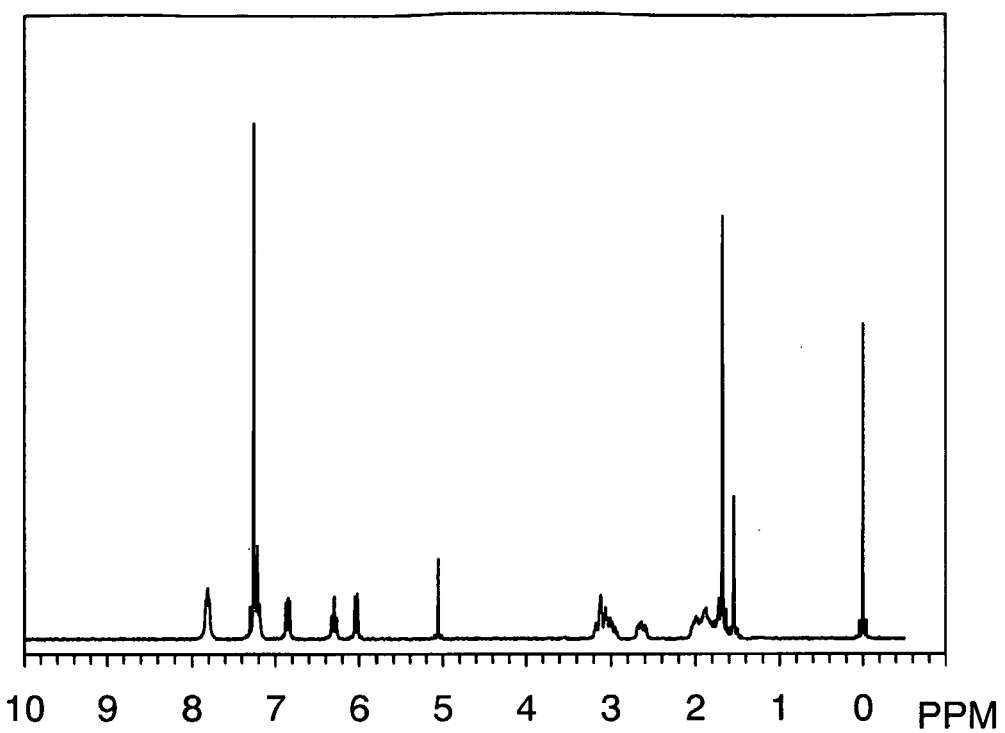
FIGS. 20A and 20B are charts obtained by analyzing an organometallic complex of the present invention synthesized in Synthesis Example 4 by using $^1$H-NMR.
Figure 20B:
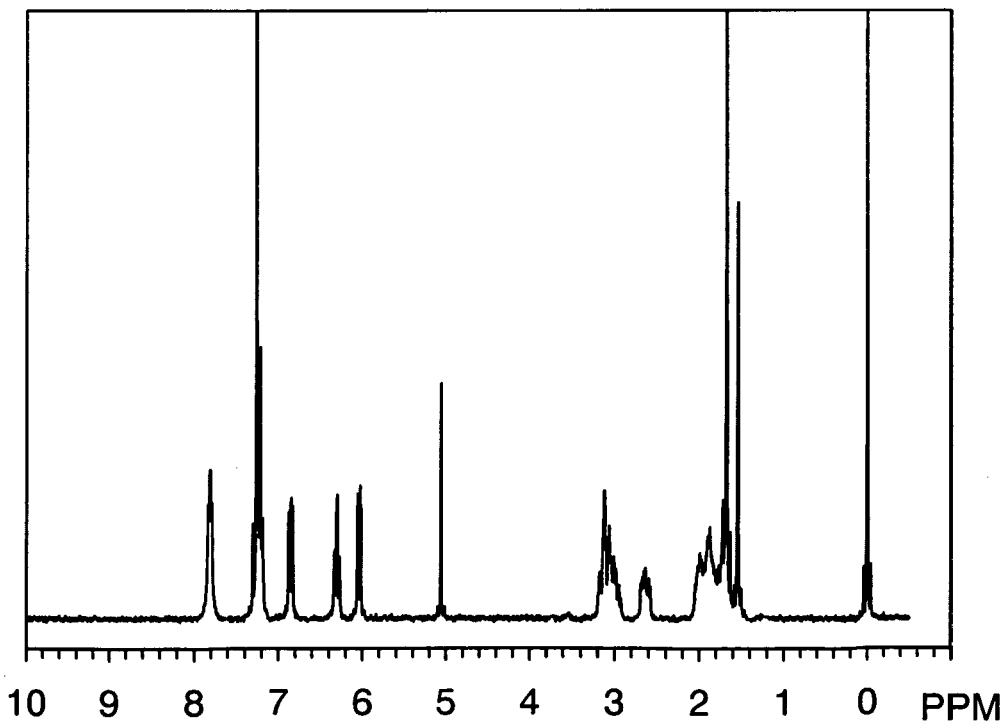

The obtained orange power was analyzed by nuclear magnetic resonance spectroscopy ($^1$H-NMR), and a result as described below was obtained. The obtained product was found to be Ir(FdpqtH)$_2$(acac) which is one of the organometallic complexes of the present invention and is represented by the structural formula (10). A result of analysis of $^1$H-NMR is shown below, and a chart of $^1$H-NMR is shown in FIGS. 20A and 20B. Note that FIG. 20B is a chart in which part of FIG. 20A is enlarged in a vertical direction.

$^1$H-NMR. δ(CDCl$_3$): 7.81 (t, 4H), 7.21 (m, 4H), 6.85 (m, 2H), 6.30 (td, 2H), 6.03 (dd, 2H), 5.06 (s, 1H), 3.18-2.93 (m, 6H), 2.67-2.58 (m, 2H), 1.99-1.77 (m, 8H), 1.68 (s, 6H).

A decomposition temperature T$_d$ of the obtained organometallic complex Ir(FdpqtH)$_2$(acac) of the present invention was measured by TG/DTA, and it was found that T$_d$=332° C. and the obtained product showed favorable heat resistance.

Figure 21:
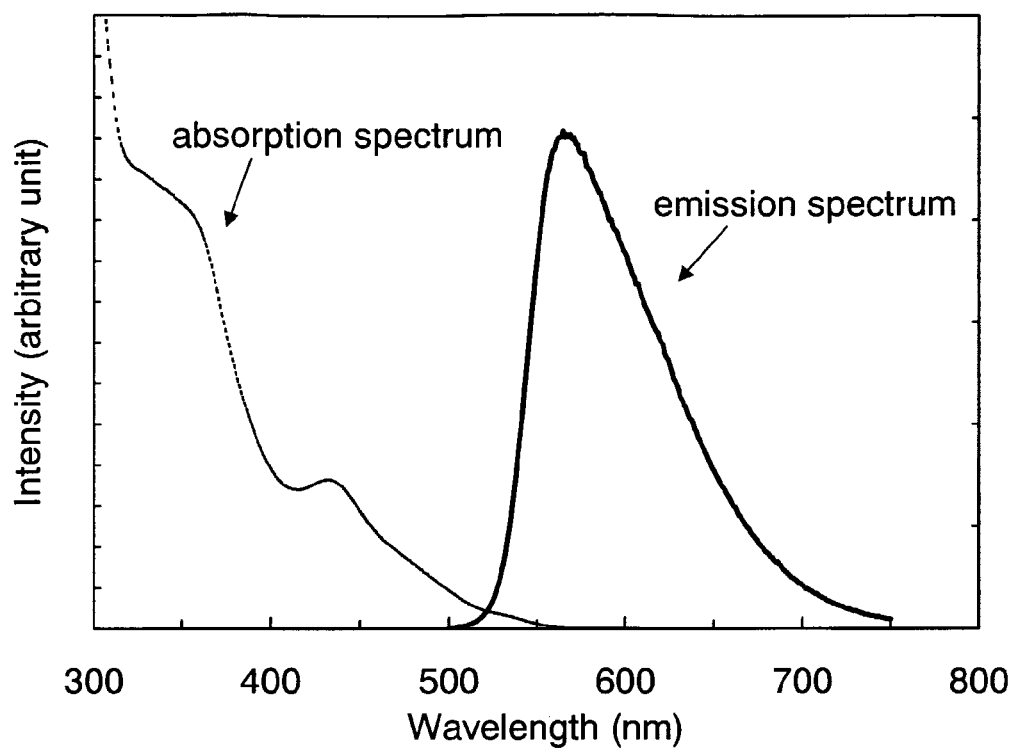
FIG. 21 is a graph showing an absorption spectrum and an emission spectrum of an organometallic complex synthesized in Synthesis Example 4.

Subsequently, an absorption spectrum (an ultraviolet-visible light spectrophotometer, manufactured by Japan Spectroscopy Corporation, V550 type) and an emission spectrum (a fluorescence spectrophotometer, manufactured by Hamamatsu Photonics Corporation, FS 920) of Ir(FdpqtH)$_2$(acac) were measured at a room temperature using a dichloromethane solution which was degassed. The result is shown in FIG. 21. In FIG. 21, a horizontal axis indicates a wavelength (nm) and a vertical axis indicates absorption intensity (arbitrary unit). As shown in FIG. 21, the organometallic complex Ir(FdpqtH)$_2$(acac) of the present invention has absorption peaks at 295 nm, 357 nm, 432 nm, 475 nm, and 535 nm. Also, the light emission spectrum was yellow light emission which had a light emission peak at 565 nm.

SYNTHESIS EXAMPLE 5

In this synthesis example, (acetylacenato)[2,3-bis(4-fluorophenyl)-5,6,7,8-tetrahydroquinoxalinato]platinum(II) (abbreviation: Pt(FdpqtH)(acac)) which is one of the organometallic complexes of the present invention and is represented by a structural formula (35) will be described.

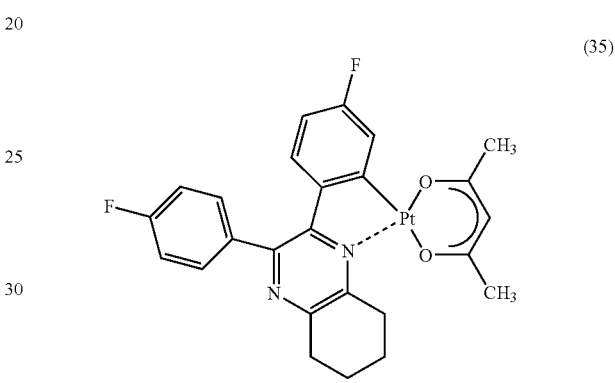

First, 2.15 g of the ligand Hfdpqt which was obtained in Step 1 of Synthesis Example 2 was mixed with 1.11 g of potassium tetrachloro platinate (K$_2$[PtCl$_4$]) by using a mixed solution of 30 mL of 2-ethoxyethanol and 10 mL of water. Next, the mixed solution was stirred with heat at 80° C. under a nitrogen atmosphere for 17 hours. The solvent was removed from the stirred solution, the obtained powder was washed with ethanol, and was dried overnight under reduced pressure. Subsequently, the dried powder, 0.41 mL of acetylacetone, and 1.42 g of sodium carbonate was mixed with 30 mL of 2-ethoxyethanol solution. Then, the mixed solution was refluxed under a nitrogen atmosphere for 16 hours. A deposit obtained by filtering the refluxed solution was washed with methanol, and was recrystallized by using dichloromethane; consequently, orange powder was obtained. A synthesis scheme (h-1) is shown next.

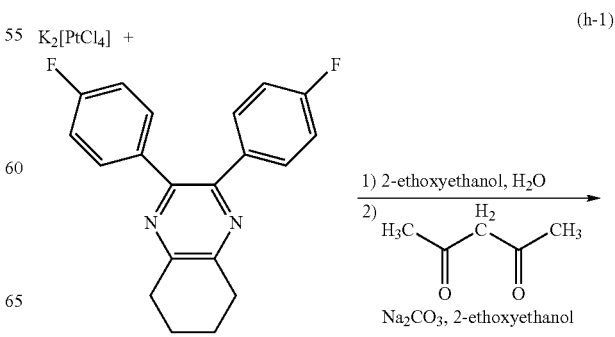

-continued

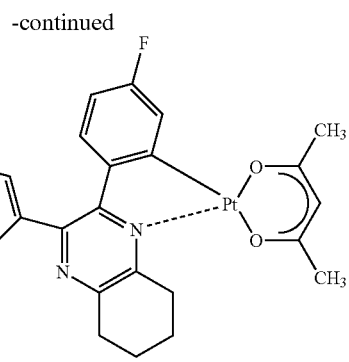

Figure 22A:
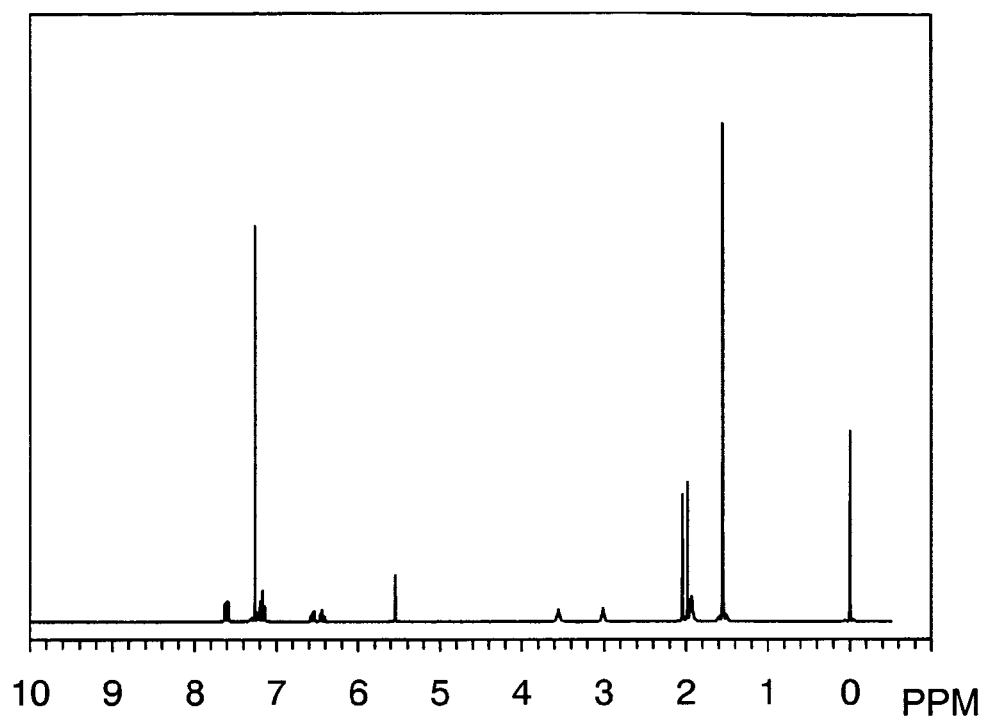
FIGS. 22A and 22B are charts obtained by analyzing an organometallic complex of the present invention synthesized in Synthesis Example 5 by using $^1$H-NMR.
Figure 22B:
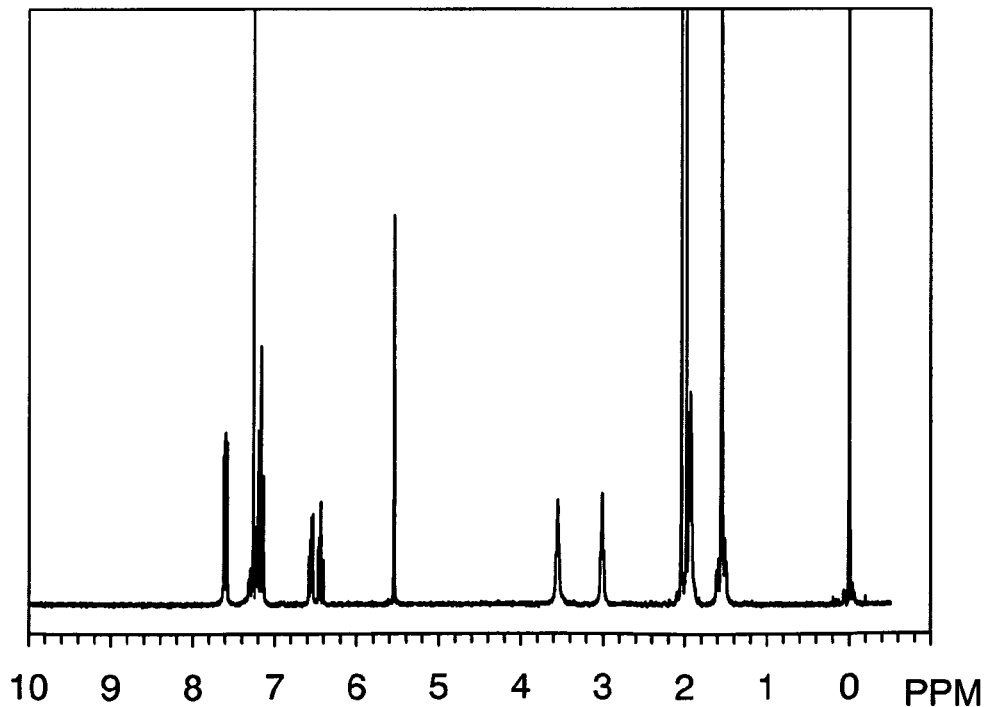

The obtained orange power was analyzed by nuclear magnetic resonance spectroscopy ($^1$H-NMR), and a result as described below was obtained. The obtained product was found to be Pt(FdpqtH)(acac) which is one of the organometallic complexes of the present invention and is represented by a structural formula (10). A result of analysis of $^1$H-NMR is shown below, and a chart of $^1$H-NMR is shown in FIGS. 22A and 22B. Note that FIG. 22B is a chart in which part of FIG. 22A is enlarged in a vertical direction.

$^1$H-NMR. δ(CDCl$_3$): 7.24 (m, 2H), 7.24-7.13 (m, 3H), 6.56 (dd, 1H), 6.44 (td, 1H), 5.55 (s, 1H), 3.56 (brm, 2H), 3.02 (brm, 2H), 2.04 (s, 3H), 1.98 (s, 3H), 1.94 (brm, 4H).

A decomposition temperature $T_d$ of the obtained organometallic complex Pt(FdpqtH)(acac) of the present invention was measured by TG/DTA, and it was found that $T_d$=239° C.

Figure 23:
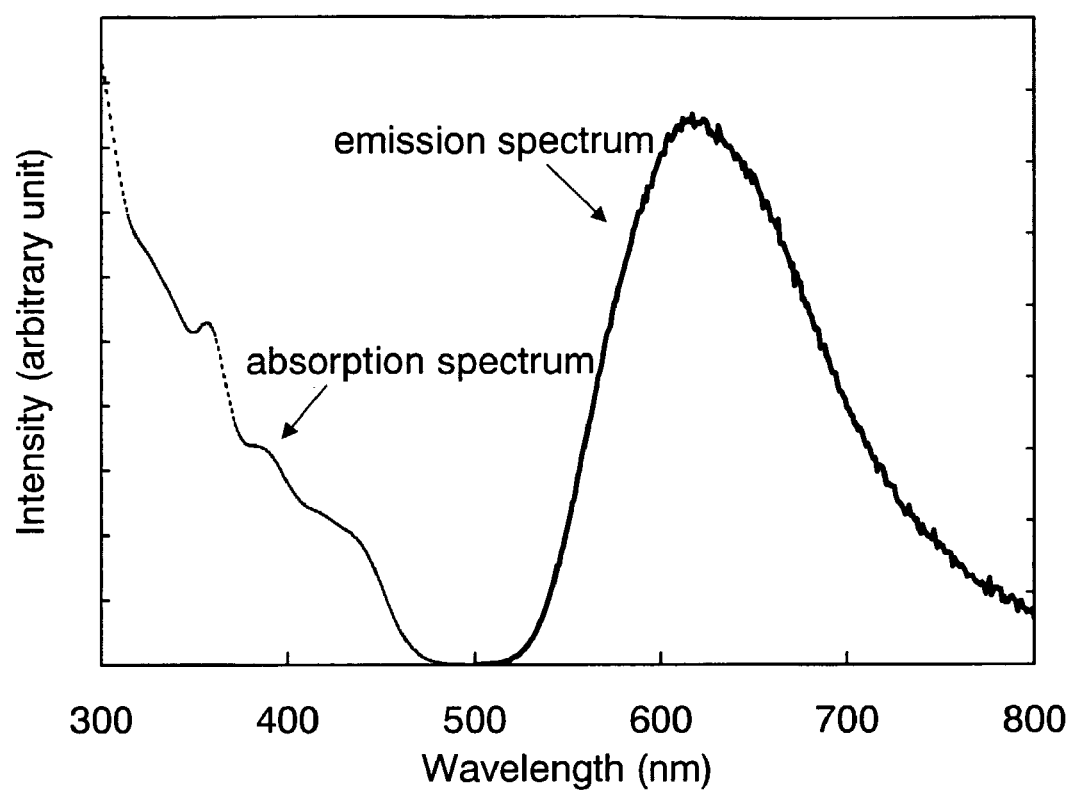
FIG. 23 is a graph showing an absorption spectrum and an emission spectrum of an organometallic complex synthesized in Synthesis Example 5.

Subsequently, an absorption spectrum (an ultraviolet-visible light spectrophotometer, manufactured by Japan Spectroscopy Corporation, V550 type) and an emission spectrum (a fluorescence spectrophotometer, manufactured by Hamamatsu Photonics Corporation, FS 920) of Pt(FdpqtH)(acac) were measured at a room temperature using a dichloromethane solution which was degassed. The result is shown in FIG. 23. In FIG. 23, the horizontal axis indicates a wavelength (nm) and the vertical axis indicates intensity (arbitrary unit). As shown in FIG. 23, the organometallic complex Pt(FdpqtH)(acac) of the present invention has absorption peaks at 324 nm, 357 nm, 389 nm, 439 nm, and 469 nm. Also, the light emission spectrum was orange-red light emission which had a light emission peak at 620 nm.

Embodiment 2

In this embodiment, a method for manufacturing a light-emitting element using Ir(dpqtH)$_2$(acac) synthesized by the method described in Synthesis Example 1 as a light-emitting substance, and an operational characteristic thereof will be described.

Figure 11:
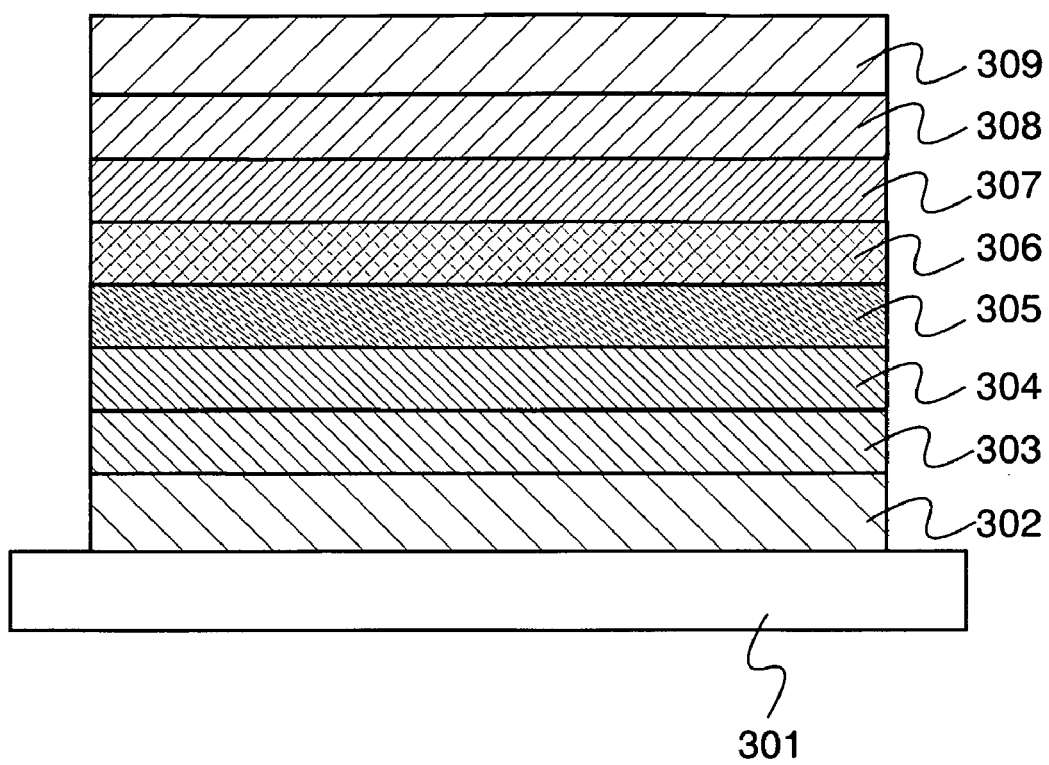
FIG. 11 is a view explaining a manufacturing method of a light-emitting element of Embodiment 1.

As shown in FIG. 11, indium tin oxide containing silicon oxide was deposited on a glass substrate 301 by a sputtering method, and a first electrode 302 was formed. The first electrode 302 was formed to have a thickness of 110 nm. Further, the electrode was formed to be square having a size of 2 mm×2 mm.

Subsequently, the glass substrate 301, on which the first electrode 302 was formed, was fixed to a holder provided in a vacuum evaporation apparatus so that a surface where the first electrode faced downward.

Subsequently, the air inside the vacuum evaporation apparatus was evacuated, and decompressed to be 1×10$^{-4}$ Pa, and thereafter, a first layer 303 containing NPB and molybdenum oxide was formed on the first electrode 302 by a co-evaporation method. In this embodiment, hexavalent molybdenum oxide (MoO$_3$) was used as molybdenum oxide. The first layer 303 was formed to be 50 nm thick. The molar ratio of NPB to molybdenum oxide was 1:2=NPB:molybdenum oxide. The first layer 303 functions as a hole generating layer when the light-emitting element is operated.

A second layer 304 containing NPB was formed on the first layer 303 by an evaporation method. The second layer 304 was formed to be 10 nm thick. The second layer 304 functions as a hole transporting layer when the light-emitting element is operated.

A third layer 305 containing CBP and Ir(dpqtH)$_2$(acac) was formed on the second layer 304 by a co-evaporation method. The third layer 305 was formed so as to be 30 nm thick and the mass ratio of CBP to Ir(dpqtH)$_2$(acac) was 1:0.025=CBP:Ir(dpqtH)$_2$(acac) (1:0.014=CBP:Ir(dpqtH)$_2$(acac), in being converted into the molar ratio). Consequently, Ir(dpqtH)$_2$(acac) is in such a state in which Ir(dpqtH)$_2$(acac) is dispersed in the layer containing CBP. The third layer 305 functions as a light-emitting layer when the light-emitting element is operated.

A fourth layer 306 containing BCP was formed on the third layer 305 by an evaporation method. The fourth layer 306 was formed to be 20 nm thick. The fourth layer 306 functions as a hole blocking layer when the light-emitting element is operated.

A fifth layer 307 containing Alq$_3$ was formed on the fourth layer 306 by an evaporation method. The fifth layer 307 was formed to be 30 nm thick. The fifth layer 307 functions as an electron transporting layer when the light-emitting element is operated.

A sixth layer 308 containing calcium fluoride was formed on the fifth layer 307 by an evaporation method. The sixth layer 308 was formed to be 1 nm thick. The sixth layer 308 functions as an electron injecting layer when the light-emitting element is operated.

A second electrode 309 containing aluminum was formed on the sixth layer 308. The second electrode 309 was formed to be 200 nm thick.

Current flows when voltage is applied to the light-emitting element manufactured as described above so that electric potential of the first electrode 302 is higher than that of the second electrode 309. Electrons and holes are recombined in the third layer 305 functioning as a light-emitting layer, and excited energy is generated. The excited Ir(dpqtH)$_2$(acac) emits light in returning to a ground state.

The light-emitting element was sealed in a globe box under a nitrogen atmosphere without being exposed to the atmospheric air. Thereafter, an operational characteristic of the light-emitting element was measured. Note that the measurement was carried out at a room temperature (under an atmosphere maintaining 25° C.).

Figure 12:
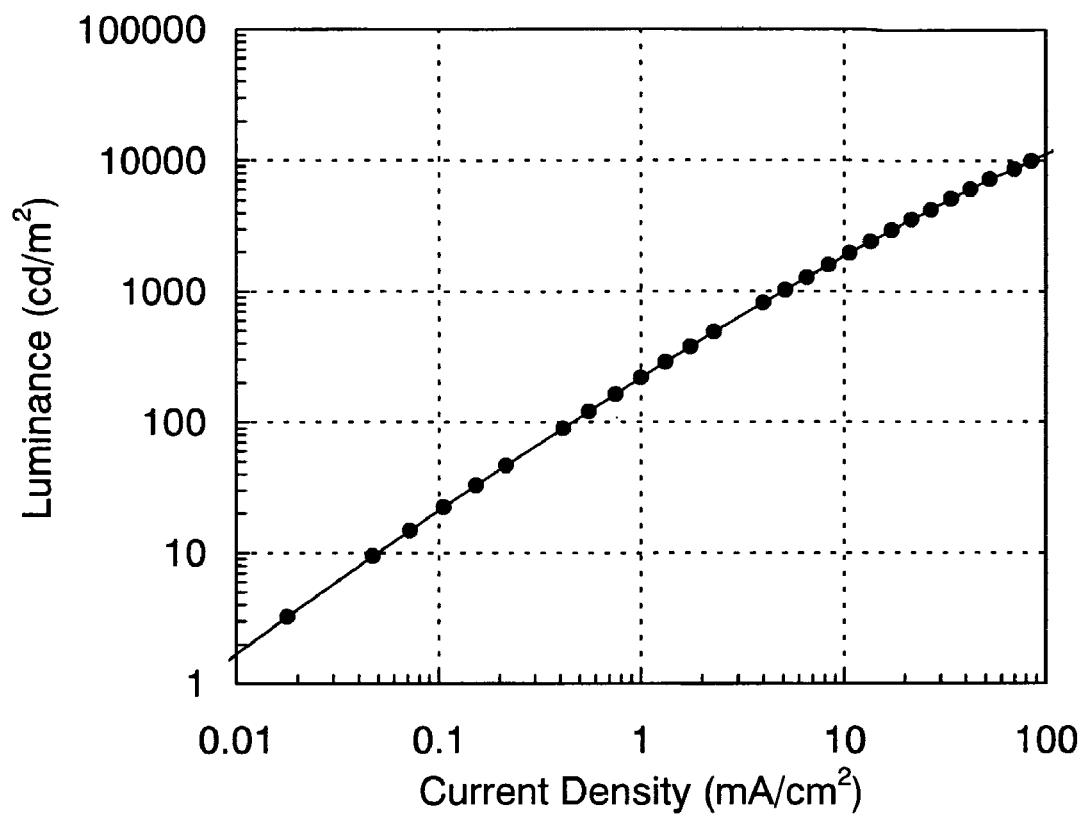
FIG. 12 is a graph showing a current density vs luminance characteristic when a light-emitting device of Embodiment 2 is operated.
Figure 13:
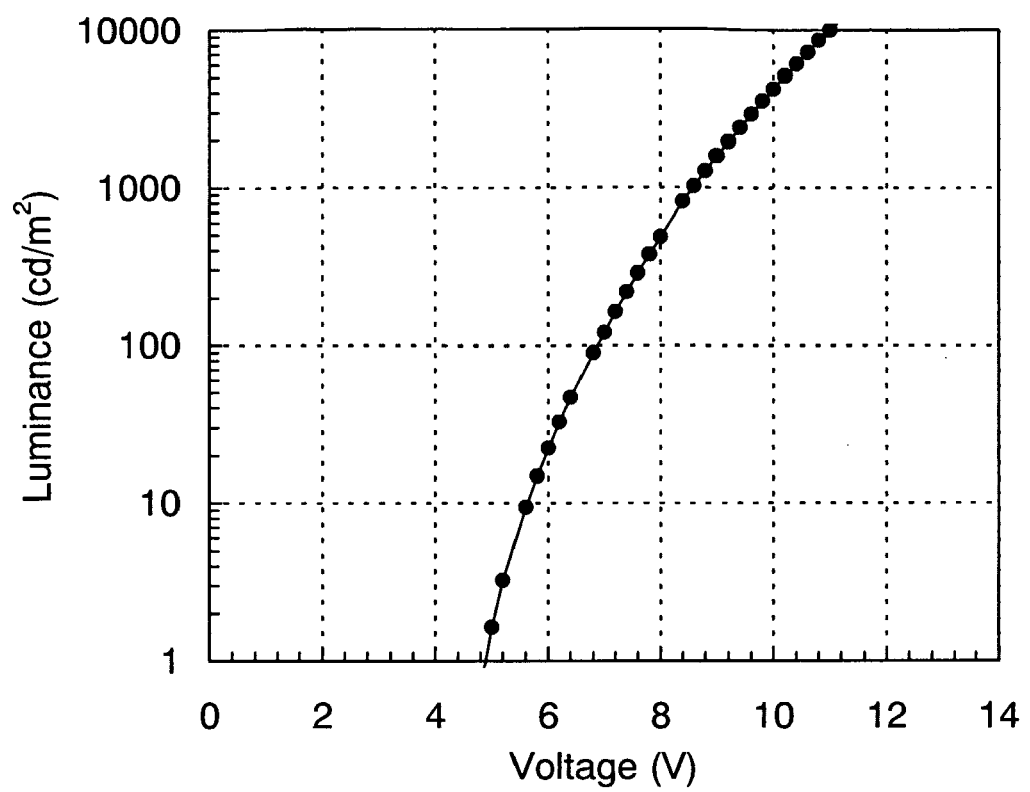
FIG. 13 is a graph showing a voltage vs luminance characteristic when a light emitting device of Embodiment 2 is operated.
Figure 14:
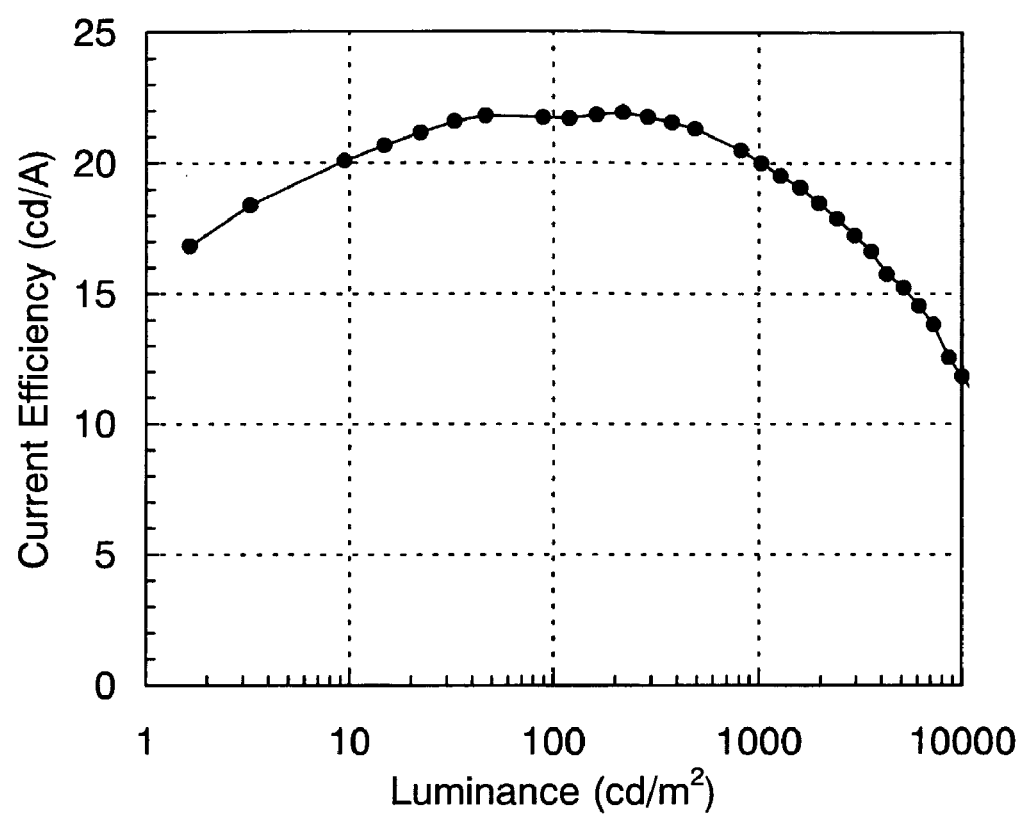
FIG. 14 is a graph showing a luminance vs current efficiency characteristic when a light-emitting device of Embodiment 2 is operated.

Measurement results are shown in FIGS. 12 to 14. FIG. 12 shows a measurement result of a current density-luminance characteristic, FIG. 13 shows a measurement result of a voltage-luminance characteristic, and FIG. 14 shows a measurement result of a luminance-current efficiency characteristic. In FIG. 12, a horizontal axis represents current density (mA/cm$^2$) and a vertical axis represents luminance (cd/m$^2$). In FIG. 13, a horizontal axis represents voltage (V) and a vertical axis represents luminance (cd/m$^2$). In FIG. 14, a horizontal axis represents luminance (cd/m$^2$) and a vertical axis represents current efficiency (cd/A). According to these results, it was found that current flows with the current density of 2.29 mA/cm$^2$ in the light-emitting element manufactured in this embodiment when voltage of 8V is applied, and the light-emitting element emits light with the luminance of 490 cd/m$^2$. Further, the current efficiency when the light-emitting element where light is emitted with the luminance of 490 cd/m² was 21 cd/A, and it was 10% in being converted into external quantum efficiency (the number of photons/the number of electrons). Applying the stacked structure as shown in this embodiment makes it possible to obtain favorable light emission derived from the organometallic complex of the present invention.

Figure 15:
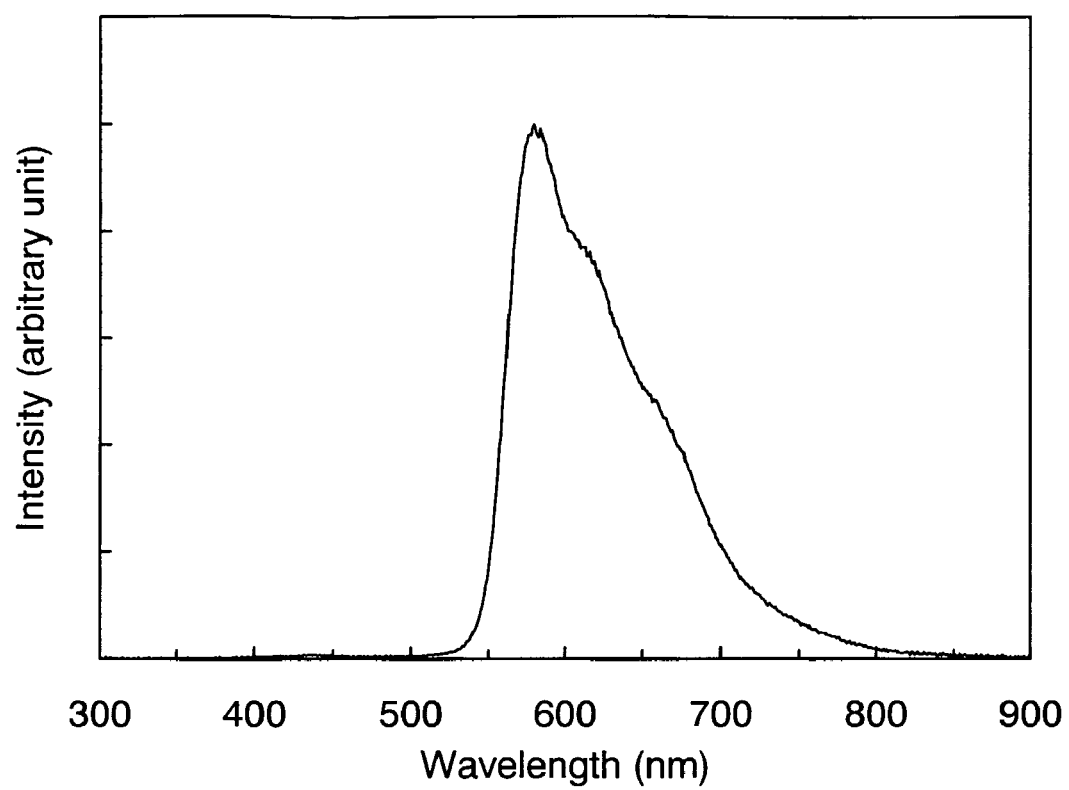
FIG. 15 is a graph showing an emission spectrum obtained when a light-emitting device of Embodiment 2 is operated.

Also, an emission spectrum of the light-emitting element manufactured in this embodiment is shown in FIG. 15. In FIG. 15, a horizontal axis represents a wavelength (nm) and a vertical axis represents intensity (arbitrary unit). According to FIG. 15, it was found that the light-emitting element of this embodiment has a peak of an emission spectrum at 580 nm and emits orange light.

Embodiment 3

In this embodiment, a method for manufacturing a light-emitting element using Ir(FdpqtH)$_2$(pic) synthesized in Synthesis Example 2 as a light-emitting substance and an operational characteristic thereof will be described with reference to FIGS. 24 and 25 to 28.

Figure 24:
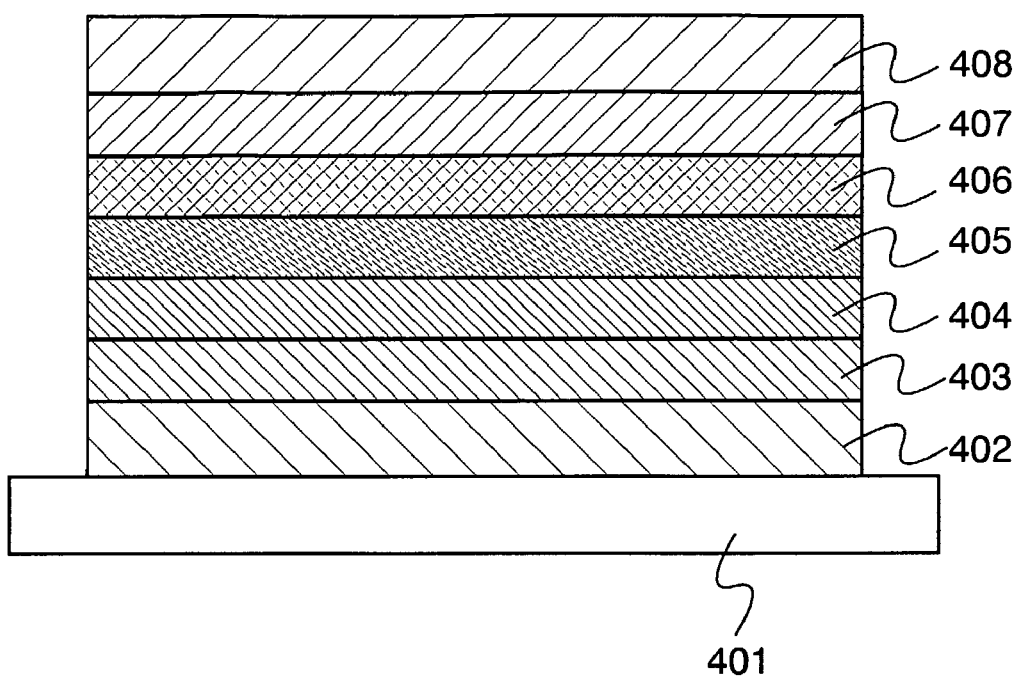
FIG. 24 is a view explaining a manufacturing method of a light emitting element of Embodiments 3 and 4.

As shown in FIG. 24, indium tin oxide containing silicon oxide was deposited on a glass substrate 401 by a sputtering method, and a first electrode 402 was formed. The first electrode 402 was formed to have a thickness of 110 nm.

Subsequently, the glass substrate 401, on which the first electrode 402 was formed, was fixed on a holder provided in a vacuum evaporation apparatus so that a surface where the first electrode faced downward.

The pressure inside the vacuum evaporation apparatus was reduced to be 1×10$^{-4}$ Pa, and thereafter, a first layer 403 containing DNTPD was formed on the first electrode 402. The first layer 403 was formed to be 50 nm thick. The first layer 403 functions as a hole injecting layer when the light-emitting element is operated.

A second layer 404 containing NPB was formed on the first layer 403 by an evaporation method. The second layer 404 was formed to be 10 nm thick. The second layer 404 functions as a hole transporting layer when the light-emitting element is operated.

A third layer 405 containing CBP and Ir(FdpqtH)$_2$(pic) was formed on the second layer 404 by a co-evaporation method. The third layer 405 was formed so as to be 30 nm thick and the mass ratio of CBP to Ir(FdpqtH)$_2$(pic) was 1:0.05=CBP:Ir(FdpqtH)$_2$(pic). Consequently, Ir(FdpqtH)$_2$(pic) is in such a state in which Ir(FdpqtH)$_2$(pic) is contained in a layer having CBP as a matrix. The third layer 405 functions as a light-emitting layer when the light-emitting element is operated. In such a case, Ir(FdpqtH)$_2$(pic) is referred to as a guest, and CBP is referred to as a host.

The fourth layer 406 containing BCP is formed on the third layer 405 by an evaporation method. The fourth layer 406 was formed to be 20 nm thick. The fourth layer 406 functions as an electron transporting layer when the light-emitting element is operated.

A fifth layer 407 containing Alq$_3$ and Li was formed on the fourth layer 406 by a co-evaporation method. The fifth layer 407 was formed so as to be 30 nm thick and mass ratio of Alq$_3$ to Li was 1:0.01=Alq$_3$:Li. The fifth layer 407 functions as an electron injecting layer when the light-emitting element is operated.

A second electrode 408 containing aluminum was formed on the fifth layer 407. The second electrode 408 was formed to be 200 nm thick.

Current flows when voltage is applied to the light-emitting element manufactured as described above so that electric potential of the first electrode 402 is higher than that of the second electrode 408. Electrons and holes are recombined in the third layer 405 functioning as a light-emitting layer, and excited energy is generated. The excited Ir(FdpqtH)$_2$(pic) emits light in returning to a ground state.

The light-emitting element was sealed in a globe box under a nitrogen atmosphere without being exposed to the atmospheric air. Thereafter, an operational characteristic of the light-emitting element was measured. Note that the measurement was carried out at a room temperature (under an atmosphere maintaining 25° C.).

Figure 25:
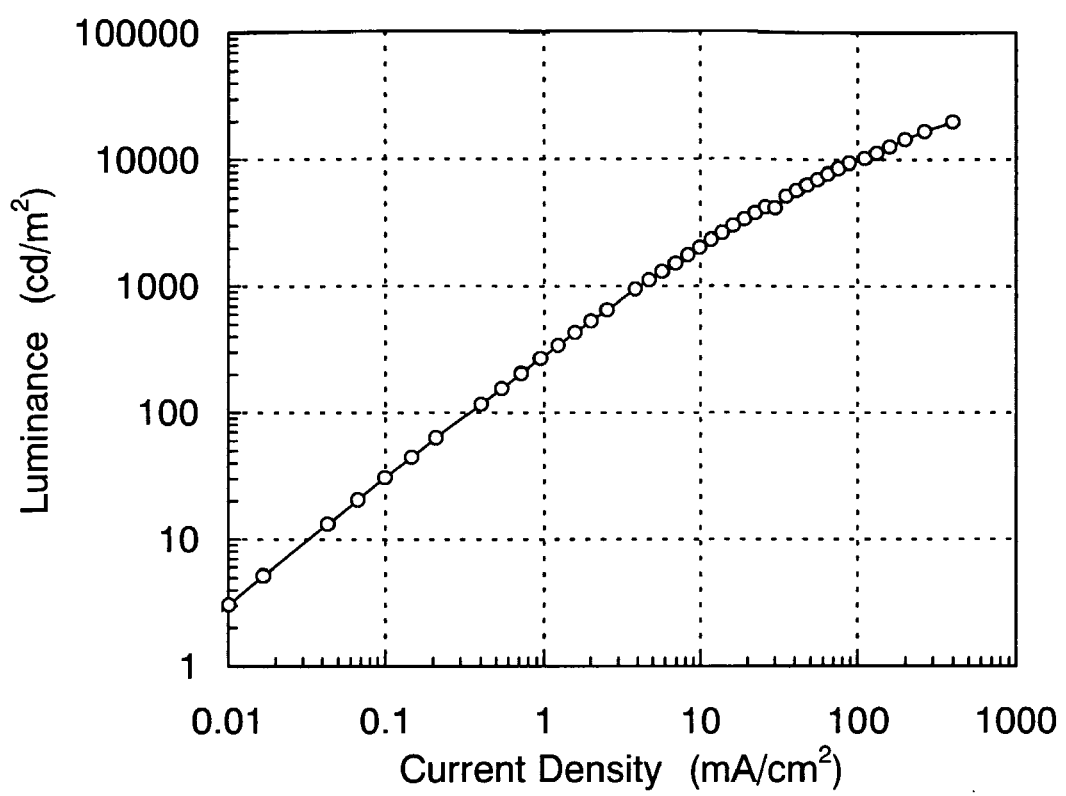
FIG. 25 is a graph showing a current density vs luminance characteristic when a light-emitting device of Embodiment 3 is operated.
Figure 26:
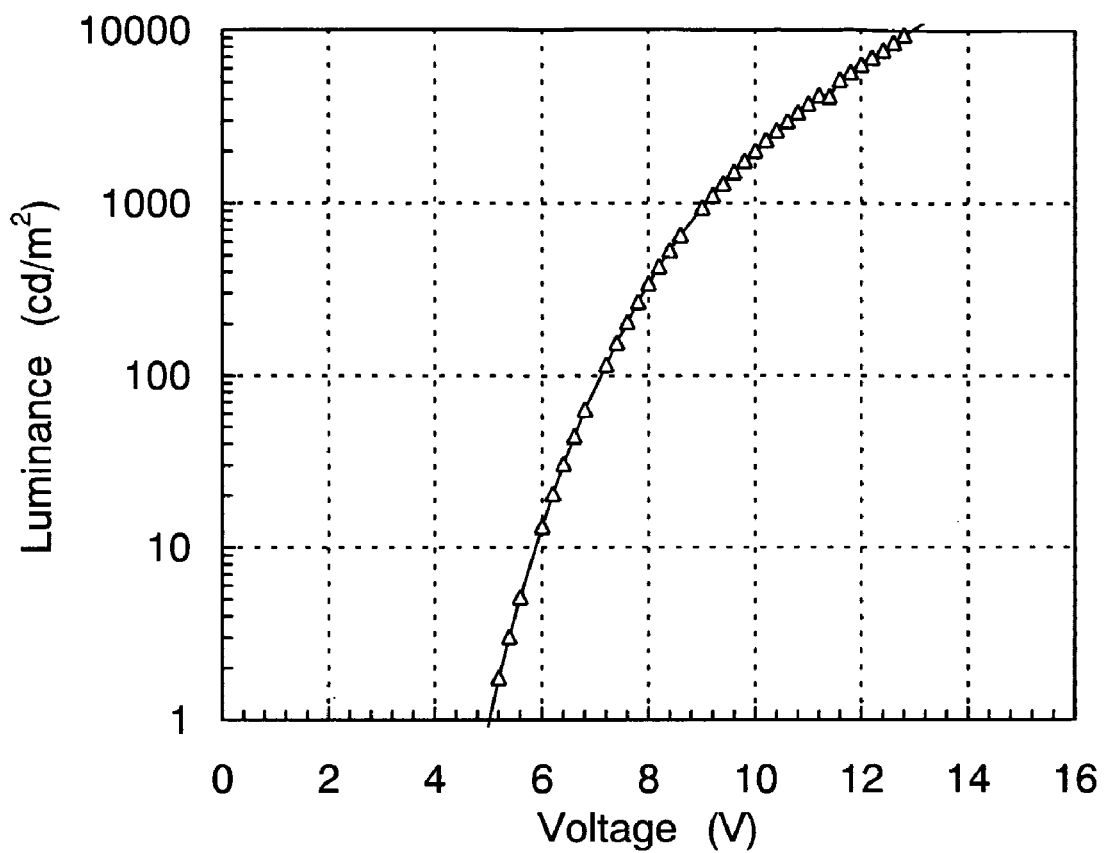
FIG. 26 is a graph showing a voltage vs luminance characteristic when a light-emitting device of Embodiment 3 is operated.
Figure 27:
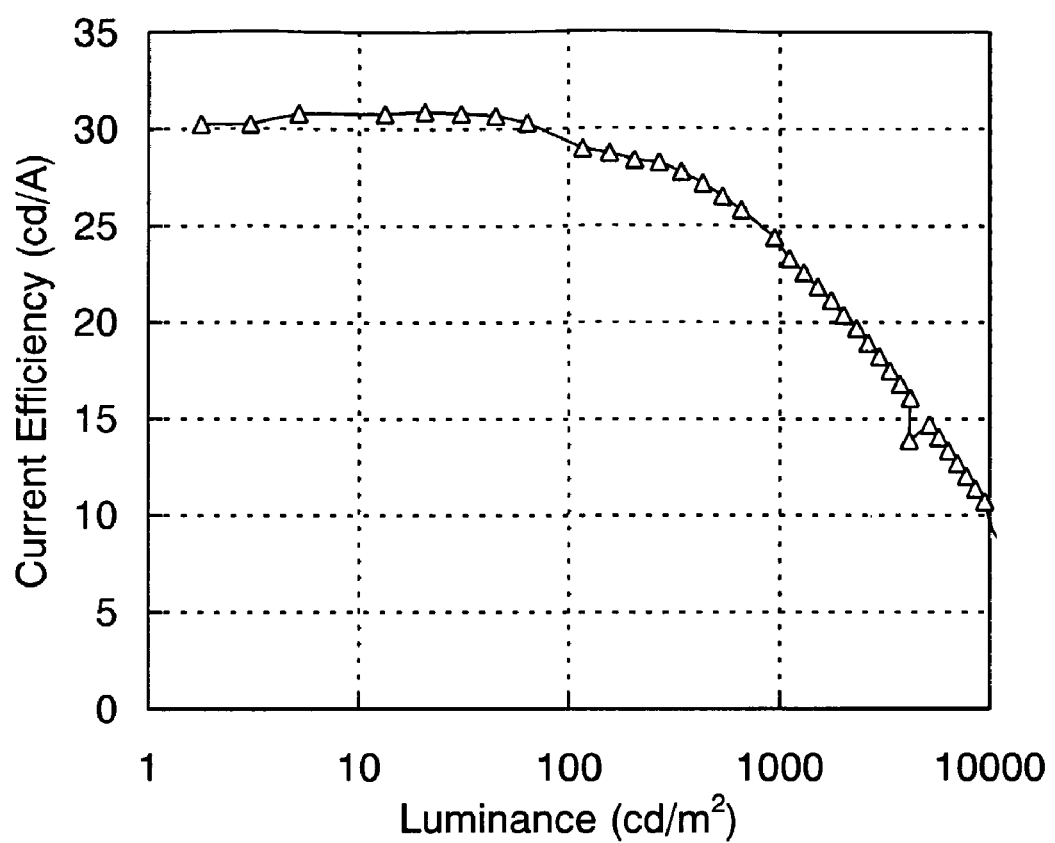
FIG. 27 is a graph showing a luminance vs current efficiency characteristic when a light-emitting device of Embodiment 3 is operated.

Measurement results are shown in FIGS. 25 to 27. FIG. 25 shows a measurement result of a current density-luminance characteristic, FIG. 26 shows a measurement result of a voltage-luminance characteristic, and FIG. 27 shows a measurement result of a luminance-current efficiency characteristic. In FIG. 25, a horizontal axis represents current density (mA/cm²) and a vertical axis represents luminance (cd/m²). In FIG. 26, a horizontal axis represents voltage (V) and a vertical axis represents luminance (cd/m²). In FIG. 27, a horizontal axis represents luminance (cd/m²) and a vertical axis represents current efficiency (cd/A). According to these results, it was found that the light-emitting element of this embodiment emits light with the current density of 3.86 mA/cm² and with the luminance of 942 cd/m² when voltage of 9V is applied. The current efficiency at this time was 24.4 cd/A, and external, quantum efficiency was 10.8%, which was high. Furthermore, when the light-emitting element where light is emitted with the luminance of 20.6 cd/m², the external quantum efficiency was 13.7%, which was a maximum value.

Figure 28:
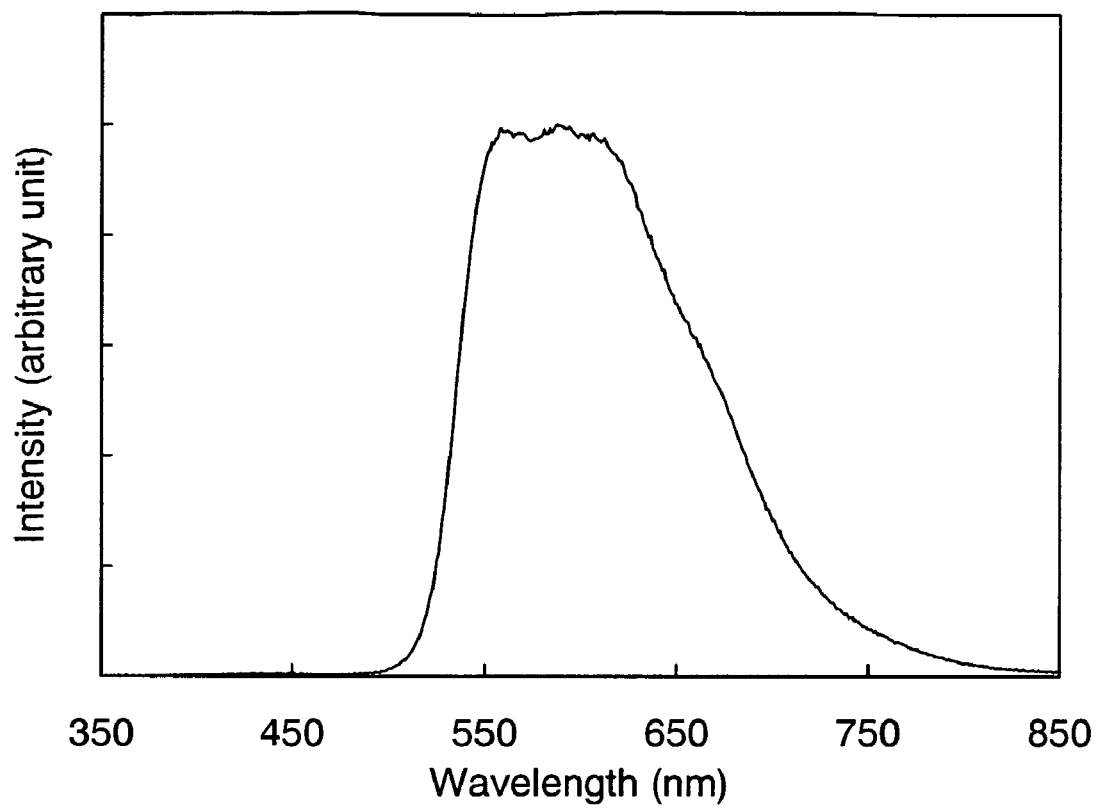
FIG. 28 is a graph showing an emission spectrum obtained when a light-emitting device of Embodiment 3 is operated.

Light emission spectrum of the light-emitting element manufactured in this embodiment is shown in FIG. 28. In FIG. 28, a horizontal axis represents a wavelength (nm) and a vertical axis represents intensity (arbitrary unit). Furthermore, CIE chromaticity coordinate was x=0.51, and y=0.48, and it was found that the light-emitting element of this embodiment represented yellow light.

Further, as shown in FIG. 28, the trapezoidal shaped light emission spectrum (half width=140 nm) which has less change in light emission intensity in a range of wavelengths of 550 to 650 nm can be obtained from the light-emitting element of this embodiment. Therefore, white light can be obtained by combining the light-emitting element of this embodiment with a light-emitting element showing a gentle peak shaped light emission spectrum which has less change in light emission intensity in a range of wavelengths of 450 to 550 nm so that the light emission spectrum is synthesized (for example, these light-emitting elements are made to emit light concurrently). Furthermore, white light can be obtained by providing a layer containing a light-emitting substance showing a gentle peak shaped light emission spectrum which has less change in light emission intensity in a range of wavelengths of 450 to 550 nm in the light-emitting element of this embodiment, and forming a layer provided between the electrodes so that Ir(FdpqtH)$_2$(pic) and the light-emitting substance emit light concurrently.

Embodiment 4

In this embodiment, an operational characteristic of a light-emitting element using Ir(FdpqtH)$_2$(bpz$_4$) synthesized in Synthesis Example 3 as a light-emitting substance will be described with reference to FIGS. 29 to 32.

The light-emitting element manufactured in this embodiment is different from the light-emitting element in Embodiment 3, in terms of using Ir(FdpqtH)$_2$(bpz$_4$) instead of Ir(FdpqtH)$_2$(pic); however, structures other than that (a substance, thickness, mass ratio, and the like used for forming each layer) are the same as Embodiment 3. Therefore, Embodiment 3 is referred to for a manufacturing method and an element composition, and the description is omitted here.

Figure 29:
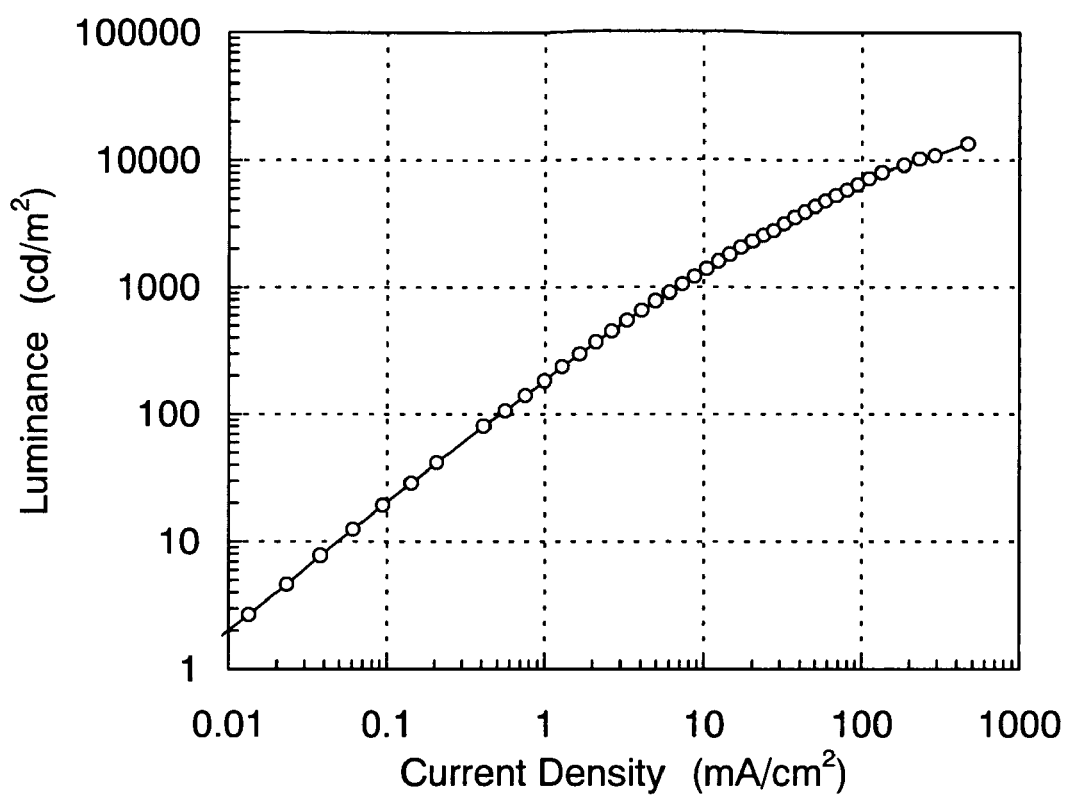
FIG. 29 is a graph showing a current density vs luminance characteristic when a light-emitting device of Embodiment 4 is operated.
Figure 30:
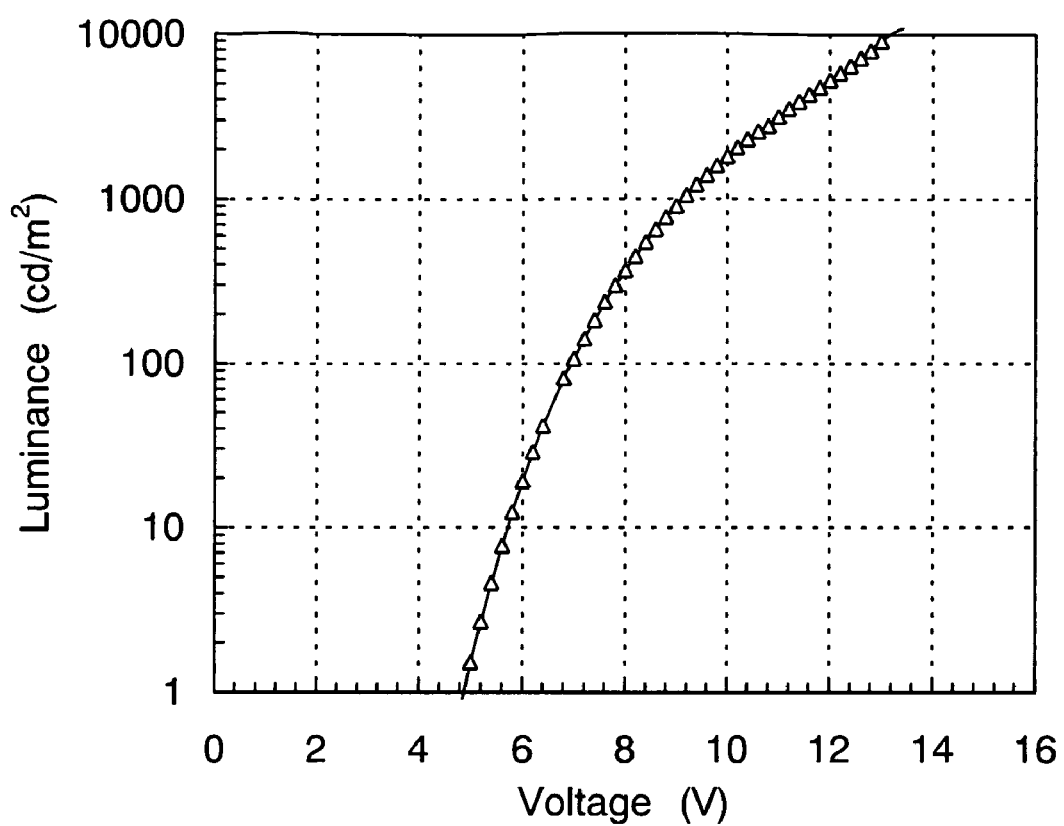
FIG. 30 is a graph showing a voltage vs luminance characteristic when a light-emitting device of Embodiment 4 is operated.
Figure 31:
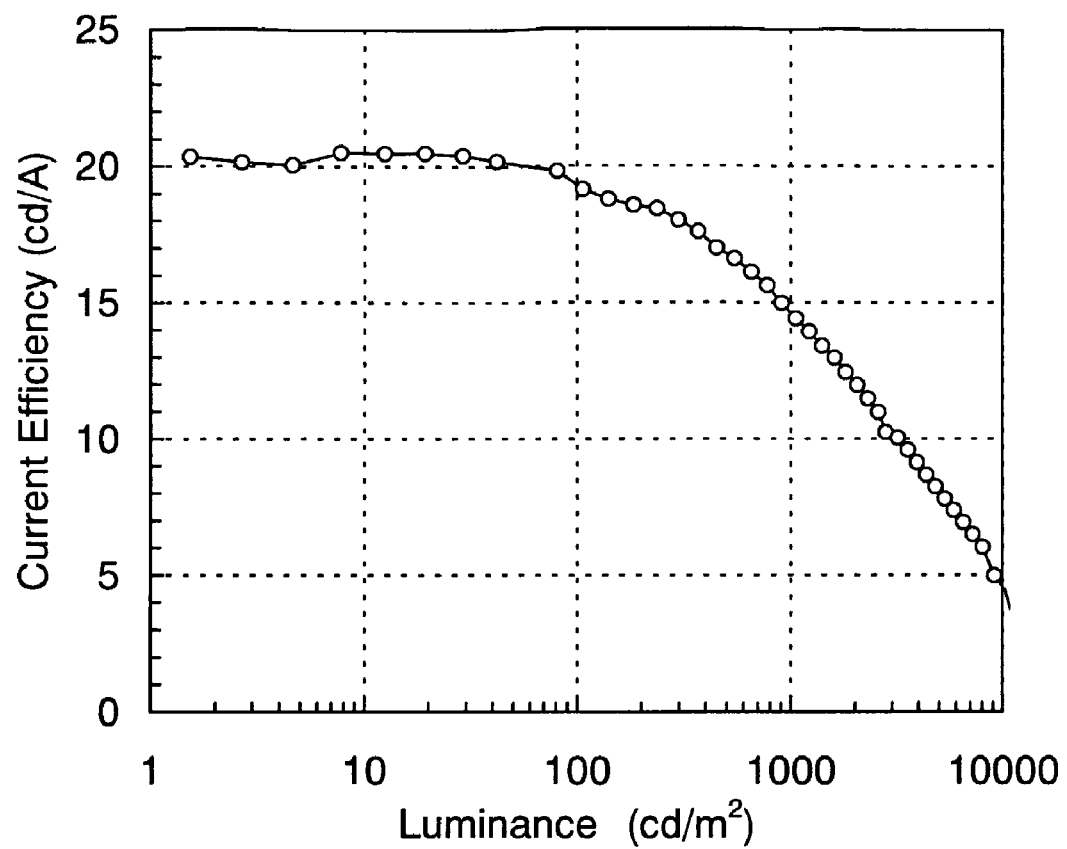
FIG. 31 is a graph showing a luminance vs current efficiency characteristic when a light-emitting device of Embodiment 4 is operated.

Measurement results of operational characteristics of the manufactured light-emitting element are shown in FIGS. 29 to 31. FIG. 29 shows a measurement result of a current density-luminance characteristic, FIG. 30 shows a measurement result of a voltage-luminance characteristic, and FIG. 31 shows a measurement result of a luminance-current efficiency characteristic. In FIG. 29, a horizontal axis represents current density (mA/cm$^2$) and a vertical axis represents luminance (cd/m$^2$). In FIG. 30, a horizontal axis represents voltage (V) and a vertical axis represents luminance (cd/m$^2$). In FIG. 31, a horizontal axis represents luminance (cd/m$^2$) and a vertical axis represents current efficiency (cd/A). According to these results, it was found that the light-emitting element of this embodiment emits light with the current density of 7.29 mA/cm$^2$ and with the luminance of 1050 cd/m$^2$ when voltage 9.2V is applied. The current efficiency at this time was 14.4 cd/A, and external quantum efficiency was 7.76%, which was high. Furthermore, when the light-emitting element where light is emitted with the luminance of 7.78 cd/m$^2$, the external quantum efficiency was 11.0%, which was a maximum value.

Figure 32:
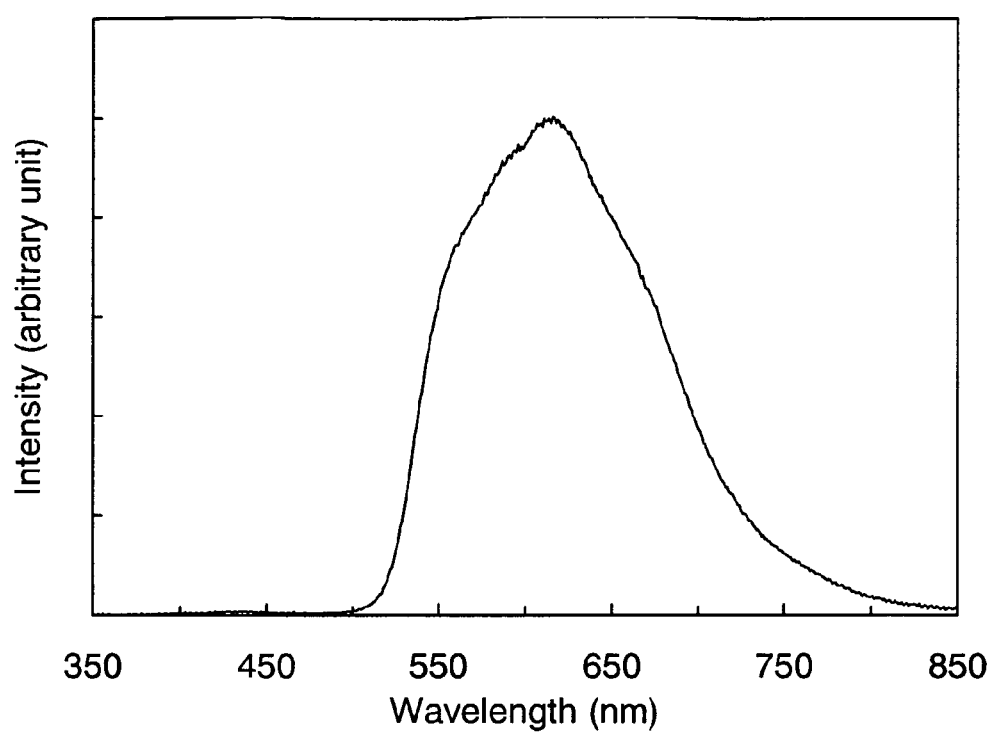
FIG. 32 is a graph showing an emission spectrum obtained when a light-emitting device of Embodiment 4 is operated.

A light emission spectrum of the light-emitting element manufactured in this embodiment is shown in FIG. 32. In FIG. 32, a horizontal axis represents a wavelength (nm) and a vertical axis represents intensity (arbitrary unit). Furthermore, CIE chromaticity coordinate was x=0.54, and y=0.45, and it was found that the light-emitting element of the present invention represented yellow-orange light.

Further, as shown in FIG. 32, a gentle peak shaped light emission spectrum (half width=145 nm) which has less change in light emission intensity in a range of wavelengths of 550 to 650 nm can be obtained from the light-emitting element of this embodiment. Therefore, white light can be obtained by combining the light-emitting element of this embodiment with a light-emitting element showing a gentle peak shaped light emission spectrum which has wide peak in a range of wavelengths of 450 to 550 nm so that the light emission spectrum is synthesized (for example, these light-emitting elements are made to emit light concurrently). Furthermore, white light can be obtained by providing a layer containing a light-emitting substance showing peak shaped light emission spectrum which has less change in light emission intensity in a range of wavelengths of 450 to 550 nm in the light-emitting element of this embodiment, and forming a layer provided between electrodes so that Ir(FdpqtH)$_2$(bpz$_4$) and the light-emitting substance emit light concurrently.

Embodiment 5

In this embodiment, a method for manufacturing a light-emitting element using Ir(FdpqtH)$_2$(acac) synthesized in Synthesis Example 4 as a light-emitting substance and an operational characteristic thereof will be described with reference to FIGS. 24 and 33 to 36.

As shown in FIG. 24, indium tin oxide containing silicon oxide was deposited on a glass substrate 401 by a sputtering method, and a first electrode 402 was formed. The first electrode 402 was formed to be 110 nm thick.

The glass substrate 401 on which the first electrode 402 was formed was fixed on a holder provided in a vacuum evaporation apparatus so that a surface where the first electrode 402 was formed faced downward.

The pressure in the vacuum evaporation apparatus was reduced to be 1×10$^{-4}$ Pa, and thereafter, a first layer 403 containing NPB and molybdenum oxide was formed on the first electrode 402 by a co-evaporation method. In this embodiment, hexavalent molybdenum oxide (MoO$_3$) was used as molybdenum oxide. The first layer 403 was formed to be 50 nm thick. The molar ratio of NPB to molybdenum oxide was 1:1=NPB:molybdenum oxide. The first layer 403 functions as a hole generating layer when the light-emitting element is operated.

A second layer 404 containing TCTA was formed on the first layer 403 by an evaporation method. The second layer 404 was formed to be 10 nm thick. The second layer 404 functions as a hole transporting layer when the light-emitting element is operated.

A third layer 405 containing CBP and Ir(FdpqtH)$_2$(acac) was formed on the second layer 404 by a co-evaporation method. The third layer 405 was formed so as to be 30 nm thick, and the mass ratio of CBP to Ir(FdpqtH)$_2$(acac) was 1:0.01=CBP:Ir(FdpqtH)$_2$(acac). Consequently, Ir(FdpqtH)$_2$(acac) is in such a state in which Ir(FdpqtH)$_2$(acac) is contained in a layer having CBP as a matrix. The third layer 405 functions as a light-emitting layer when the light-emitting element is operated. In such a case, Ir(FdpqtH)$_2$(acac) is referred to as a guest, and CBP is referred to as a host.

A fourth layer 406 was containing TAZ formed on the third layer 405 by an evaporation method. The fourth layer 406 was formed to be 20 nm thick. The fourth layer 406 functions as an electron transporting layer when the light-emitting element is operated.

A fifth layer 407 containing TAZ and Li was formed on the fourth layer 406 by a co-evaporation method. The fifth layer 407 is formed to be 30 nm thick. Mass ratio of TAZ to Li was set to be 1:0.01=TAZ:Li. The fifth layer 407 functions as an electron injecting layer when the light-emitting element is operated.

A second electrode 408 containing aluminum was formed on the fifth layer 407. The second electrode 408 was formed to be 200 nm thick.

Current flows when voltage is applied to the light-emitting element manufactured as described above so that electric potential of the first electrode 402 is higher than that of the second electrode 408. Electrons and holes are recombined in the third layer 405 functioning as a light-emitting layer, and excited energy is generated. The excited Ir(FdpqtH)$_2$(acac) emits light in returning to a ground state.

The light-emitting element was sealed in a sealing apparatus under a nitrogen atmosphere without being exposed to the atmospheric air. Thereafter, an operational characteristic of the light-emitting element was measured. Note that the measurement was carried out at a room temperature (under an atmosphere maintaining 25° C.).

Figure 33:
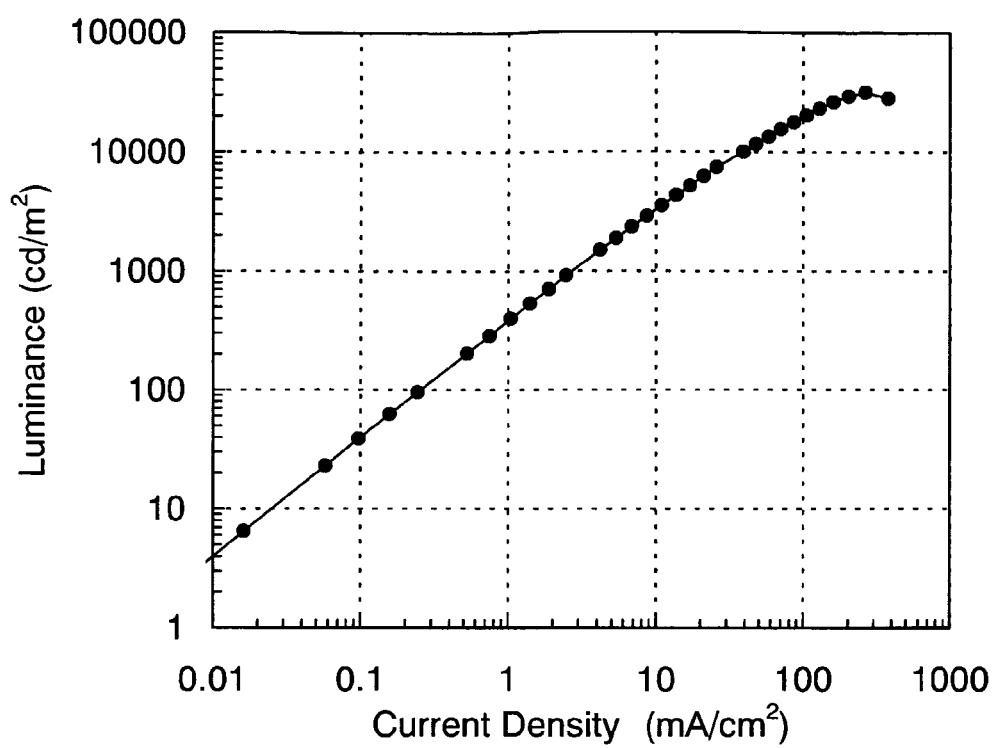
FIG. 33 is a graph showing a current density vs luminance characteristic when a light-emitting device of Embodiment 5 is operated.
Figure 34:
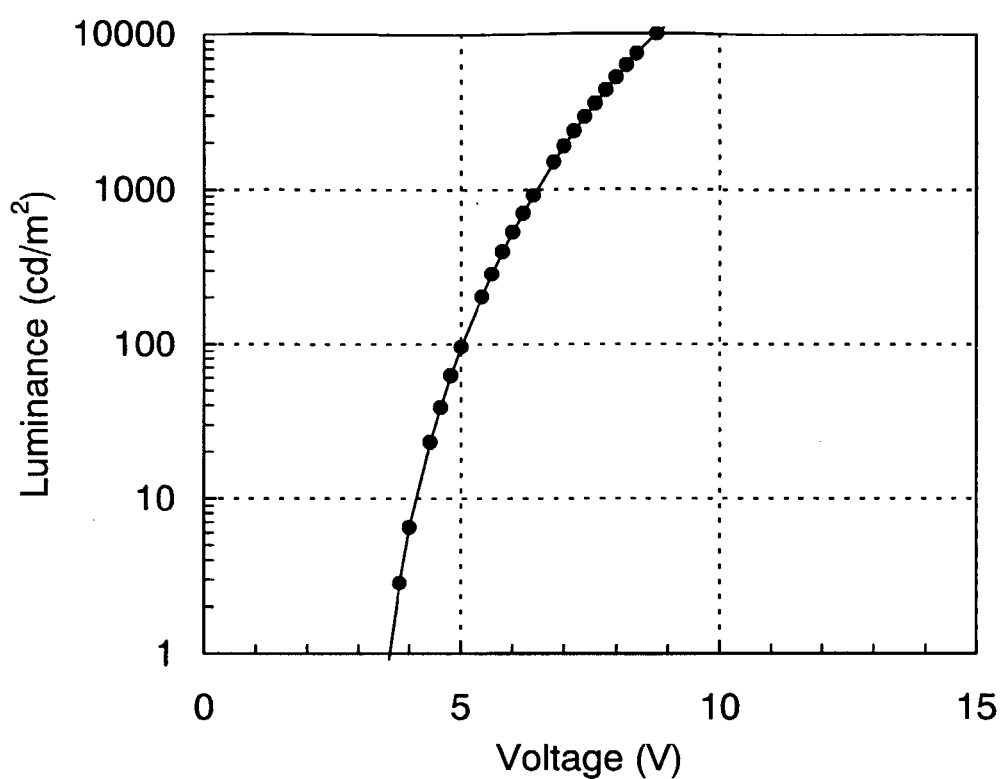
FIG. 34 is a graph showing a voltage vs luminance characteristic when a light-emitting device of Embodiment 5 is operated.
Figure 35:
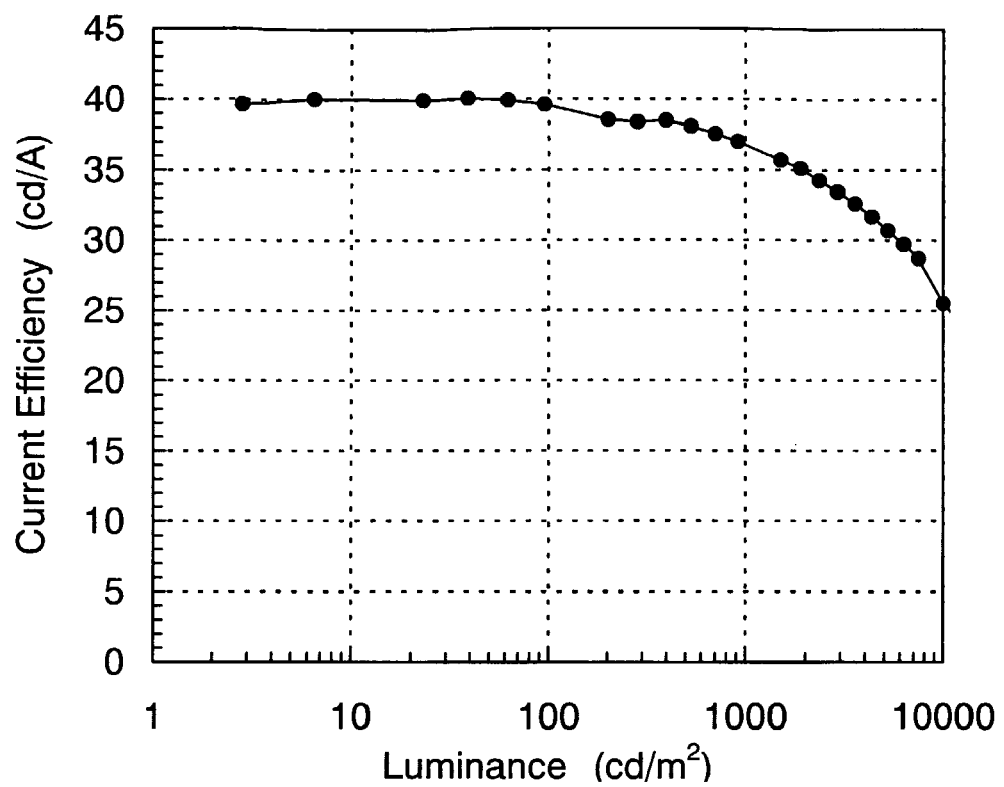
FIG. 35 is a graph showing a luminance vs current efficiency characteristic when a light-emitting device of Embodiment 5 is operated.

Measurement results are shown in FIGS. 33 to 35. FIG. 33 shows a measurement result of a current density-luminance characteristic, FIG. 34 shows a measurement result of a voltage-luminance characteristic, and FIG. 35 shows a measurement result of a luminance-current efficiency characteristic. In FIG. 33, a horizontal axis represents current density (mA/cm$^2$) and a vertical axis represents luminance (cd/m$^2$). In FIG. 34, a horizontal axis represents voltage (V) and a vertical axis represents luminance (cd/m$^2$). In FIG. 35, a horizontal axis represents luminance (cd/m$^2$) and a vertical axis represents current efficiency (cd/A). According to these results, it was found that current flows with the current density of 2.47 mA/cm$^2$ in the light-emitting element of this embodiment, and the light-emitting element emits light with the luminance of 915 cd/m$^2$ when voltage of 6.4V is applied. The current efficiency at this time was 37.0 cd/A, and external quantum efficiency was 13.8%, which was high. Furthermore, when the light-emitting element where light is emitted with the luminance of 38.7 cd/m², the external quantum efficiency was 15.0%, which was a maximum value.

Figure 36:
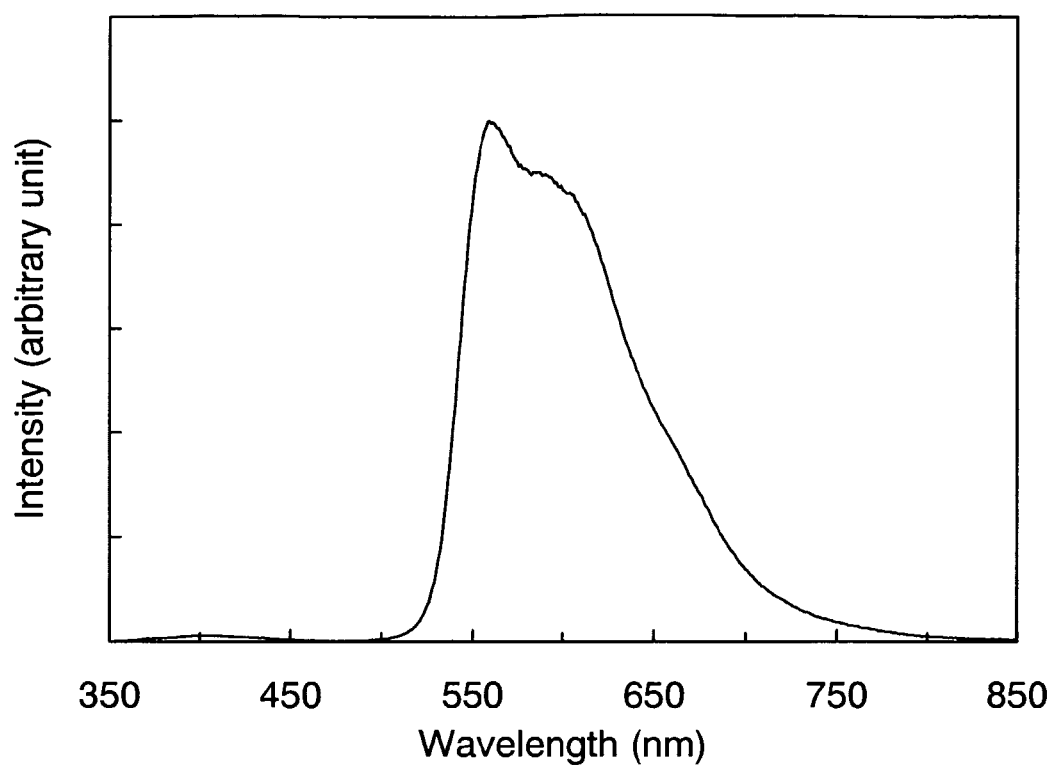
FIG. 36 is a graph showing an emission spectrum obtained when a light-emitting device of Embodiment 5 is operated.

A light emission spectrum of the light-emitting element manufactured in this embodiment is shown in FIG. 36. In FIG. 36, a horizontal axis represents a wavelength (nm) and a vertical axis represents intensity (arbitrary unit). Furthermore, CIE chromaticity coordinate was x=0.52, and y=0.48, and it was found that the light-emitting element of the present invention represented yellow light.

Further, as shown in FIG. 36, a gentle peak shaped light emission spectrum (half width=100 nm) which has less change in light emission intensity in a range of wavelengths of 550 to 650 nm can be obtained from the light-emitting element of this embodiment. Therefore, white light can be obtained by combining the light-emitting element of this embodiment with a light-emitting element showing a gentle peak shaped light emission spectrum which has less change in light emission intensity in a range of wavelengths of 450 to 550 nm so that the light emission spectrum is synthesized (for example, these light-emitting elements are made to emit light concurrently). Furthermore, white light can be obtained by providing a layer containing a light-emitting substance showing a gentle peak shaped light emission spectrum which has less change in light emission intensity in a range of wavelengths of 450 to 550 nm in the light-emitting element of this embodiment, and forming a layer provided between electrodes so that $Ir(FdpqtH)_2(acac)$ and the light-emitting substance emit light concurrently.

This application is based on Japanese Patent Application serial no. 2005-091349 filed in Japan Patent Office on 28, Mar. 2005 and Japanese Patent Application serial no. 2005-324037 filed in Japan Patent Office on 8, Nov. 2005, the entire contents of which are hereby incorporated by reference.

The invention claimed is

1. An organometallic complex including a structure represented by a general formula (1),

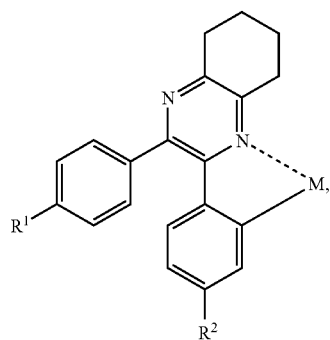

(1)

wherein each of $R^1$ and $R^2$ represents any one of hydrogen, an alkyl group, a halogen group, —$CF_3$, an alkoxy group, and an aryl group, and wherein M represents an element that belongs to Group 9 or Group 10.

2. A light emitting element comprising a layer formed between a pair of electrodes, wherein the layer comprises the organometallic complex according to claim 1.

3. A light emitting device comprising the light emitting element according to claim 2.

4. An electronic appliance comprising the light emitting device according to claim 3.

5. The light emitting element according to claim 2, further comprising a light emitting layer between the pair of electrodes, wherein the light emitting layer comprises a light-emitting substance having a spectrum peak in a range of wavelength of 450 to 550 nm.

6. An organometallic complex represented by a general formula (2),

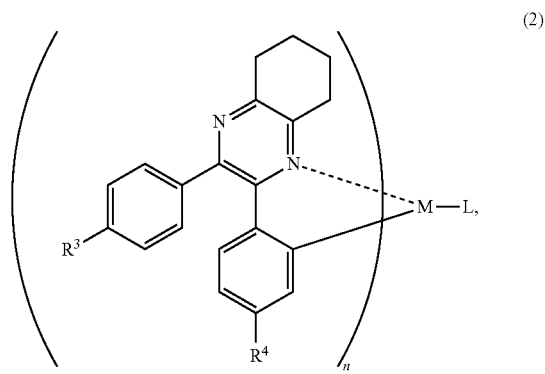

(2)

wherein each of $R^3$ and $R^4$ represents any one of hydrogen, an alkyl group, a halogen group, —$CF_3$, an alkoxy group, and an aryl group, wherein M represents an element that belongs to Group 9 or Group 10, wherein L represents a monoanionic ligand, and wherein n=2 when M is an element that belongs to Group 9, and n=1 when M is an element that belongs to Group 10.

7. An organometallic complex according to claim 6, wherein the monoanionic ligand is represented by any one of structural formulas (1) to (7),

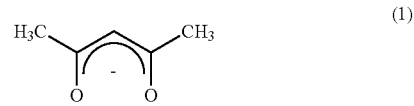

(1)

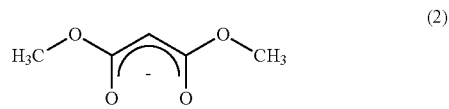

(2)

(3)

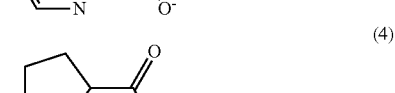

(4)

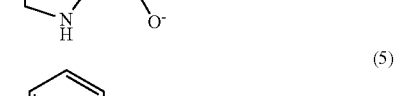

(5)

(6)

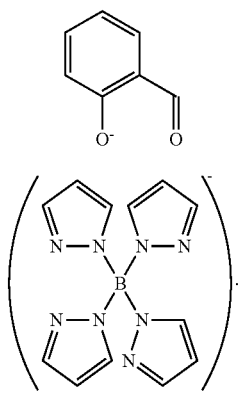

(7)

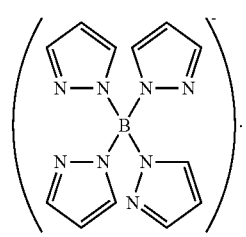

8. A light emitting element comprising a layer formed between a pair of electrodes, wherein the layer comprises the organometallic complex according to claim 6.

9. A light emitting device comprising the light emitting element according to claim 8.

10. An electronic appliance comprising the light emitting device according to claim 9.

11. The light emitting element according to claim 8, further comprising a light emitting layer between the pair of electrodes,
wherein the light emitting layer comprises a light-emitting substance having a spectrum peak in a range of wavelength of 450 to 550 nm.

12. An organometallic complex represented by a general formula (4), (4)

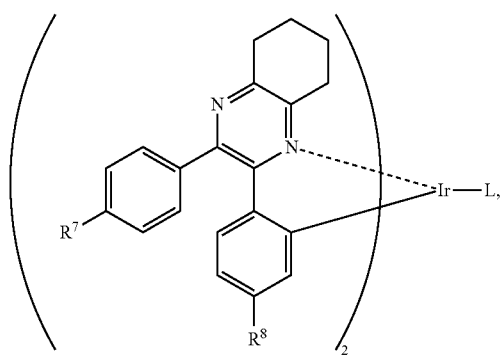

wherein each of $R^7$ and $R^8$ represents any one of hydrogen, an alkyl group having 1 to 4 carbon atoms, a halogen group, —CF$_3$, an alkoxy group having 1 to 4 carbon atoms, and a phenyl group, and
wherein L represents a monoanionic ligand.

13. An organometallic complex according to claim 12, wherein the monoanionic ligand is represented by any one of structural formulas (1) to (7), (1)

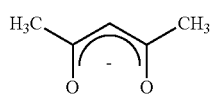

(2)

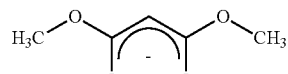

(3)

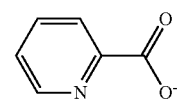

(4)

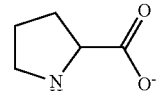

(5)

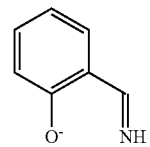

(6)

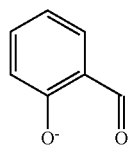

(7)

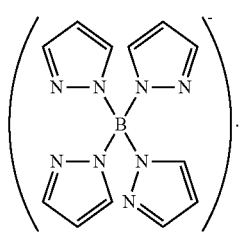

14. A light emitting element comprising a layer formed between a pair of electrodes, wherein the layer comprises the organometallic complex according to claim 12.

15. A light emitting device comprising the light emitting element according to claim 14.

16. An electronic appliance comprising the light emitting device according to claim 15.

17. The light emitting element according to claim 14, further comprising a light emitting layer between the pair of electrodes,
wherein the light emitting layer comprises a light-emitting substance having a spectrum peak in a range of wavelength of 450 to 550 nm.

18. An organometallic complex including a structure represented by a general formula (3), (3)

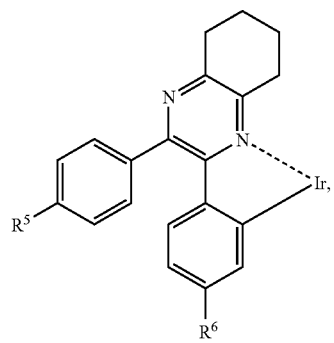

wherein each of $R^5$ and $R^6$ represents any one of hydrogen, an alkyl group having 1 to 4 carbon atoms, a halogen group, —CF$_3$, an alkoxy group having 1 to 4 carbon atoms, and a phenyl group.

19. A light emitting element comprising a layer formed between a pair of electrodes, wherein the layer comprises the organometallic complex according to claim 18.

20. A light emitting device comprising the light emitting element according to claim 19.

21. An electronic appliance comprising the light emitting device according to claim 20.

22. The light emitting element according to claim 19, further comprising a light emitting layer between the pair of electrodes,
wherein the light emitting layer comprises a light-emitting substance having a spectrum peak in a range of wavelength of 450 to 550 nm.

23. An organometallic complex including a structure represented by a general formula (5),

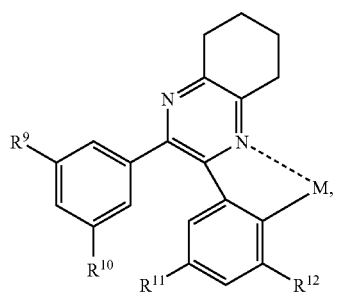

(5)

wherein each of $R^9$ to $R^{12}$ represents any one of hydrogen, an alkyl group, a halogen group, —CF$_3$, an alkoxy group, and an aryl group, and
wherein M represents an element that belongs to Group 9 or Group 10.

24. A light emitting element comprising a layer formed between a pair of electrodes, wherein the layer comprises the organometallic complex according to claim 23.

25. A light emitting device comprising the light emitting element according to claim 24.

26. An electronic appliance comprising the light emitting device according to claim 25.

27. The light emitting element according to claim 24, further comprising a light emitting layer between the pair of electrodes,
wherein the light emitting layer comprises a light-emitting substance having a spectrum peak in a range of wavelength of 450 to 550 nm.

28. An organometallic complex represented by a general formula (6),

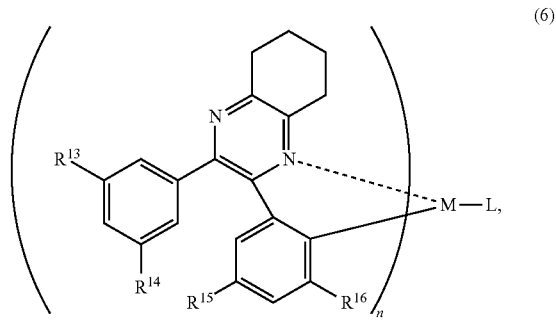

(6)

wherein each of $R^{13}$ to $R^{16}$ represents any one of hydrogen, an alkyl group, a halogen group, —CF$_3$, an alkoxy group, and an aryl group,
wherein M represents an element that belongs to Group 9 or Group 10,
wherein L represents a monoanionic ligand, and
wherein n=2 when M is an element that belongs to Group 9, and n=1 when M is an element that belongs to Group 10.

29. An organometallic complex according to claim 28, wherein the monoanionic ligand is represented by any one of structural formulas (1) to (7),

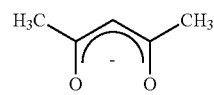

(1)

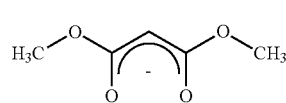

(2)

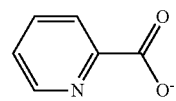

(3)

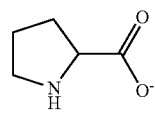

(4)

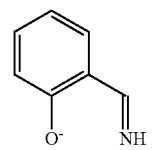

(5)

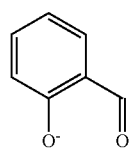

(6)

(7)

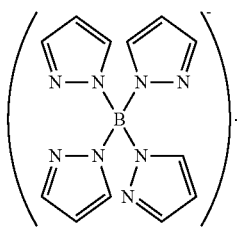

30. A light emitting element comprising a layer formed between a pair of electrodes, wherein the layer comprises the organometallic complex according to claim 28.

31. A light emitting device comprising the light emitting element according to claim 30.

32. An electronic appliance comprising the light emitting device according to claim 31.

33. The light emitting element according to claim 30, further comprising a light emitting layer between the pair of electrodes,
   wherein the light emitting layer comprises a light-emitting substance having a spectrum peak in a range of wavelength of 450 to 550 nm.

34. An organometallic complex including a structure represented by a general formula (7), (7)

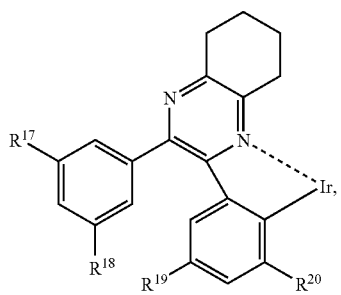

wherein each of $R^{17}$ to $R^{20}$ represents any one of hydrogen, an alkyl group having 1 to 4 carbon atoms, a halogen group, —$CF_3$, an alkoxy group having 1 to 4 carbon atoms, and a phenyl group.

35. A light emitting element comprising a layer formed between a pair of electrodes, wherein the layer comprises the organometallic complex according to claim 34.

36. A light emitting device comprising the light emitting element according to claim 35.

37. An electronic appliance comprising the light emitting device according to claim 36.

38. The light emitting element according to claim 35, further comprising a light emitting layer between the pair of electrodes,
   wherein the light emitting layer comprises a light emitting substance having a spectrum peak in a range of wavelength of 450 to 550 nm.

39. An organometallic complex represented by a general formula (8), (8)

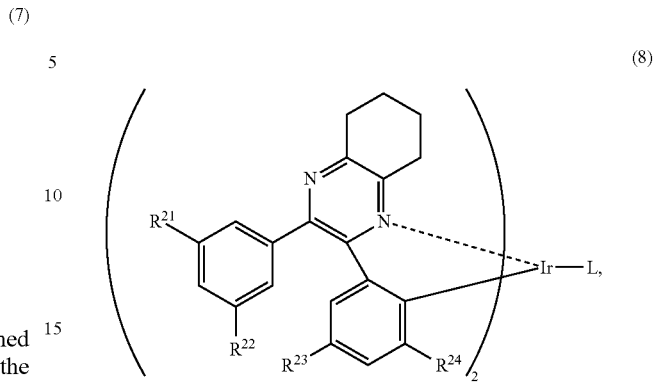

wherein each of $R^{21}$ to $R^{24}$ represents any one of hydrogen, an alkyl group having 1 to 4 carbon atoms, a halogen group, —$CF_3$, an alkoxy group having 1 to 4 carbon atoms, and a phenyl group, and
wherein L represents a monoanionic ligand.

40. An organometallic complex according to claim 39, wherein the monoanionic ligand is represented by any one of structural formulas (1) to (7), (1)
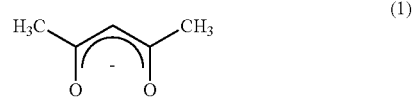

(2)
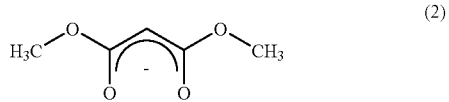

(3)

(4)
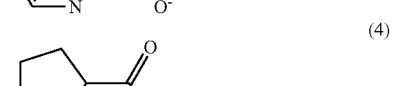

(5)
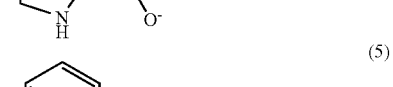

(6)

(7)
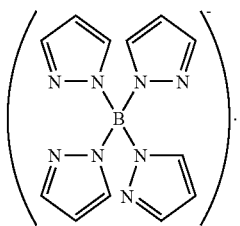

41. A light emitting element comprising a layer formed between a pair of electrodes, wherein the layer comprises the organometallic complex according to claim 39.

42. A light emitting device comprising the light emitting element according to claim 41.

43. An electronic appliance comprising the light emitting device according to claim 42.

44. The light emitting element according to claim 41, further comprising a light emitting layer between the pair of electrodes,
wherein the light emitting layer comprises a light emitting substance having a spectrum peak in a range of wavelength of 450 to 550 nm.

45. An organometallic complex including a structure represented by a general formula (9),

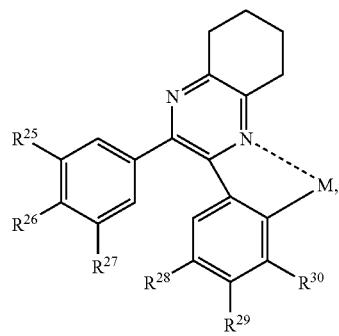

(9)

wherein each of $R^{25}$ to $R^{30}$ represents any one of hydrogen, an alkyl group, a halogen group, —$CF_3$, and an alkoxy group, and
wherein M represents an element that belongs to Group 9 or Group 10.

46. A light emitting element comprising a layer formed between a pair of electrodes, wherein the layer comprises the organometallic complex according to claim 45.

47. A light emitting device comprising the light emitting element according to claim 46.

48. An electronic appliance comprising the light emitting device according to claim 47.

49. The light emitting element according to claim 46, further comprising a light emitting layer between the pair of electrodes,
wherein the light emitting layer comprises a light emitting substance having a spectrum peak in a range of wavelength of 450 to 550 nm.

50. An organometallic complex represent by a general formula (10),

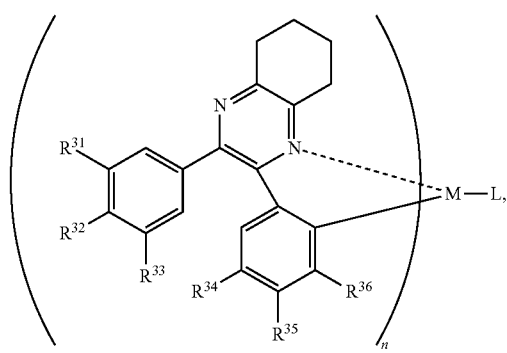

(10)

wherein each of $R^{31}$ to $R^{36}$ represents any one of hydrogen, an alkyl group, a halogen group, —$CF_3$, and an alkoxy group,
wherein L represents a monoanionic ligand, and
wherein n=2 when M is an element that belongs to Group 9, and n=1 when M is an element that belongs to Group 10.

51. An organometallic complex according to claim 50, wherein the monoanionic ligand is represented by any one of structural formulas (1) to (7),

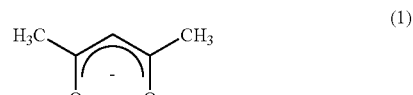
(1)

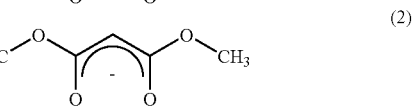
(2)

(3)

(4)

(5)

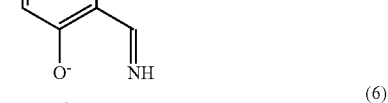
(6)

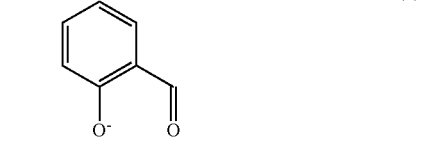
(7)

52. A light emitting element comprising a layer formed between a pair of electrodes, wherein the layer comprises the organometallic complex according to claim 50.

53. A light emitting device comprising the light emitting element according to claim 52.

54. An electronic appliance comprising the light emitting device according to claim 53.

55. The light emitting element according to claim 52, further comprising a light emitting layer between the pair of electrodes,
wherein the light emitting layer comprises a light emitting substance having a spectrum peak in a range of wavelength of 450 to 550 nm.

56. An organometallic complex including a structure represented by a general formula (11),

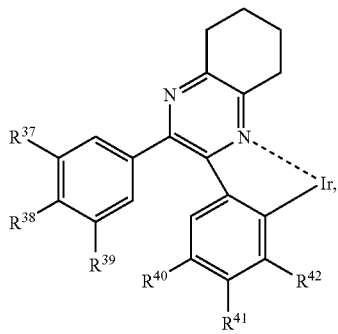

(11)

wherein each of $R^{37}$ to $R^{42}$ represents any one of hydrogen, an alkyl group having 1 to 4 carbon atoms, a halogen group, —$CF_3$, and an alkoxy group having 1 to 4 carbon atoms.

57. A light emitting element comprising a layer formed between a pair of electrodes, wherein the layer comprises the organometallic complex according to claim 56.

58. A light emitting device comprising the light emitting element according to claim 57.

59. An electronic appliance comprising the light emitting device according to claim 58.

60. The light emitting element according to claim 57, further comprising a light emitting layer between the pair of electrodes,
wherein the light emitting layer comprises a light emitting substance having a spectrum peak in a range of wavelength of 450 to 550 nm.

61. An organometallic complex represented by a general formula (12),

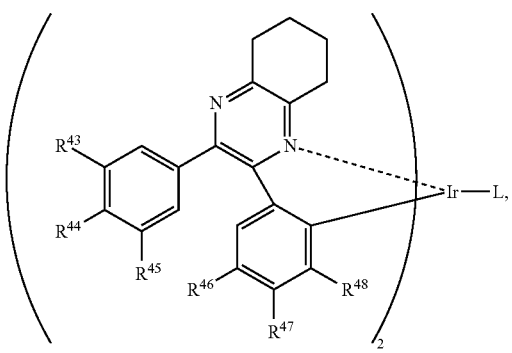

(12)

wherein each of $R^{43}$ to $R^{48}$ represents any one of hydrogen, an alkyl group having 1 to 4 carbon atoms, a halogen group, —$CF_3$, and an alkoxy group having 1 to 4 carbon atoms, and
wherein L represents a monoanionic ligand.

62. An organometallic complex according to claim 61, wherein the monoanionic ligand is represented by any one of structural formulas (1) to (7),

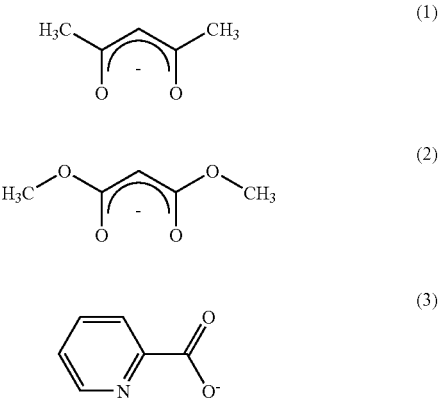

(1)

(2)

(3)

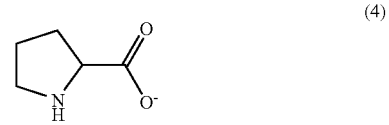

(4)

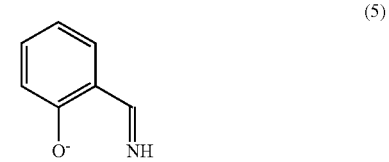

(5)

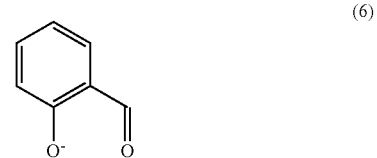

(6)

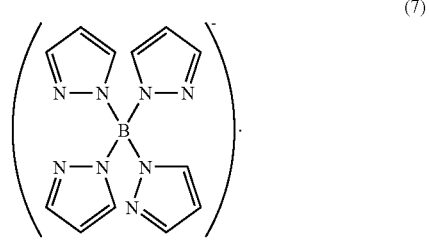

(7)

63. A light emitting element comprising a layer formed between a pair of electrodes, wherein the layer comprises the organometallic complex according to claim 61.

64. A light emitting device comprising the light emitting element according to claim 63.

65. An electronic appliance comprising the light emitting device according to claim 64.

66. The light emitting element according to claim 63, further comprising a light emitting layer between the pair of electrodes,
wherein the light emitting layer comprises a light emitting substance having a spectrum peak in a range of wavelength of 450 to 550 nm.

67. An organometallic complex represented by a general formula (13),

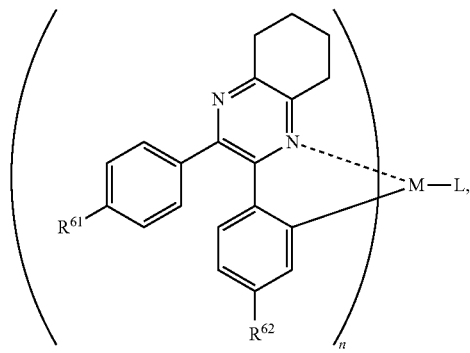

(13)

wherein each of $R^{49}$ and $R^{50}$ represents any one of hydrogen and fluorine,
wherein M represents iridium or platinum,
wherein L represents a ligand represented by any one of structural formulas (36) to (38),

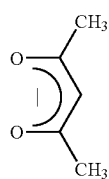

(36)

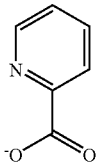

(37)

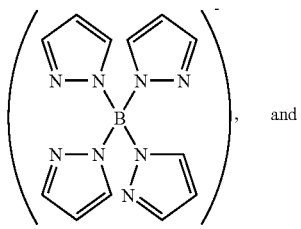

(38)

, and wherein n=2 when M is iridium, and n=1 when M is platinum.

68. A light emitting element comprising a layer formed between a pair of electrodes, wherein the layer comprises the organometallic complex according to claim 67.

69. A light emitting device comprising the light emitting element according to claim 68.

70. The light emitting element according to claim 68, further comprising a light emitting layer between the pair of electrodes,
wherein the light emitting layer comprises a light emitting substance having a spectrum peak in a range of wavelength of 450 to 550 nm.

71. An electronic appliance comprising the light emitting device according to claim 69.

* * * * *